(12) United States Patent
Jaschinski et al.

(10) Patent No.: US 12,024,708 B2
(45) Date of Patent: Jul. 2, 2024

(54) ANGPTL4 OLIGONUCLEOTIDES INFLUENCING THE REGULATION OF THE FATTY ACID METABOLISM

(71) Applicant: Lipigon Pharmaceuticals AB, Umeå (SE)

(72) Inventors: Frank Jaschinski, Marburg (DE); Anne Sadewasser, Marburg (DE); Sven Michel, Marburg (DE)

(73) Assignee: LIPIGON PHARMACEUTICALS AB, Umeå (SE)

( * ) Notice: Subject to any disclaimer, the term of this patent is extended or adjusted under 35 U.S.C. 154(b) by 0 days.

(21) Appl. No.: 17/293,356

(22) PCT Filed: Nov. 13, 2019

(86) PCT No.: PCT/EP2019/081161
§ 371 (c)(1),
(2) Date: May 12, 2021

(87) PCT Pub. No.: WO2020/099478
PCT Pub. Date: May 22, 2020

(65) Prior Publication Data
US 2022/0010311 A1 Jan. 13, 2022

(30) Foreign Application Priority Data
Nov. 13, 2018 (EP) .................................... 18206087

(51) Int. Cl.
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/3231* (2013.01)

(58) Field of Classification Search
CPC .......................... C12N 15/113; C12N 2310/11
See application file for complete search history.

(56) References Cited

U.S. PATENT DOCUMENTS

| | | | |
|---|---|---|---|
| 2005/0272080 A1 | 12/2005 | Palma | |
| 2017/0233466 A1 | 8/2017 | Gromada | |
| 2018/0044672 A1* | 2/2018 | Zehendner | ............... A61P 35/02 |
| 2022/0162613 A1 | 5/2022 | Jaschinski et al. | |

FOREIGN PATENT DOCUMENTS

| | | |
|---|---|---|
| JP | 2016-520310 A | 7/2016 |
| WO | WO 2001/077151 A2 | 10/2001 |
| WO | WO 2006/005035 A2 | 2/2006 |
| WO | WO 2006/014678 A2 | 2/2006 |
| WO | WO 2011/005793 A1 | 1/2011 |
| WO | WO 2011/046515 A1 | 4/2011 |
| WO | WO 2011/085271 A2 | 7/2011 |
| WO | WO 2012/005898 A2 | 1/2012 |
| WO | WO 2012/177784 A2 | 12/2012 |
| WO | WO 2014/188001 A1 | 11/2014 |
| WO | WO 2016/154127 A2 | 9/2016 |
| WO | WO 2018/002719 A1 * | 1/2018 ........... C12N 15/111 |
| WO | WO 2020/099478 A2 | 5/2020 |

OTHER PUBLICATIONS

Gregory et al. (Am J Physiol Lung Cell Mol Physiol, 309, L1041-L1046, 2015).*
International Search Report dated Jul. 17, 2020 in International Application No. PCT/EP2019/081161.
Lee et al., Identification of a New Functional Domain in Angiopoietin-like 3 (ANGPTL3) and Angiopoietin-like 4 (ANGPTL4) Involved in Binding and Inhibition of Lipoprotein Lipase (LPL), Journal of Biological Chemistry, vol. 284, No. 20, pp. 13735-13745, 2009.
Zhang et al., The ANGPTL3-4-8 Model, a Molecular Mechanism for Triglyceride Trafficking, Open Biology, vol. 6, No. 150272, pp. 1-11, 2016.
Written Opinion dated Jul. 17, 2020 in International Application No. PCT/EP2019/081161.
Athyros et al., Long-term Follow-up of Patients With Acute Hypertriglyceridemia-Induced Pancreatitis, Journal of Clinical Gastroenterology, vol. 34, No. 4, pp. 472-475, 2002.
Beigneux et al., Glycosylphosphatidylinositol-Anchored High-Density Lipoprotein-Binding Protein 1 Plays a Critical Role in the Lipolytic Processing of Chylomicrons, Cell Metabolism, vol. 5, Issue 5, pp. 279-291, 2007.
Benlian et al., Phenotypic Expression in Double Heterozygotes for Familial Hypercholesterolemia and Familial Defective Apolipoprotein B-100, Human Mutation, vol. 7, Issue 4, pp. 340-345, 1996.
Breckenridge et al., Hypertriglyceriemia Associated with Deficiency of Apolipoprotein C-II, The New England Journal of Medicine, vol. 298, No. 23, pp. 1266-1273, 1978.
Chen et al., Knockdown of angiopoietin-like 4 inhibits the development of human gastric cancer, Oncology Reports, vol. 39, Issue 4, pp. 1739-1746, 2018.
Cullen, P., Evidence That Triglycerides Are an Independent Coronary Heart Disease Risk Factor, The American Journal of Cardiology, vol. 86, Issue 9, pp. 943-949, 2000.
Desai et al., Lipid-lowering effects of anti-angiopoietin-like 4 antibody recapitulate the lipid phenotype found in angiopoietin-like 4 knockout mice, PNAS, vol. 104, No. 28, pp. 11766-11771, 2007.
Graham et al., Cardiovascular and Metabolic Effects of ANGPTL3 Antisense Oligonucleotides, The New England Journal of Medicine, vol. 377, No. 3, pp. 222-232, 2017.
Ishihara et al., A sandwich enzyme-linked immunosorbent assay for human plasma apolipoprotein A-V concentration, Journal of Lipid Research, vol. 46, Issue 9, pp. 2015-2022, 2005.

(Continued)

*Primary Examiner* — Amy Rose Hudson
(74) *Attorney, Agent, or Firm* — Knobbe, Martens, Olson & Bear, LLP

(57) ABSTRACT

An ANGPTL4 inhibitor consisting of an oligonucleotide has 12 to 22 nucleotides. At least one of the nucleotides is modified, and the oligonucleotide hybridizes with a nucleic acid sequence of human and/or mouse ANGPTL4 and inhibits the expression of ANGPTL4. Also disclosed herein is a pharmaceutical composition of the ANGPTL4 inhibitor and a pharmaceutically acceptable carrier, excipient, diluent, or a combination thereof.

18 Claims, 27 Drawing Sheets

Specification includes a Sequence Listing.

(56) References Cited

OTHER PUBLICATIONS

Johansen et al., An Increased Burden of Common and Rare Lipid-Associated Risk Alleles Contributes to the Phenotypic Spectrum of Hypertriglyceridemia, Arterioscler, Thrombosis, and Vascular Biology, vol. 31, No. 8, pp. 1916-1926, 2011.
Kauppinen et al., Locked nucleaic acid (LNA): High affinity targeting of RNA for diagnostics and therapeutics, Drug Discovery Today: Technologies, vol. 2, Issue 3, pp. 287-290, 2005.
Li et al., Angiopoietin-like 4 Increases Pulmonary Tissue Leakiness and Damage during Influenza Pneumonia, Cell Reports, vol. 10, Issue 5, pp. 654-663, 2015.
Majilessi et al., Advantages of 2-o-methy; oligorbonucleoticde probes for detecting RNA targets, Nucleaic Acid Research, 1998, vol. 26, Issue 9, pp. 2224-2229, 1998.
Nordestgaard et al., Triglycerides and cardiovascular disease, Lancet, vol. 384, Issue 9443, pp. 626-635, 2014.
Reaven, G, Pathophysiology of Insulin Resistance in Human Disease, Physiological Reviews, vol. 5, No. 3, pp. 473-486, 1995.
Stanton et al., Chemical Modification Study of Antisense Gapmers, Nucleic Acid Therapeutics, vol. 22, No. 5, pp. 344-359, 2021.
Stanton et al., Chemical Modification Study of Antisense Gapmers, Nucleic Acid Therapeutics, vol. 22, No. 5, pp. 344-359, Supplementary Figure 1, 2021.
Stanton et al., Chemical Modification Study of Antisense Gapmers, Nucleic Acid Therapeutics, vol. 22, No. 5, pp. 344-359, Supplementary Table 1, 2021.
Tsuang et al., Hypertriglyceridemic Pancreatitis: Presentation and Management, The American Journal of Gastroenterology, vol. 104, No. 4, pp. 984-991, doi: 10.1038/ajg.2009.27, 2009.
Yu et al., Effects of ANGPTL3 antisense oligodeoxynucleotides transfection on the cell growths and invasion of human hepatocellular carcinoma cells, Hepato-Gastroenterology, vol. 58, pp. 1742-1746, 2011.
Zhang et al., Down-modulation of cancer targets using locked nucleic acid (LNA)-based antisense oligonucleotides without transfection, Gene Therapy, vol. 18, pp. 326-333, 2011.
Chen et al., Knockdown of angiopoietin like 4 inhibits the development of human gastric cancer, Oncology Reports, vol. 39, pp. 1739-1746, 2018.
Zhang et al., Acquisition of anoikis resistance revels a synoikis-like survival style in BEL7402 hepatoma cells, Cancer Letters, vol. 267, pp. 106-115, 2008.

\* cited by examiner

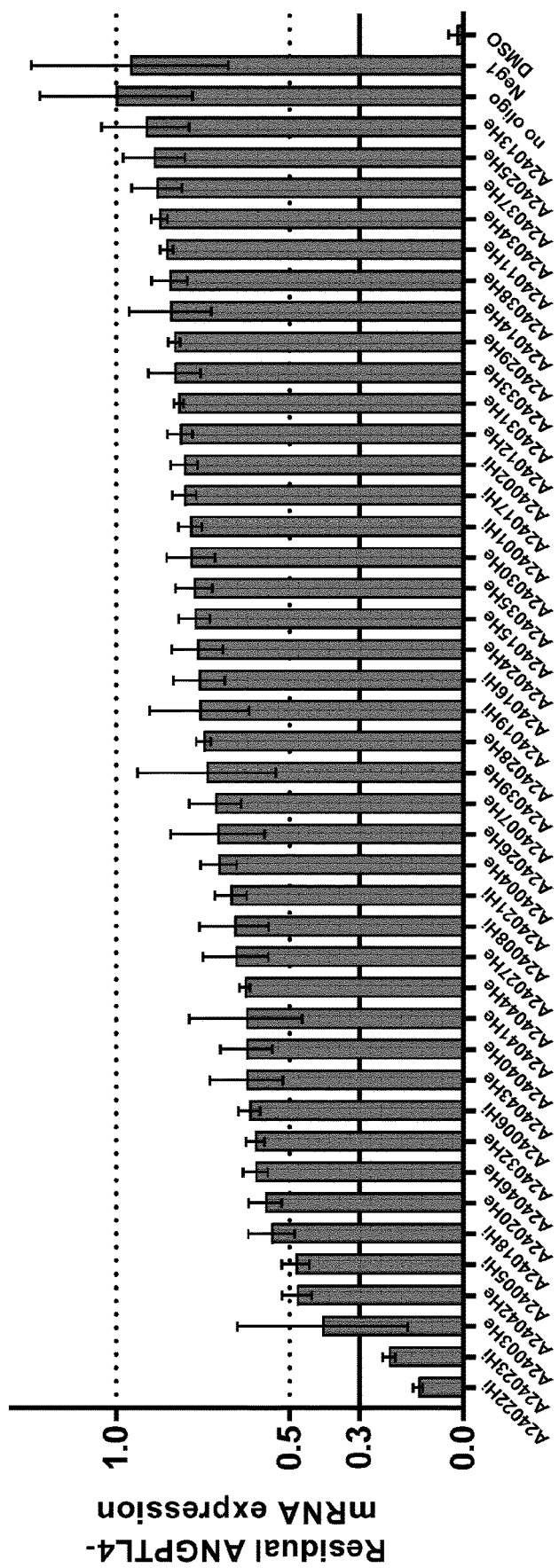
Fig. 1: Single dose efficacy screen of human ANGPTL4-specific antisense oligonucleotides in HeLa cells

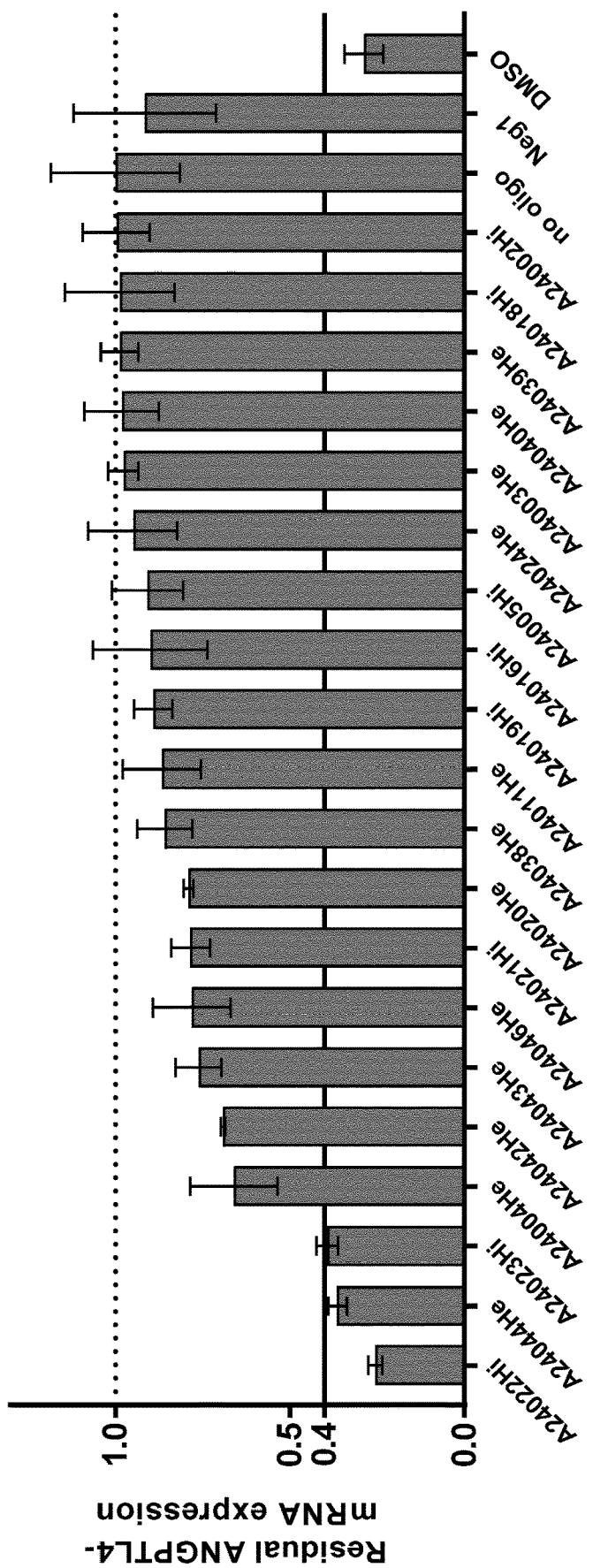
Fig. 2: 2nd screen of human ANGPTL4-specific antisense oligonucleotides in SK-OV3 cells

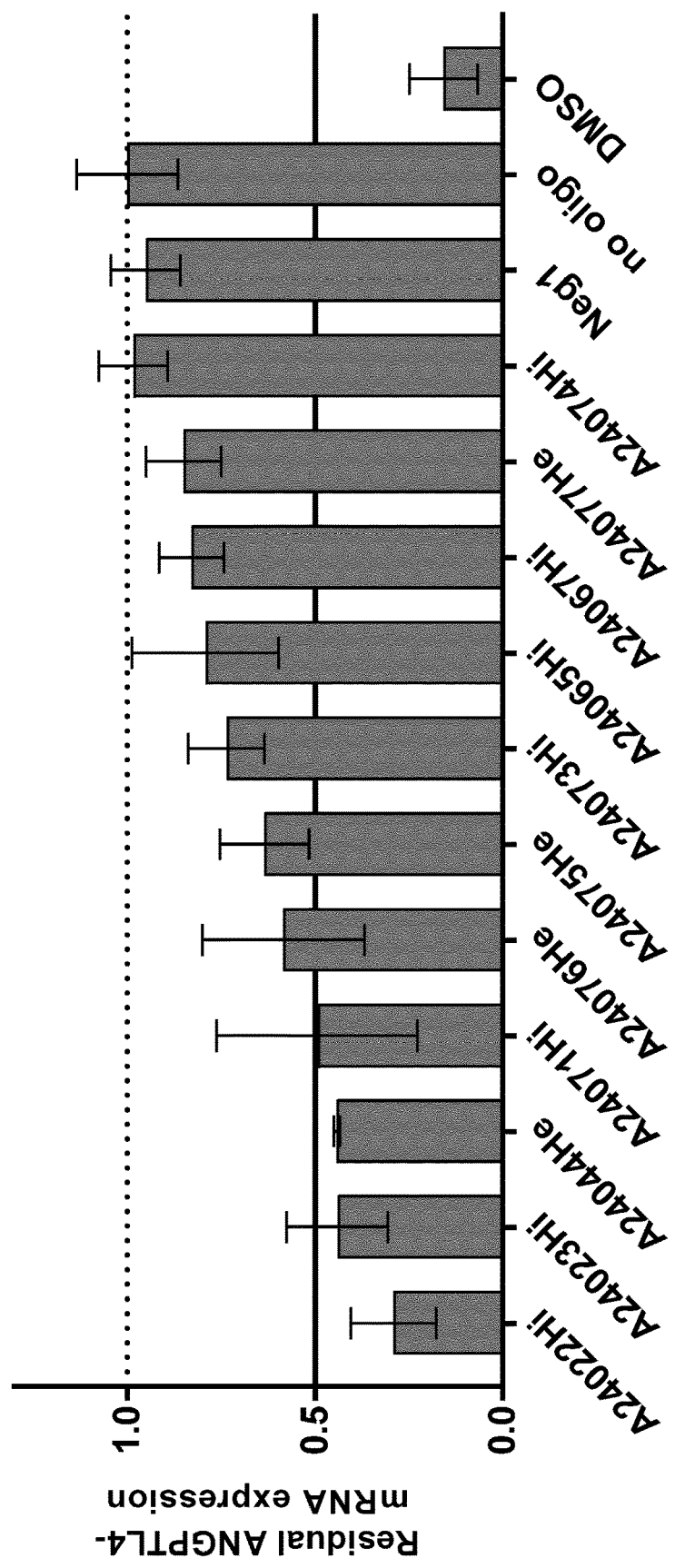
Fig. 3: Single dose efficacy screen of further human ANGPTL4-specific antisense oligonucleotides in HeLa cells

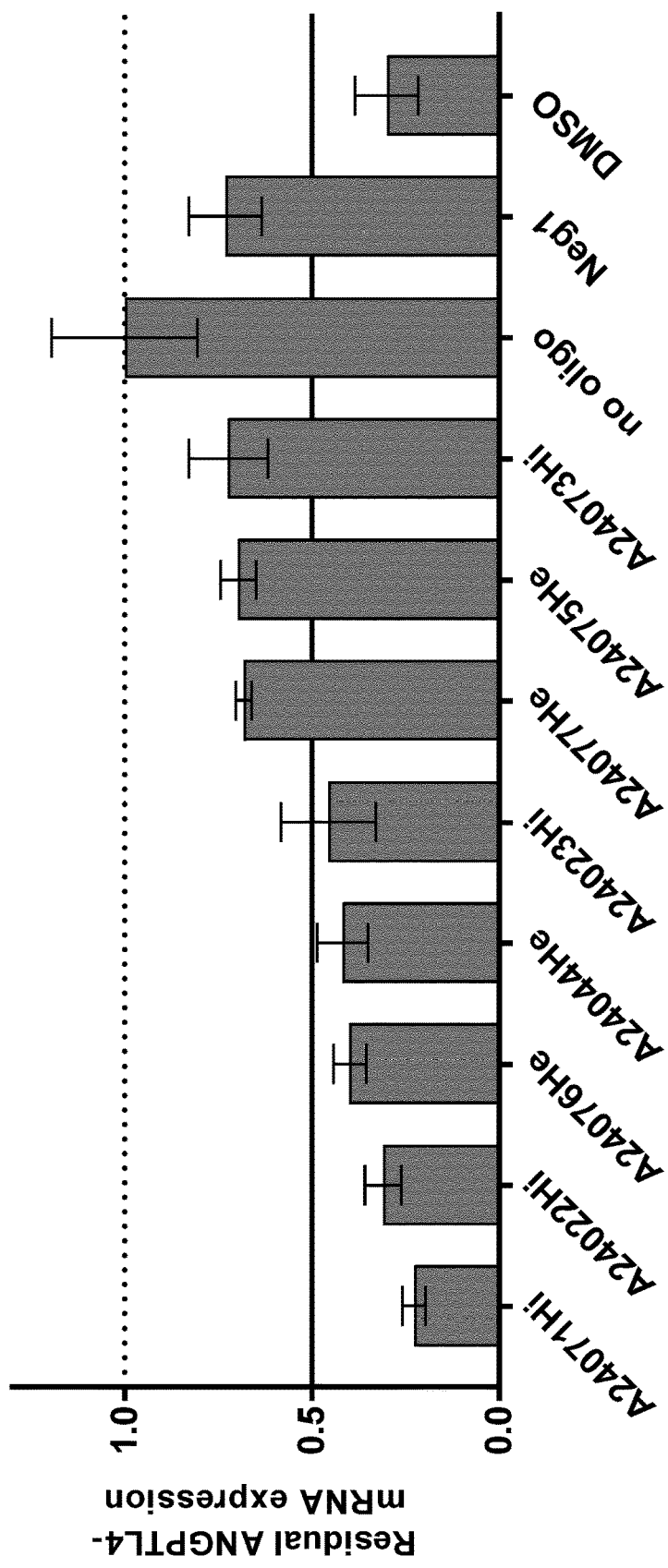
Fig. 4: Single dose efficacy screen of further human ANGPTL4-specific antisense oligonucleotides in SK-OV3 cells Fig. 5: In vitro TLR9 assay of selected human ANGPTL4-specific antisense oligonucleotides
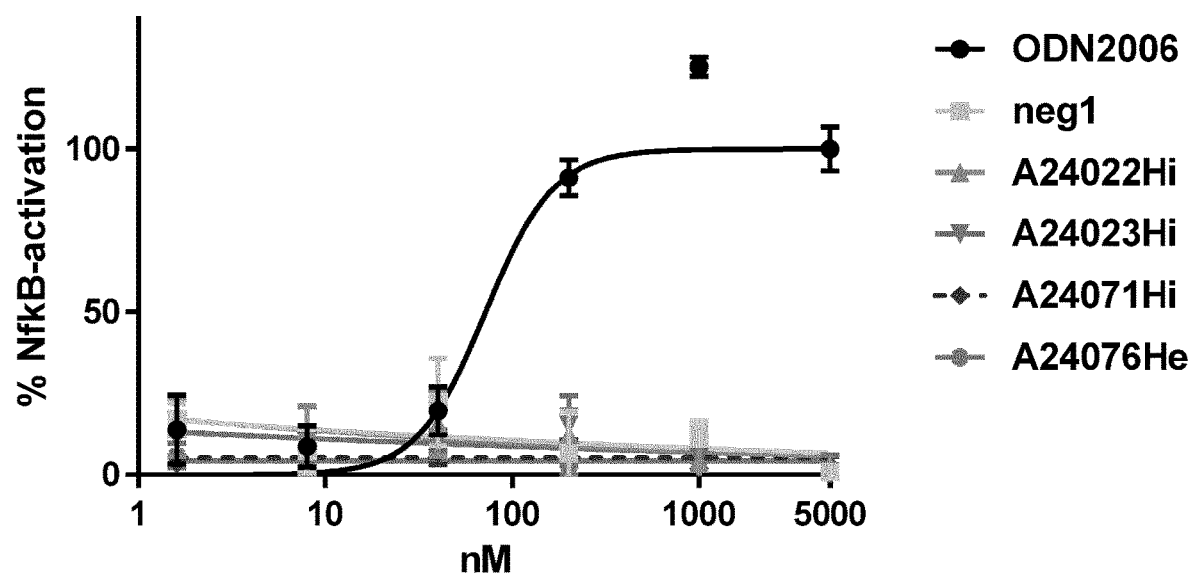

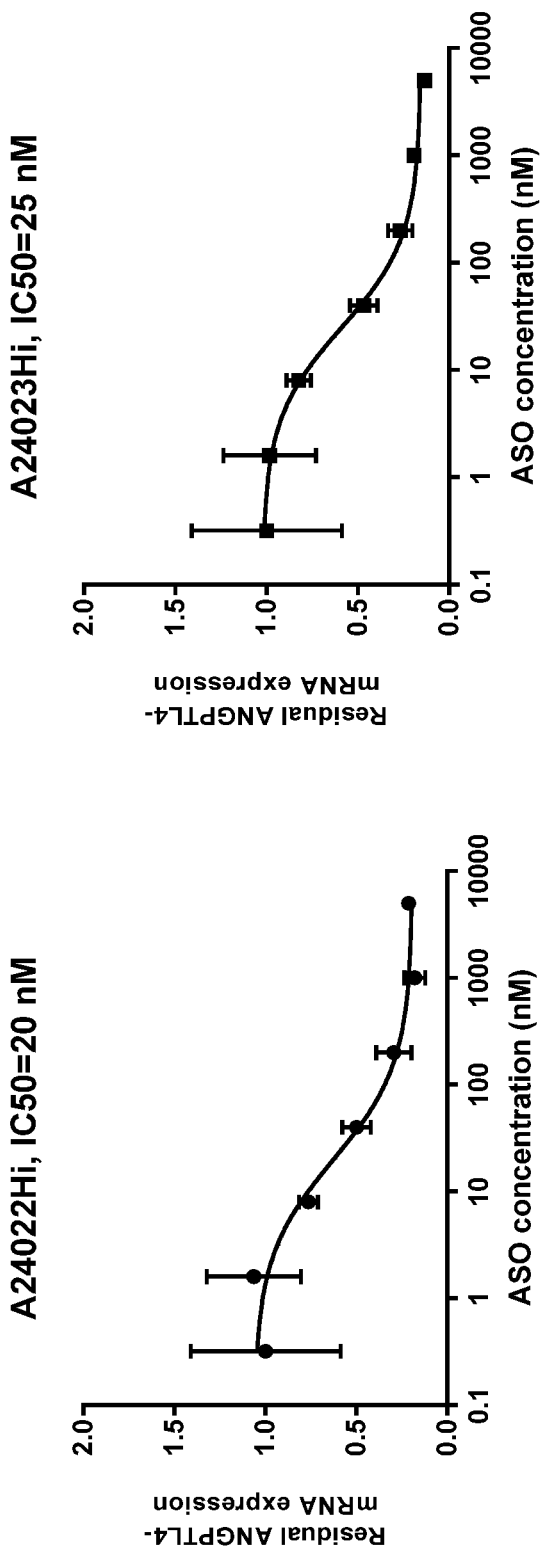
Fig. 6: IC$_{50}$ determination of selected human ANGPTL4 antisense oligonucleotides

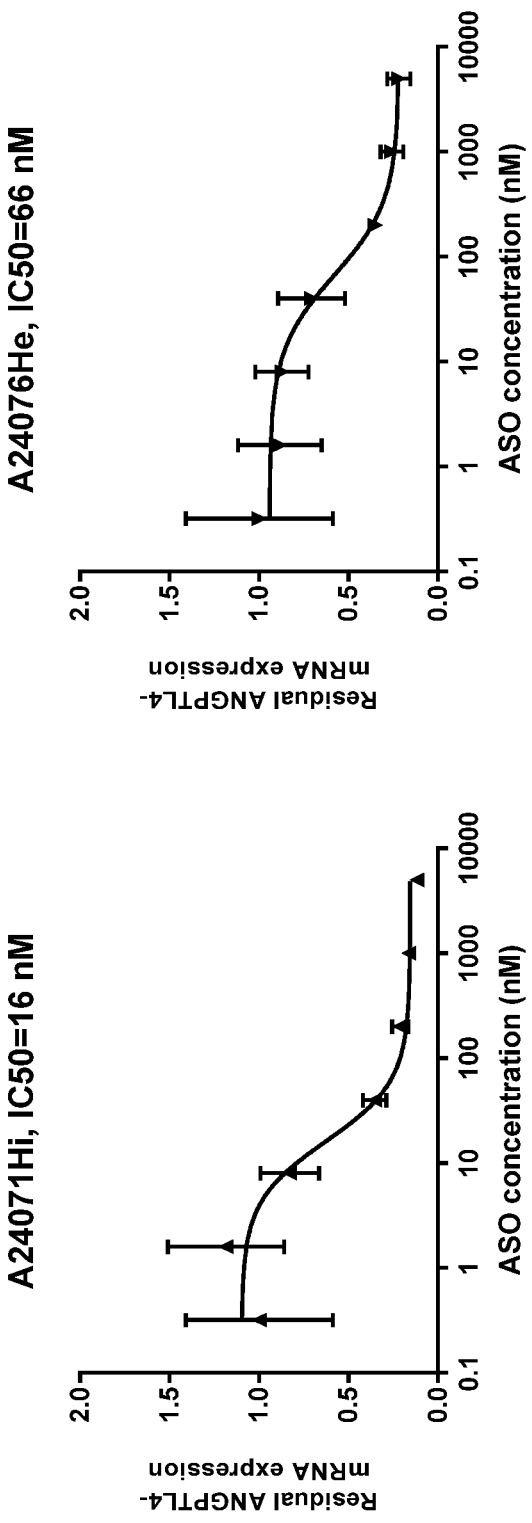
Fig. 6 (continued): IC$_{50}$ determination of selected human ANGPTL4 antisense oligonucleotides

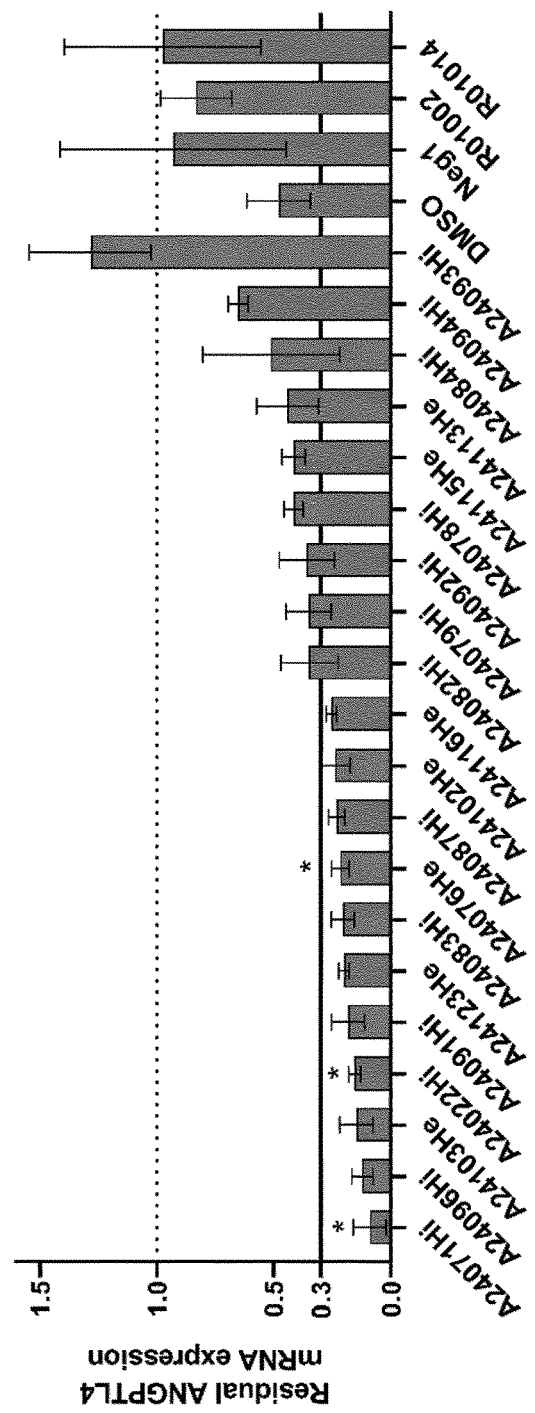
Fig. 7: 1st Single dose efficacy screen of ANGPTL4-specific antisense oligonucleotides (ASOs) in primary hepatocytes

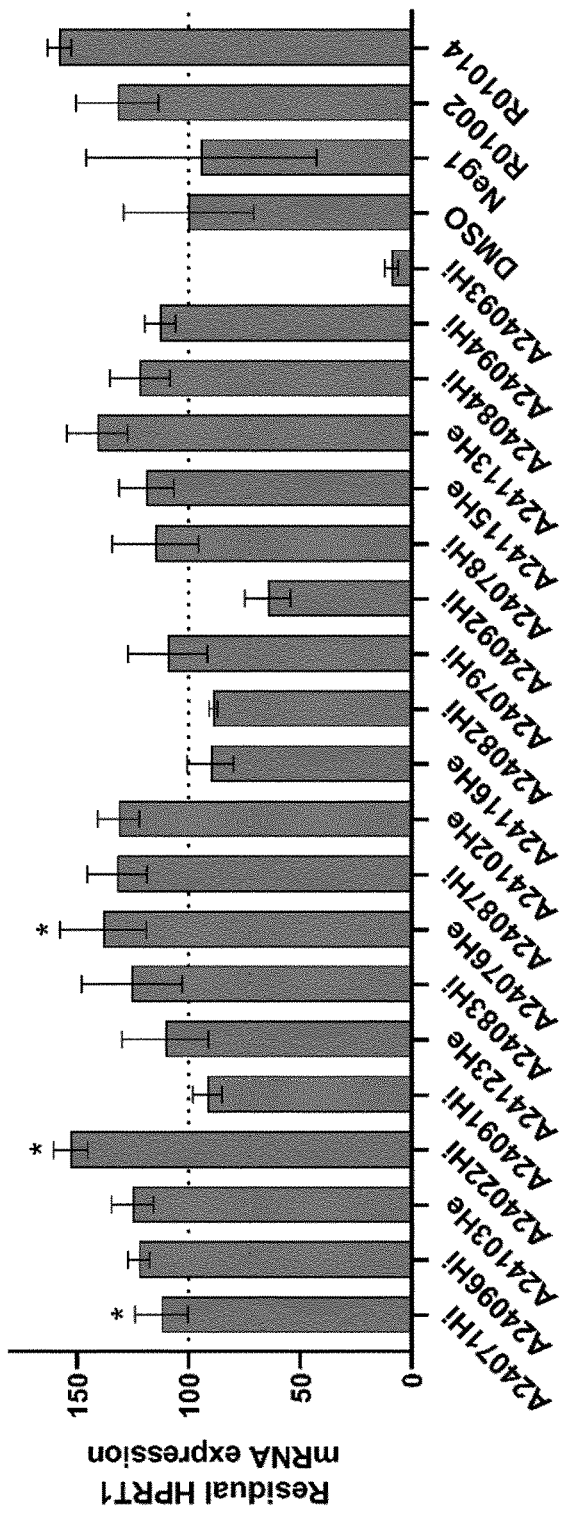
Fig. 7 (continued): 1st Single dose efficacy screen of ANGPTL4-specific antisense oligonucleotides (ASOs) in primary hepatocytes

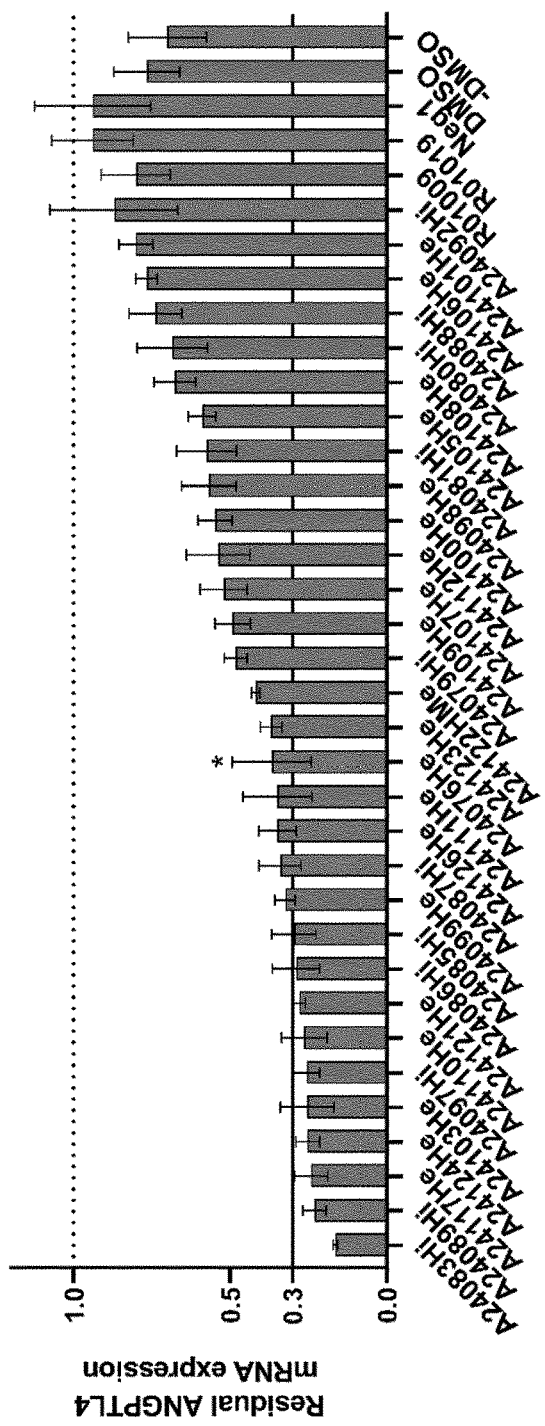
Fig. 8: 2nd Single dose efficacy screen of ANGPTL4-specific antisense oligonucleotides (ASOs) in primary hepatocytes

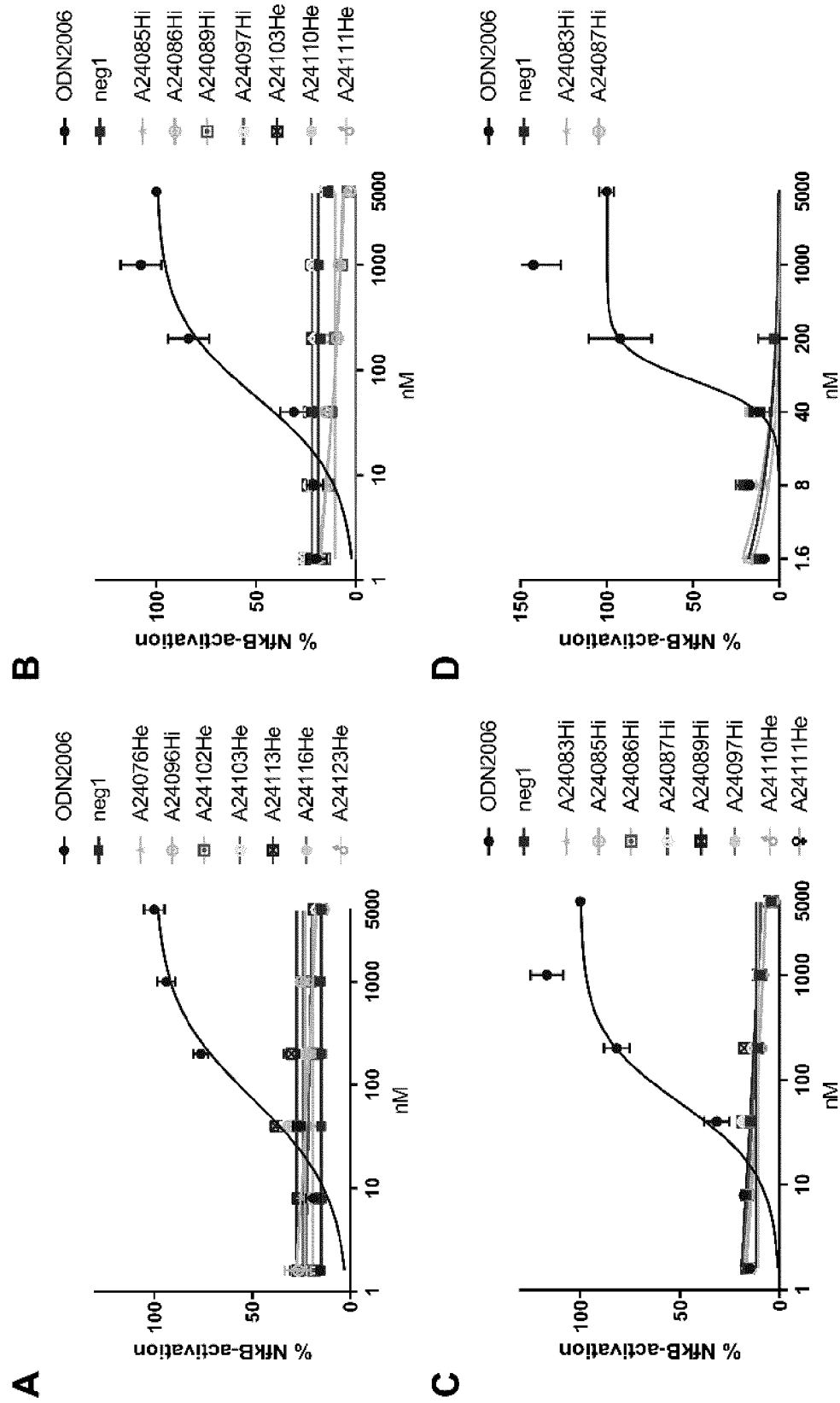
Fig. 9: NF-kB-activation in HEK-Blue hTLR9 SEAP reporter cells

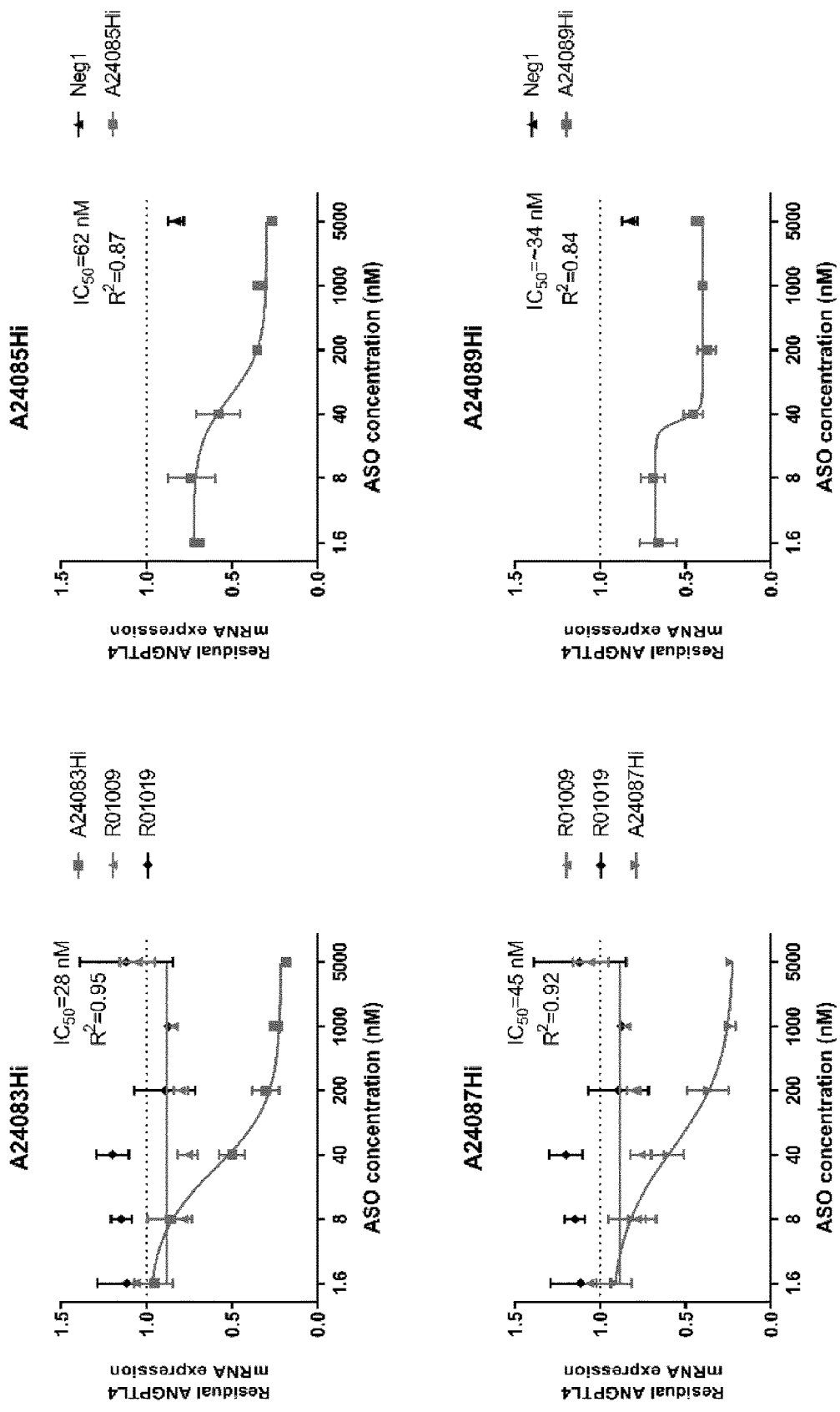
Fig. 10: IC$_{50}$ determination of selected ANGPTL4 ASOs

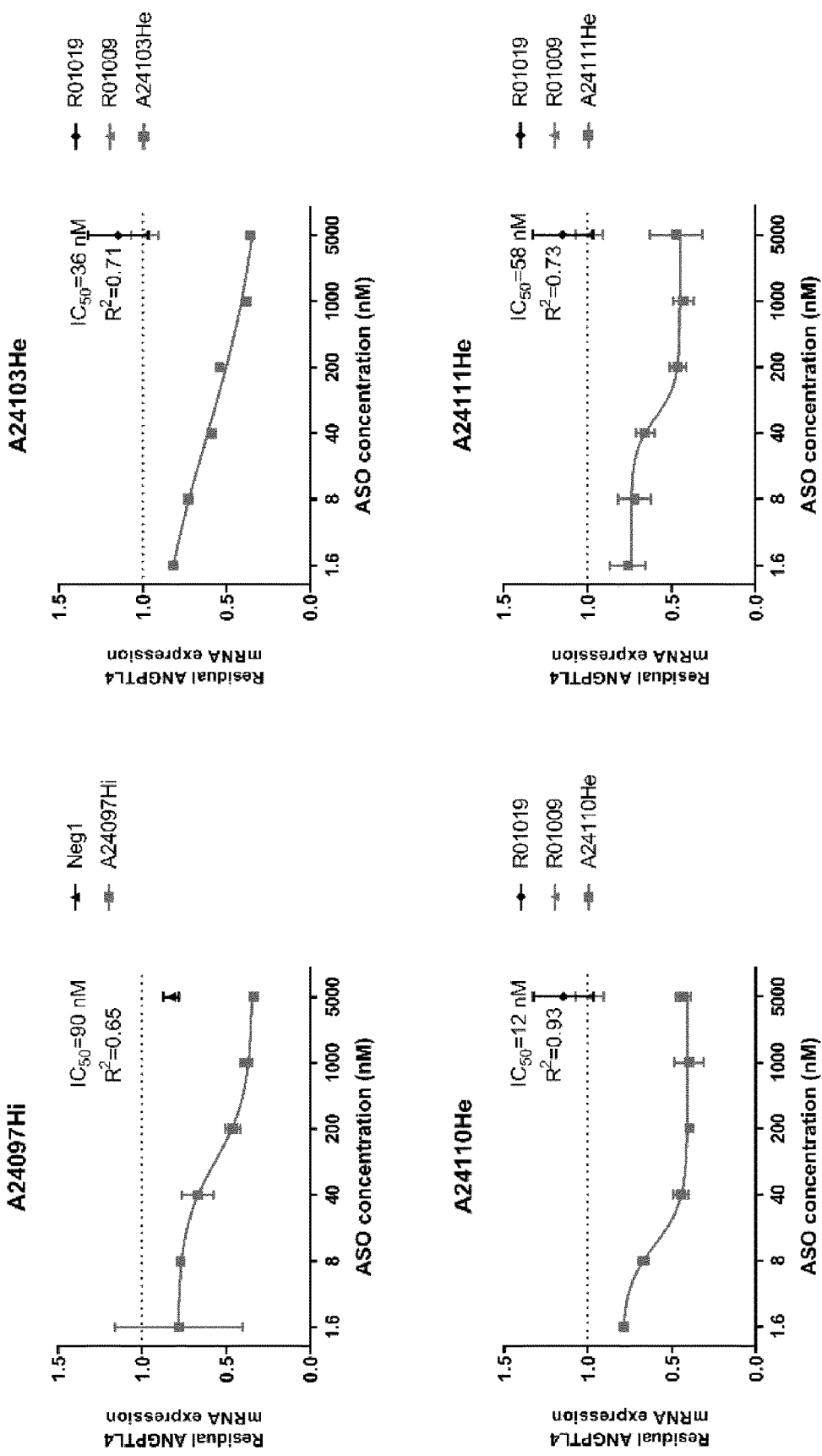
Fig. 10 (continued): IC$_{50}$ determination of selected ANGPTL4 ASOs Fig. 10 (continued): IC$_{50}$ determination of selected ANGPTL4 ASOs
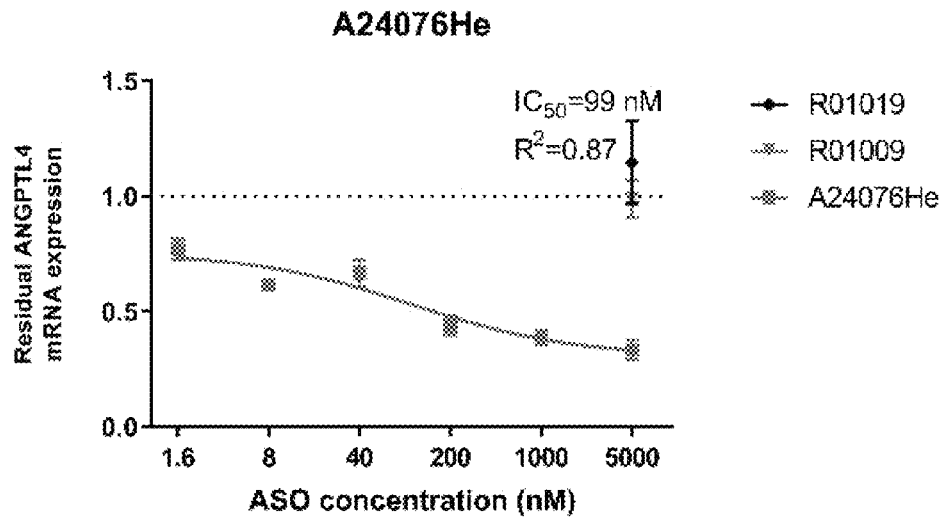
Fig. 11: Efficacy of selected ANGPTL4 ASOs on target gene expression after transfection of cynomolgus hepatocytes
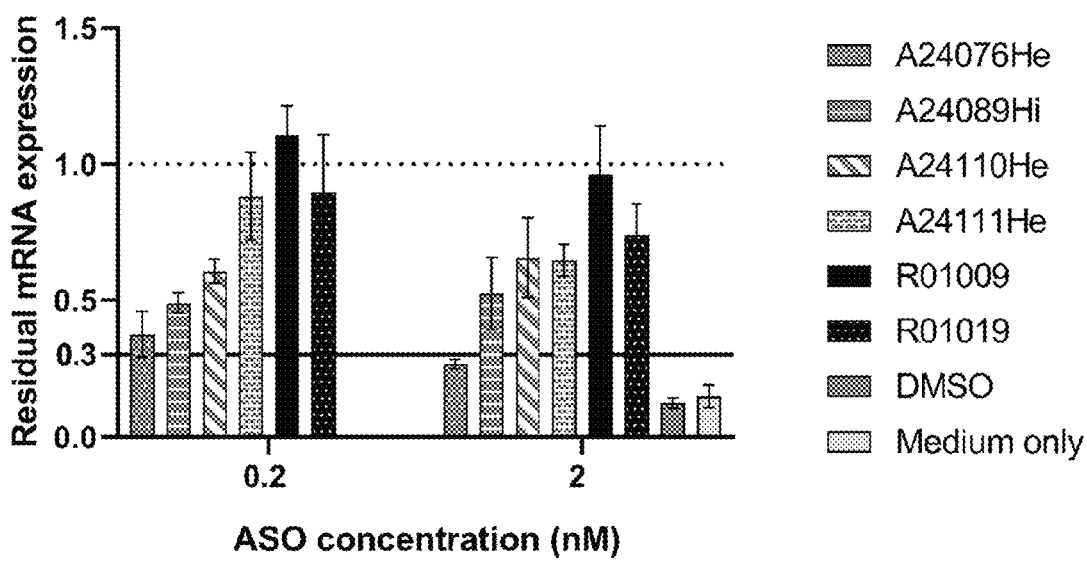

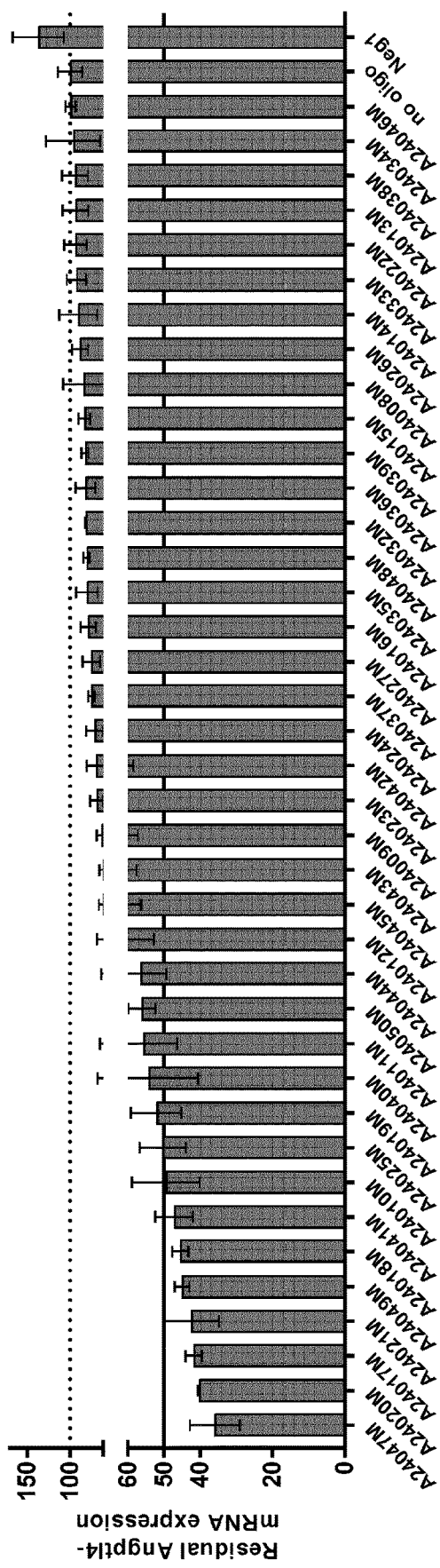
Fig. 12: Single dose efficacy screen of mouse ANGPTL4-specific antisense oligonucleotides in 3T3 cells

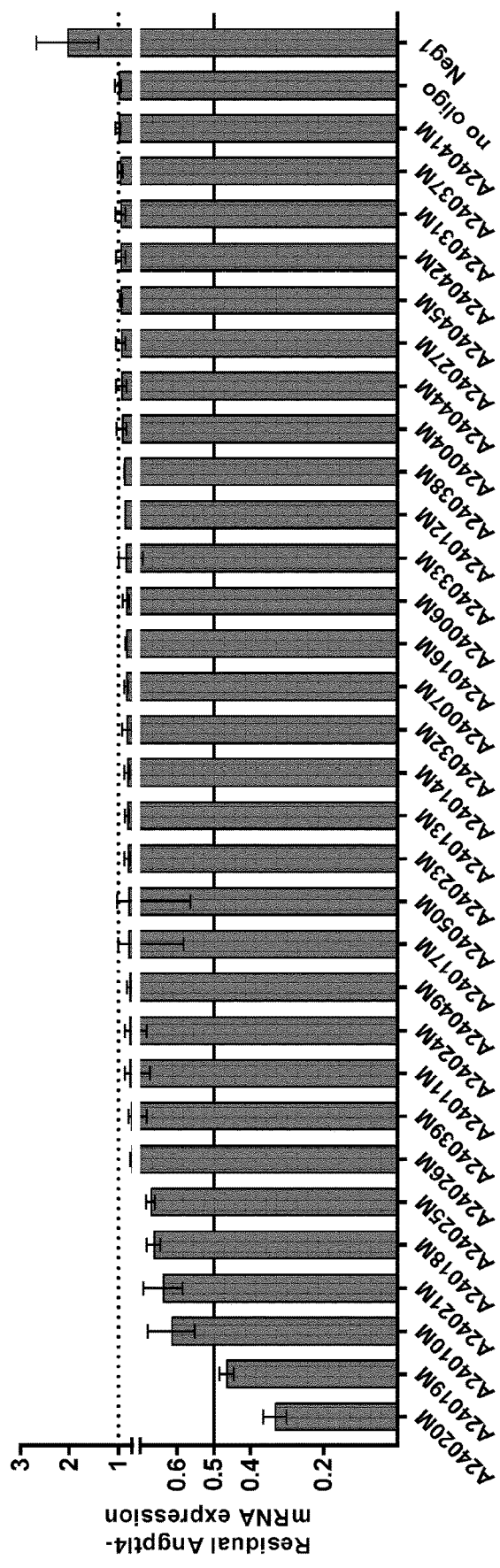
Fig. 13: 2nd single-dose screen of mouse ANGPTL4-specific antisense oligonucleotides in Renca cells

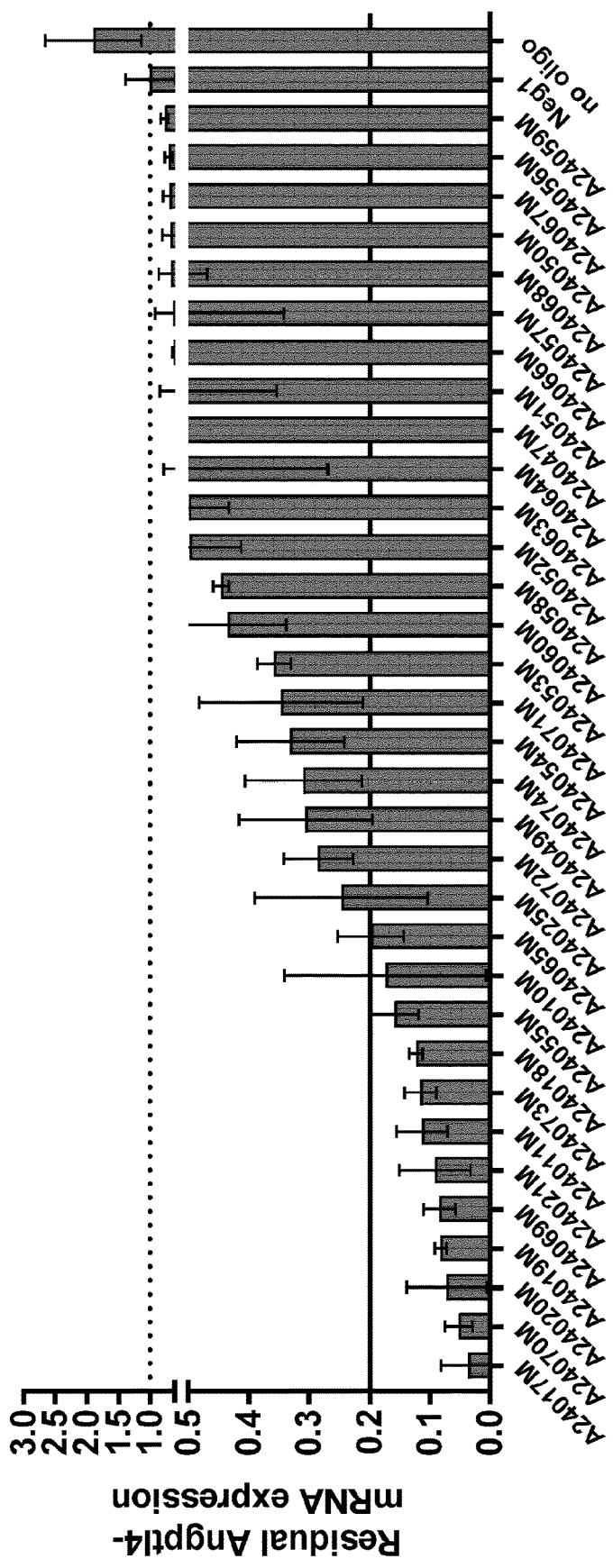
Fig. 14: Single dose efficacy screen of further mouse ANGPTL4-specific antisense oligonucleotides in 4T1 cells

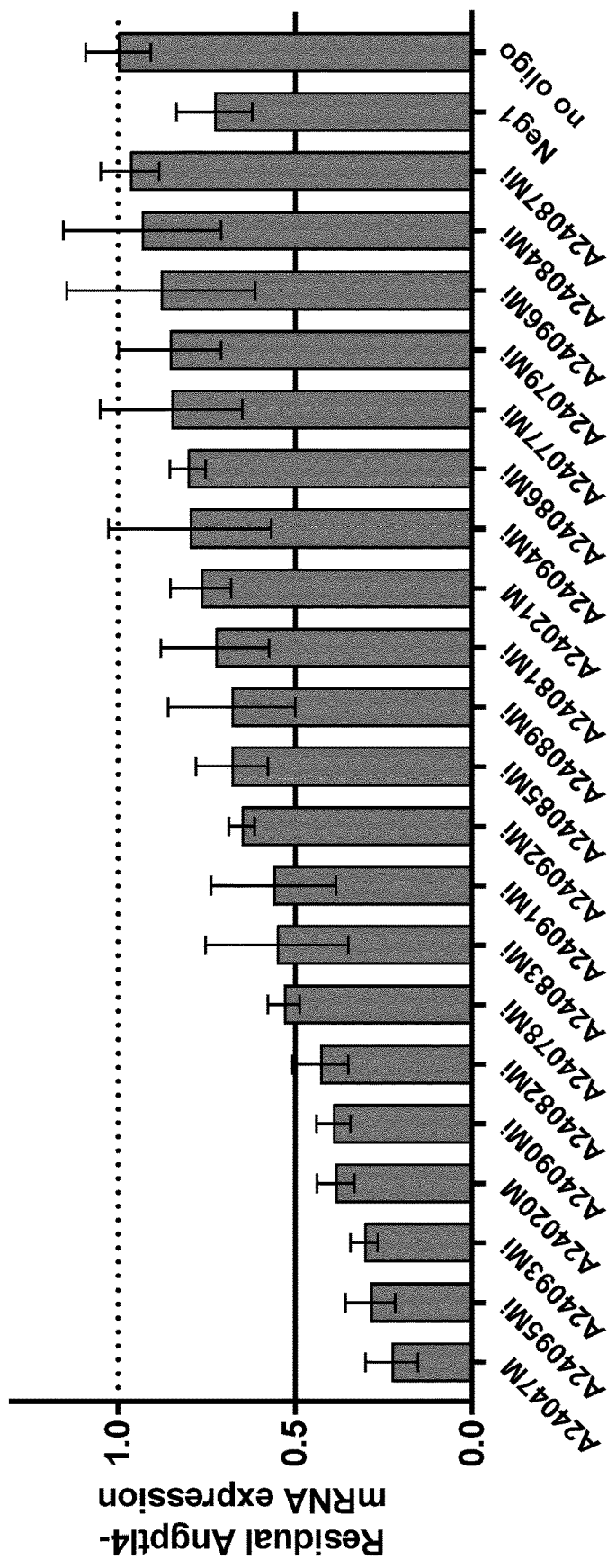
Fig. 15: Single-dose efficacy screen of intron-targeting mouse ANGPTL4-specific antisense oligonucleotides in 4T1 cells

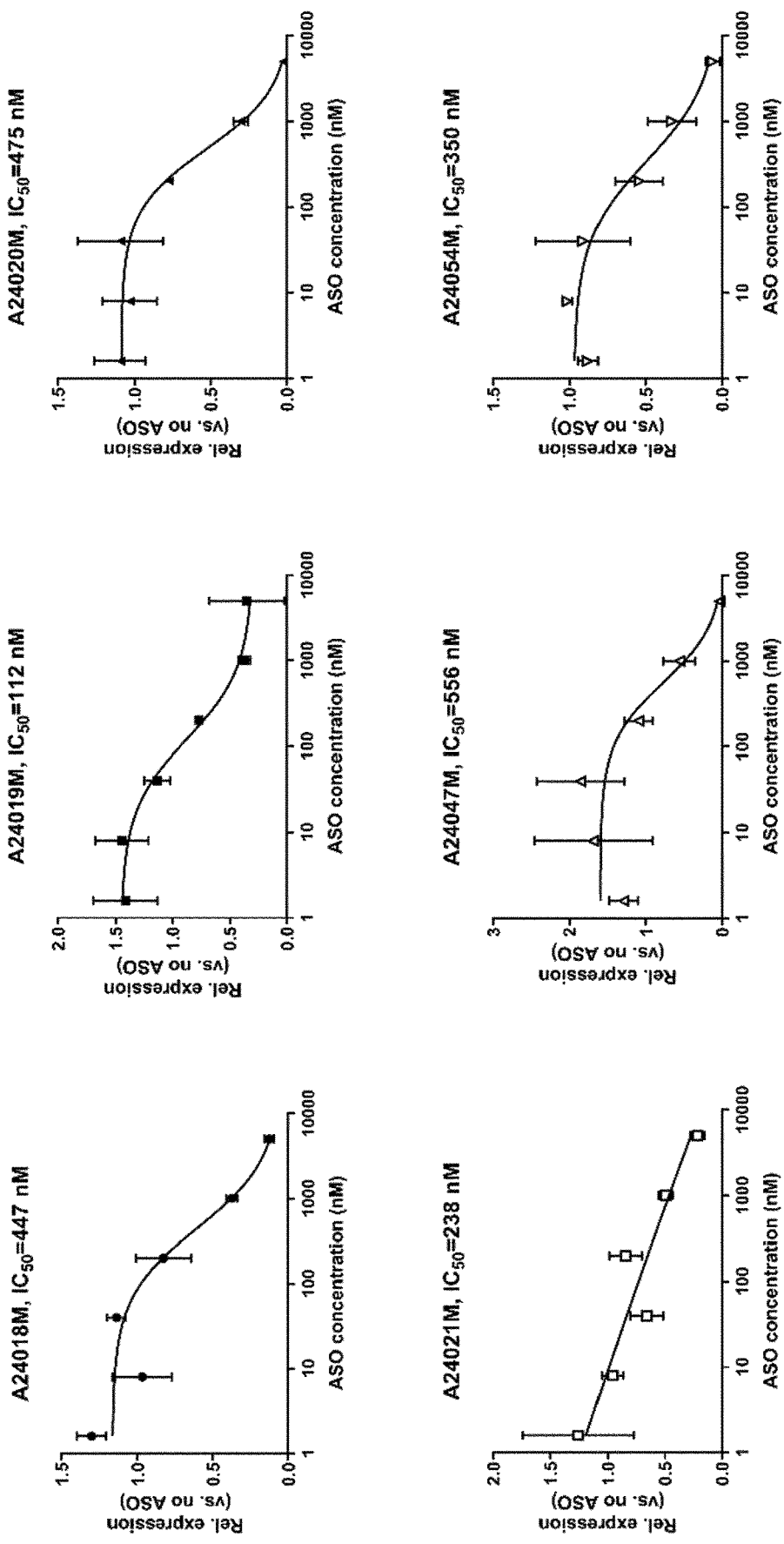
Fig. 16: IC$_{50}$ determination of selected mouse ANGPTL4-specific antisense oligonucleotides

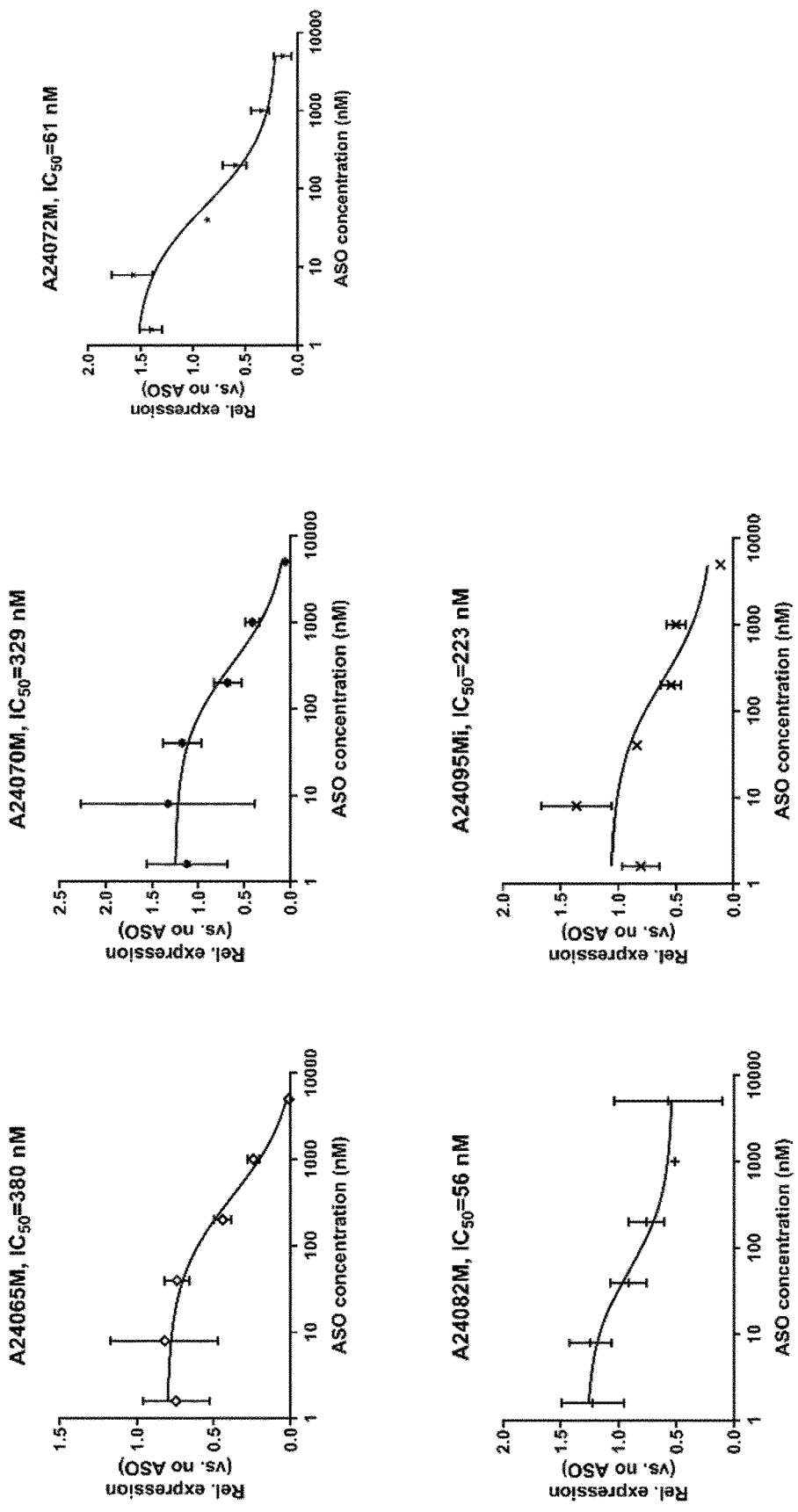
Fig. 16 (continued): IC$_{50}$ determination of selected mouse ANGPTL4-specific antisense oligonucleotides

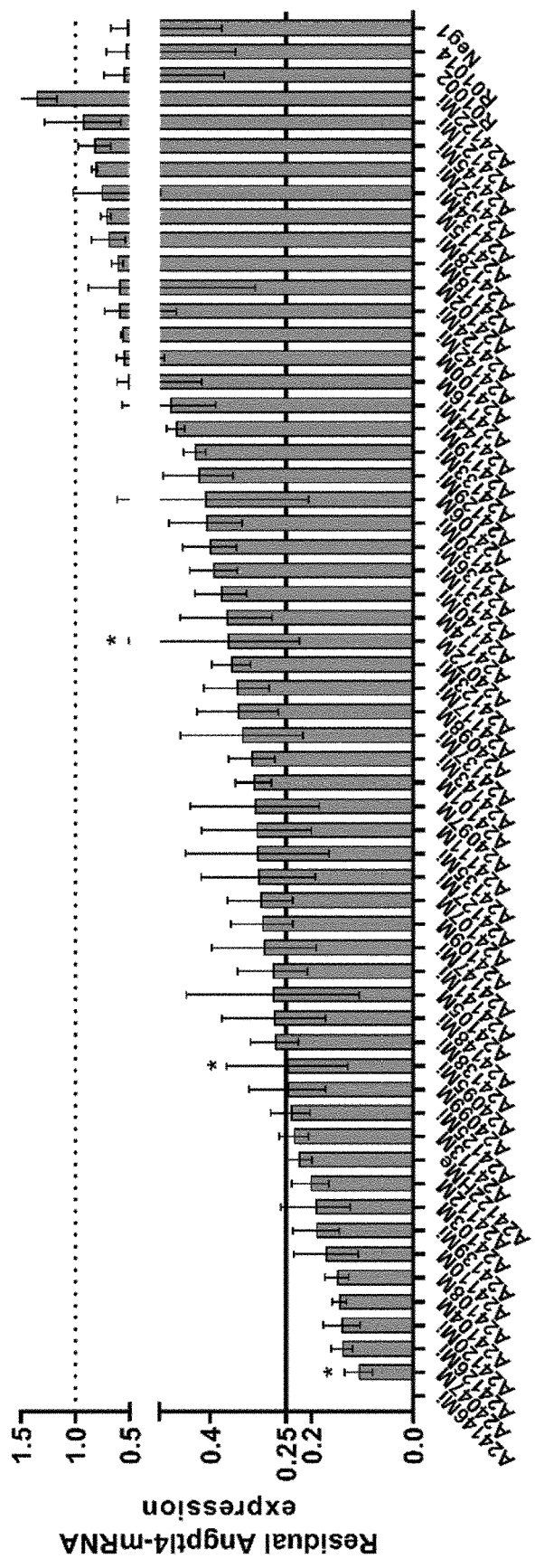
Fig. 17: 1st single dose efficacy screen of mouse Angptl4-specific ASOs in 4T1 cells

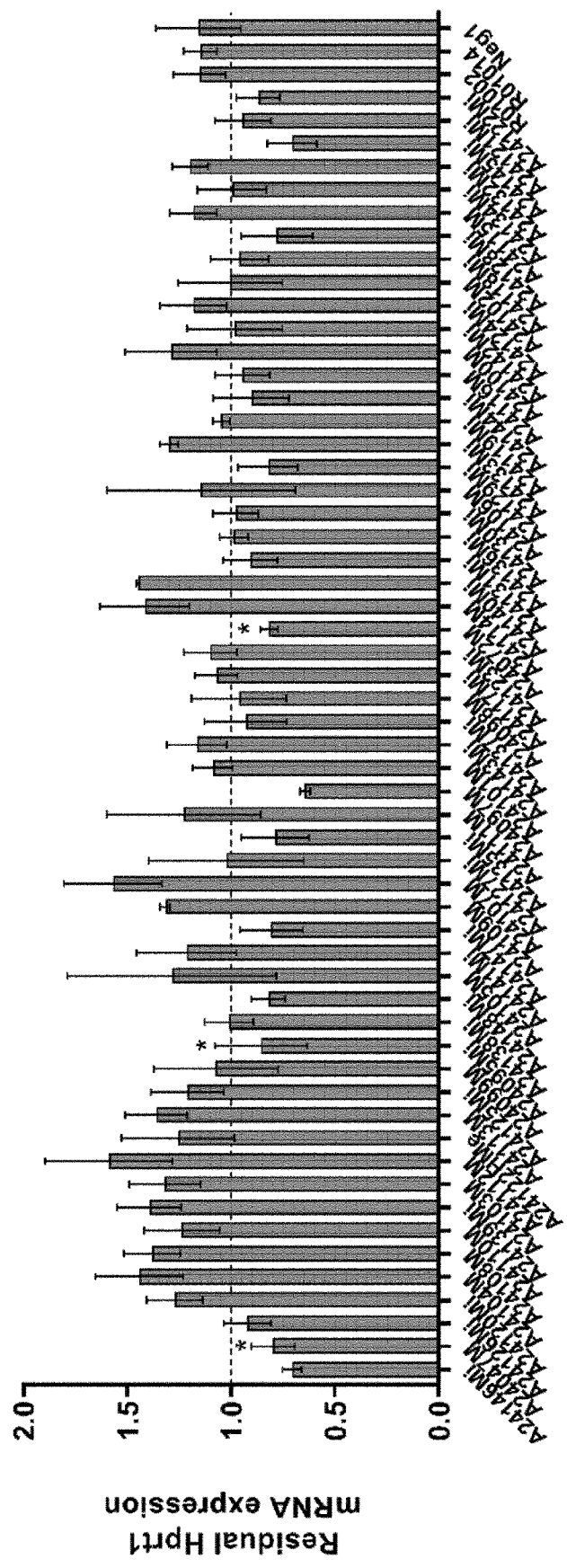
Fig. 17 (continued): 1st single dose efficacy screen of mouse Angptl4-specific ASOs in 4T1 cells

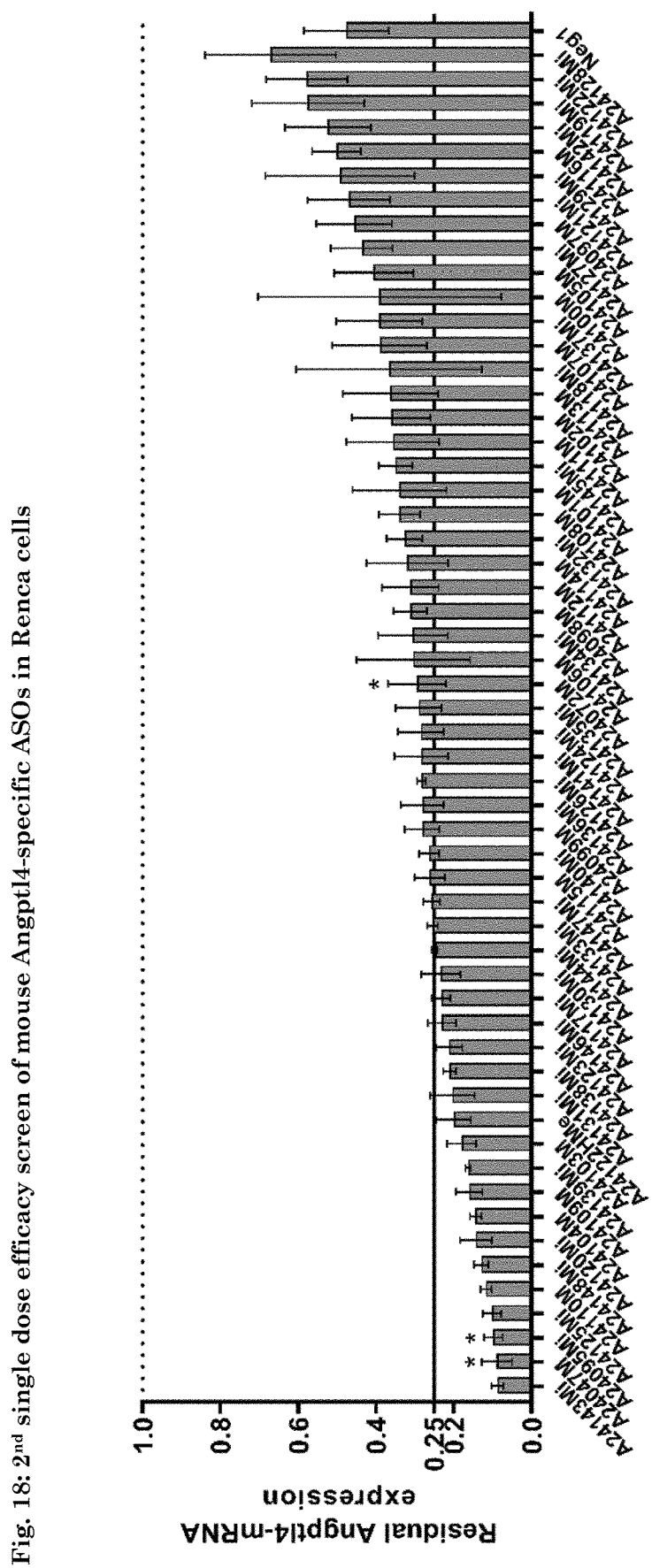
Fig. 18: 2nd single dose efficacy screen of mouse Angptl4-specific ASOs in Renca cells

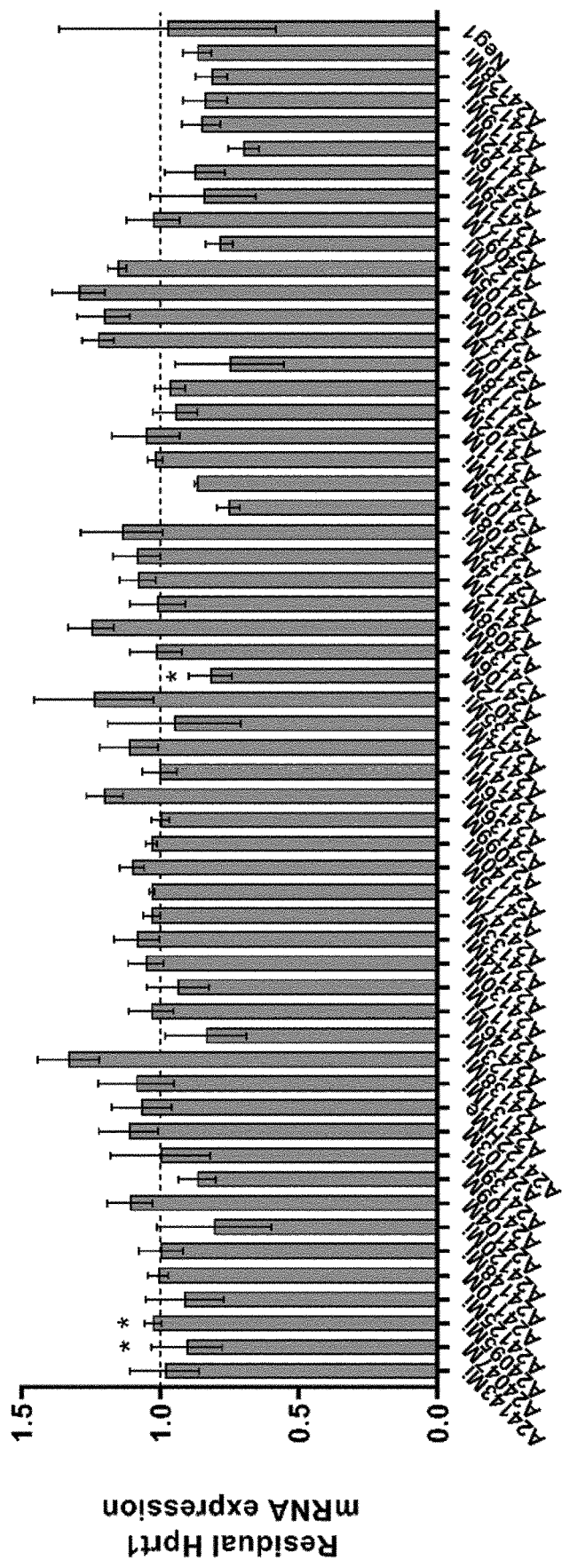
Fig. 18 (continued): 2nd single dose efficacy screen of mouse Angptl4-specific ASOs in Renca cells

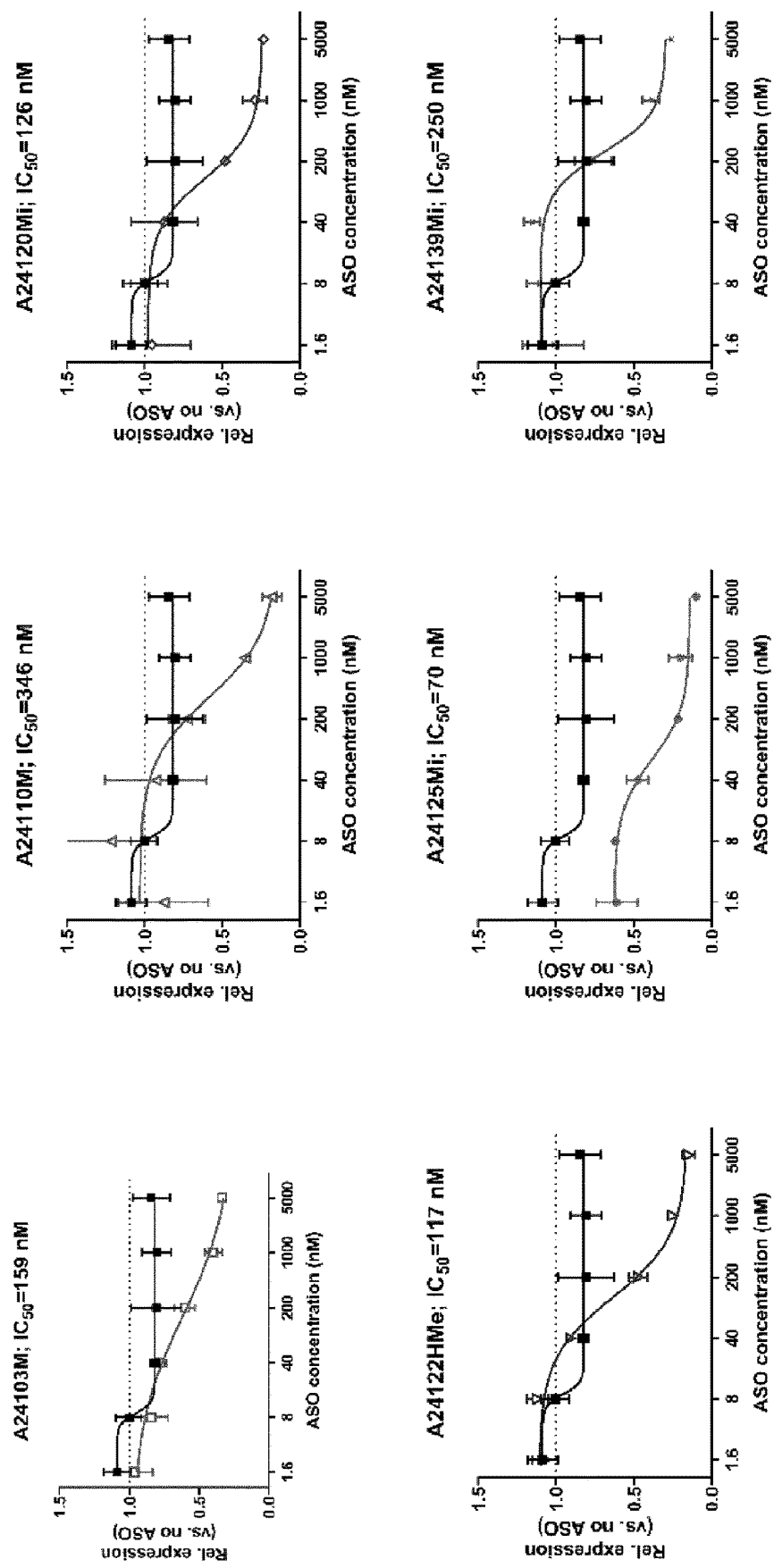
Fig. 19: IC$_{50}$ determination of selected mouse Angptl4 ASOs

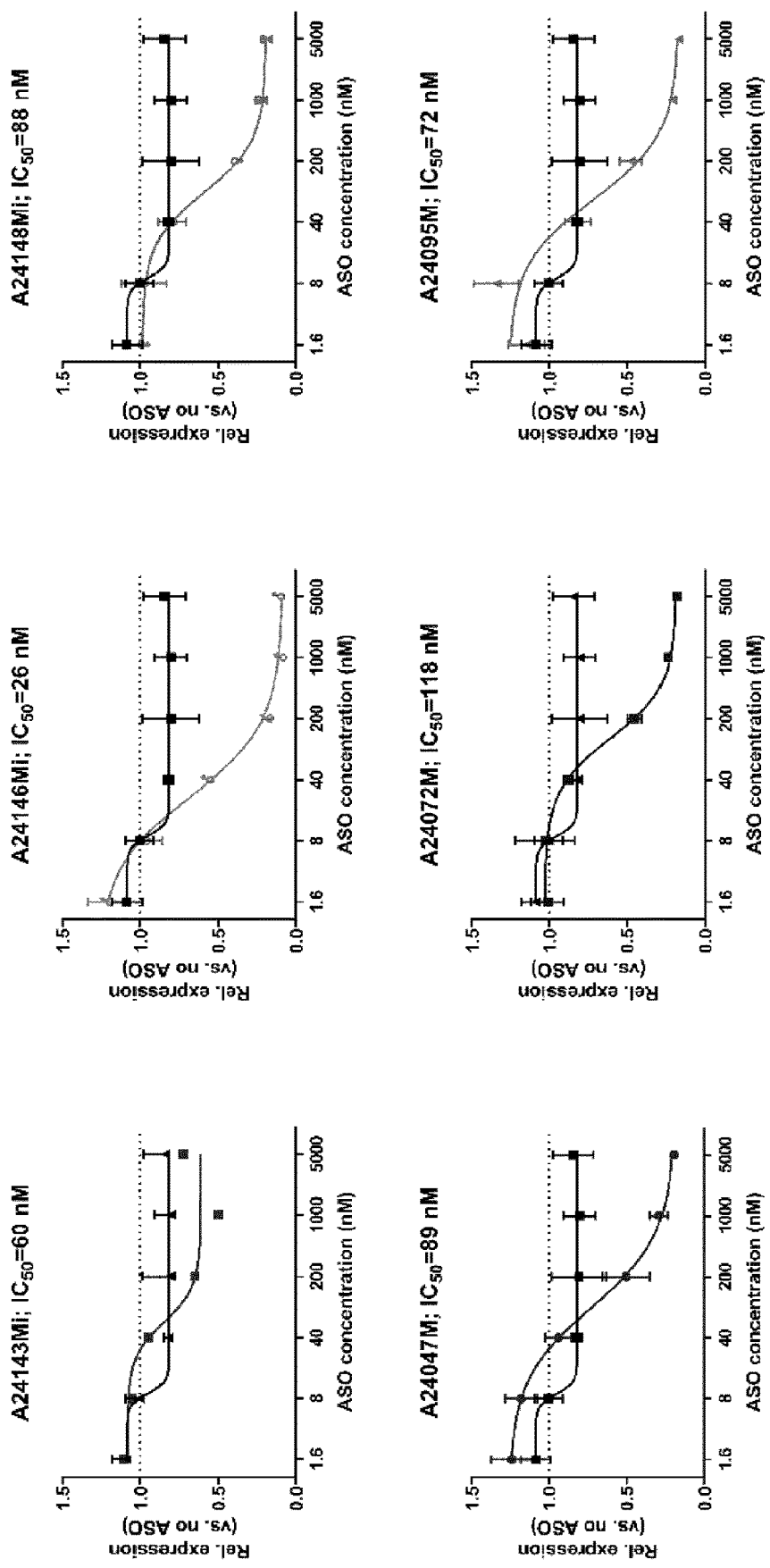
Fig. 19 (continued): IC$_{50}$ determination of selected mouse Angptl4 ASOs

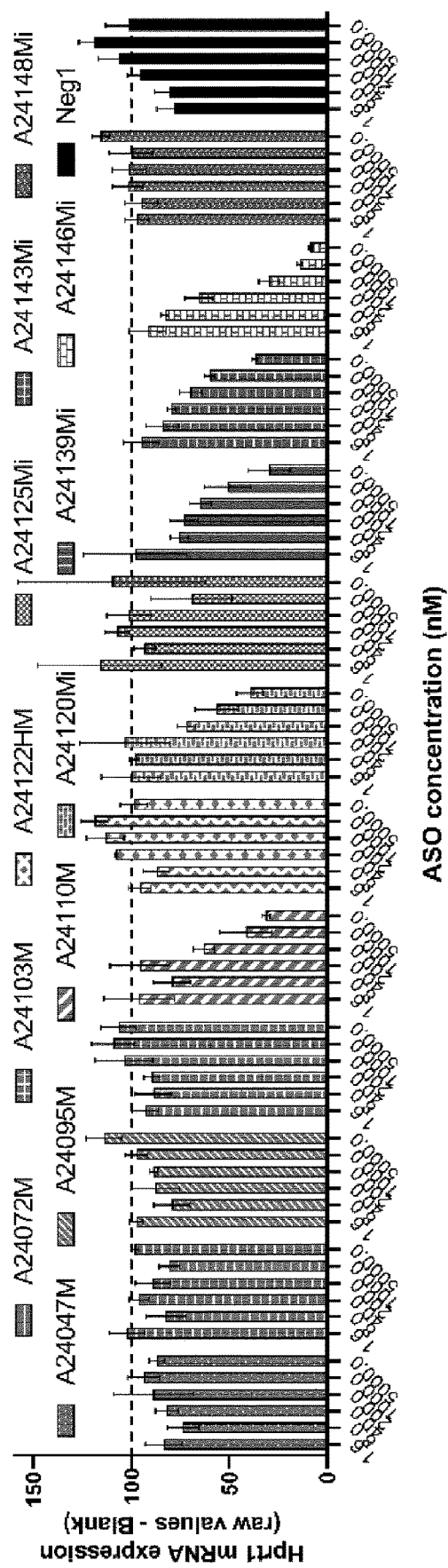
Fig. 19 (continued): IC$_{50}$ determination of selected mouse Angptl4 ASOs

SEQUENCE LISTING

```
<160> NUMBER OF SEQ ID NOS: 252

<210> SEQ ID NO 1
<211> LENGTH: 1905
<212> TYPE: DNA
<213> ORGANISM: Homo sapiens

<400> SEQUENCE: 1
ataaaaaccg tcctcgggcg cggcggggag aagccgagct gagcggatcc tcacacgact      60
gtgatccgat tctttccagc ggcttctgca accaagcggg tcttacccce ggtcctccgc     120 gtctccagtc ctcgcacctg aaccccaac gtccccgaga gtccccgaat cccgctccc       180 aggctaccta agaggatgag cggtgctccg acggccgggg cagccctgat gctctgcgcc    240
gccaccgccg tgctactgag cgctcagggc ggacccgtgc agtccaagtc gccgcgcttt   300
gcgtcctggg acgagatgaa tgtcctggcg cacggactcc tgcagctcgg ccaggggctg   360
cgcgaacacg cggagcgcac ccgcagtcag ctgagcgcgc tggagcggcg cctgagcgcg   420
tgcgggtccg cctgtcaggg aaccgagggg tccaccgacc tcccgttagc ccctgagagc   480
cgggtggacc ctgaggtcct tcacagcctg cagacacaac tcaaggctca gaacagcagg   540
atccagcaac tcttccacaa ggtggcccag cagcagcggc acctggagaa gcagcacctg  600
cgaattcagc atctgcaaag ccagtttggc ctcctggacc acaagcacct agaccatgag  660
gtggccaagc ctgcccgaag aaagaggctg cccgagatgg cccagccagt tgacccggct  720
cacaatgtca gccgcctgca ccggctgccc agggattgcc aggagctgtt ccaggttggg  780
gagaggcaga gtggactatt tgaaatccag cctcaggggt ctccgccatt tttggtgaac  840
tgcaagatga cctcagatgg aggctggaca gtaattcaga ggcgccacga tggctcagtg  900
gacttcaacc ggccctggga agcctacaag gcggggtttg gggatcccca cggcgagttc  960
tggctgggtc tggagaaggt gcatagcatc acgggggacc gcaacagccg cctggccgtg 1020
cagctgcggg actgggatgg caacgccgag ttgctgcagt tctccgtgca cctgggtggc 1080
gaggacacgg cctatagcct gcagctcact gcacccgtgg ccggccagct gggcgccacc 1140
accgtcccac ccagcggcct ctccgtaccc ttctccactt gggaccagga tcacgacctc 1200
cgcagggaca agaactgcgc caagagcctc tctggaggct ggtggtttgg cacctgcagc 1260
cattccaacc tcaacggcca gtacttccgc tccatcccac agcagcggca gaagcttaag 1320
aagggaatct tctggaagac ctggcggggc cgctactacc cgctgcaggc caccaccatg 1380
ttgatccagc ccatggcagc agaggcagcc tcctagcgtc ctggctgggc ctggtcccag 1440
gcccacgaaa gacggtgact cttggctctg cccgaggatg tggccgttcc ctgcctgggc 1500
aggggctcca aggaggggcc atctggaaac ttgtggacag agaagaagac cacgactgga 1560
gaagccccct ttctgagtgc aggggggctg catgcgttgc ctcctgagat cgaggctgca 1620
ggatatgctc agactctaga ggcgtggacc aagggggcatg gagcttcact ccttgctggc 1680
```

| | |
|---|---:|
| cagggagttg gggactcaga gggaccactt ggggccagcc agactggcct caatggcgga | 1740 |
| ctcagtcaca ttgactgacg gggaccaggg cttgtgtggg tcgagagcgc cctcatggtg | 1800 |
| ctggtgctgt tgtgtgtagg tccccctgggg acacaagcag gcgccaatgg tatctgggcg | 1860 |
| gagctcacag agttcttgga ataaaagcaa cctcagaaca ctttg | 1905 |

<210> SEQ ID NO 2
<211> LENGTH: 10223
<212> TYPE: DNA
<213> ORGANISM: Homo sapiens

<400> SEQUENCE: 2

| | |
|---|---:|
| ggggagaagc cgagctgagc ggatcctcac acgactgtga tccgattctt tccagcggct | 60 |
| tctgcaacca agcgggtctt accccggtc ctccgcgtct ccagtcctcg cacctggaac | 120 |
| cccaacgtcc ccgagagtcc ccgaatcccc gctcccaggc tacctaagag gatgagcggt | 180 |
| gctccgacgg ccggggcagc cctgatgctc tgcgccgcca ccgccgtgct actgagcgct | 240 |
| cagggcggac ccgtgcagtc caagtcgccg cgctttgcgt cctgggacga gatgaatgtc | 300 |
| ctggcgcacg gactcctgca gctcggccag gggctgcgcg aacacgcgga gcgcacccgc | 360 |
| agtcagctga gcgcgctgga gcggcgcctg agcgcgtgcg gtccgcctg tcagggaacc | 420 |
| gaggggtcca ccgacctccc gttagcccct gagagccggg tggaccctga ggtccttcac | 480 |
| agcctgcagg tacgtgtccc cagggctggt tctccgcgcc cctagtggct ctcctggctt | 540 |
| ggaagggtat ggacaggagt ggggcgtggg ggcggggtgc gcaactgtgg ctccctgggc | 600 |
| ttccctgcgt caagggatgg gctccccct taggaagccg aggagggagg ttcgctcaag | 660 |
| gccaggaatt caagaccacc taaagcaaaa tagcgagacc ccgtctctct ctacacacac | 720 |
| acacacacac acacaaaata aataaaataa aataaaataa atataaaatt aaaaaacgac | 780 |
| cgggcgcagt ggctcacgga gcctccacct gctgtcgaga ctagcctggc caacatggag | 840 |
| aaacctcgtc tctactaaaa atacaaaaaa ttagcctggc atggtgtgca tgcctgtaat | 900 |
| cccagctact tgggaggctg aggcaggaga atctcttgaa cccgggaggc agaggttgca | 960 |
| gtgagccgag atcgcagcac tgcactccag cctgggcaac agagtgagac tcctcaaaaa | 1020 |
| aataatagcg ataaaataaa aataaagcca ggtgcggtga ctcacgcttg tagtcccagc | 1080 |
| actttgggag ggcgaggcca gtggatcacc tgaggtcagg agttcaagac cagcctgacc | 1140 |
| aacacagtga aaccccgtct ctactaaaaa tacaaaaatt agctgggtgt ggtggtgggc | 1200 |
| gcctgtaatc ccagctactg ggaggctga ggcaggagaa cctcttgaac ccgggaggcg | 1260 |
| gaggttgcag tgagccggga tcatgccatt gcactccagc ctgggcgaca gagctcgact | 1320 |
| ccatctcaaa ataataataa taataaataa aataaaatac aaatacaaaa attagccagg | 1380 |
| tgtggtggca gctacttggg aggctgagac acaagaatca cttgagtctg ggaggcagag | 1440 |
| gttgcagtga gccaagattg cgccactgca ctccaacctg ggtgacagag cgagactctg | 1500 |
| tctgaaaaaa taaaaataa gccaggcata gagctgcatg actgtagtcc cagctacaca | 1560 |
| ggaggctgaa acaggagga tcgcctgacc ccaggagttg gaggctgcag tgagctgtga | 1620 |
| cagcaccact gcactccagc ctgggcgaga aacgagacc ccgtcattgg gaaaaaaag | 1680 |
| aaaaagaaa gactcccttg cctggcctca gcggatggag atttggaagg atggatgagt | 1740 |
| ggatgaatta agaggttggg gtaggcaagc tgggtcctca ccaaggtttt cacccctccc | 1800 |
| cagacacaac tcaaggctca gaacagcagg atccagcaac tcttccacaa ggtggcccag | 1860 |
| cagcagcggc acctggagaa gcagcacctg cgaattcagc atctgcaaag ccaggtaacc | 1920 |

```
ctaggatcaa gggagaaaag gtccctctga tagctggacc ccaggttgag agggaggtgg    1980
tgagaactgg acgtgtggct ggggacgtgg ggccaggcag gacctgacac cctcctcccg    2040
tcccatccta gtttggcctc ctggaccaca agcacctaga ccatgaggtg gccaagcctg    2100
cccgaagaaa gaggctgccc gagatggccc agccagttga cccggctcac aatgtcagcc    2160
gcctgcaccg tgagtgtctg cccctcgatg ctctccggtg gccaccccta ccccgccact    2220
tgccattgct ggtcctctcc ttgtcaggtc caccttaagg agaagatgtc ctggcctgga    2280
gtccctgagg gctcaccagt ctctgggtca aagctgatgg gagcacctcc ttcctcagcc    2340
ctgacctggc ccagccaggc cacccaaccc ttctcctctg caagccagtg ggctgtccct    2400
gaagccctgc tgatcactga ttggaacaga ggtggagaaa gaggtcttga gggacttgag    2460
ctgcaggggt gctggagaag gtagaaatgg ggttcggggt gccatcctga aggttagaac    2520
cttctagggg agggtgtcat ggaggagggg gtgccaggta gtagtgtttg tagatttggg    2580
ccctccacaa tgtcttgggg tatgtgggaa ttagggctgg gaaccccccag ctcccagacc    2640 agaaacactc ttgtatctta caaatccaat gctccaggtc cctgacccct cttcctcctt    2700
cctctcttgt tctcctcctc cctccccgcc ccgccggcc ccctcccccac cgcagaaagt    2760 gggcttttgc tgccaccaca agttgtaggt gctttattcc caaatctccg ttcatctcga    2820
accacagcat gtcacgtgt gtccgatgca gactcgcggt tctctaagtt cacgccccca    2880
cacggtttct ctgtggtcct catccttccc tgcatctgtg gctgtccaca gccaactggg    2940
tgaaagtttg gatcccccctc tcacacccta gggtcagtgg caggcttcca gcactgtaga    3000
cctgagggtt ctctcctccc caagctcccg ctccttccca cctccgtgct gcccgccccc    3060
aaccccgcca ggctagcatc tcagcgtggt cagggtcctg tccaccctcc caaagccacc    3120
atcccaggat gaggggcttc tggagggtga cggggaagg cacaagtcct ggctgggaaa    3180
tgcggtggaa gggggcaggg gttcgtgggg ttcgggactc ccagactctt ggctcaggcc    3240
cgccaagtag gagaaagttc agagctggga aggcgaacag ctggcattca tggaagccac    3300
actggtggtt tggccgcgtg cccatcctta ctggatggga ggaaagtagg ggaaagggga    3360
gatgcctgag gggccggaaa gcgtcttcct ggtcactctg ggcccgcccc cacccccacc    3420
gtgcagactc atttcgacct ttcccctact tttccggctg ggctgggggc ggttcctccc    3480
agtctggagc gtctgagcct ccagacgtgc tcaacgccat cctcccctcc tccctccctc    3540
tttctttcct caaccctgcc tcctctccct ctaggagctg ggaccccagg cagagcctct    3600
gagatgctcc tgctcagcac agttcttccc gttctgacc tgctgcctca ttcattcatt    3660
cattcattca tttgtcaaga ctgttttgtt tgcttttgaa gacggagtct cgctctgttg    3720
tccaggctga agtgcagtgg cgcaatctca gctcactgca acctctgcct cccactgggt    3780
tcaagtgatt ctcctgcctc agcctctcaa gtagatggga ttataggcgc ctaccgccac    3840
cacgcccagc taattttttat tcatttatca agtctttttt ttttttgaga cagagtctca    3900
ctctgtcacc caggttggag tgcaatggtt caacctcagc tgactgcaac ctctgcctcc    3960
cgggttcaag tgattctcct gcctctgcct cctaaggagc tgggattact ggcgtccacc    4020
atcacaccca gctaatcttt gtatgtttta ctagagatgg gtttggcca tgttgaccag    4080 gctggtctca aactcctgac cgatccgccc gcctcccaaa gtgctggatt acaggcatga    4140
accactgcgc ccgcccatt cctcaagtct ttattgagca gctgctatgc gctgggcct    4200 gcgtggatgc tggtgccagg ctgtgggcag agctgctcct tgtccccagc ctcatggagc    4260
```

```
ctccattgag tcagaggaga gaccattaga tgacctcagt gtccaggagt gggaagtcct      4320
tgctcaattc ccatttgggg tgttctggcc tggtctgggg gtgaggcaag cagggtgtc      4380 cttccagaag ctgggaccca gagagagaag tgaggaaaga gagtcccgcc gggcgcagtg      4440
gttcacacct gtaatcccag cactttggga ggccaaggct ggcggatcac gaggtcagga      4500
gatcgagacc agtctggcca acatggtgaa accccgtct ctacaaataa tgcaaaaact      4560
agtcgggcgt ggtggcacat gcctgtagtc ccagctgctc cggaggctgc ggcagaattg      4620
cttgaacctg ggaggcggag gttgcagtga gccaagattg cgccactgca ctccagcctg      4680
gcgacagagc gagactccgt atcaaaaaac aaaacaaaaa aagagagtcc caggcagggg      4740
gaacagcatg tgcaaagtcc ctgtggcagg acggtgtgtg gtacaagggt gggaagaaag      4800
cctgtgtgcc agagagggtg tgggtacagc atggcaggag gaggatgggc acggggctg       4860 gtcctccagg tgccttgtgg accatgctga ggaaggacat agggagccat ggaagaggtt      4920
aggcagatgg cagagaggtg gtcatgagat aagatttgcc ttttacttcc ctggtcatcc      4980
actgttaagc cccagatat gcctggctcc tgagacccc cccagggct gccctcctgt          5040 ttcaagtctc cactttatct cccttcaggg ctgcccaggg attgccagga gctgttccag      5100
gttggggaga ggcagagtgg actatttgaa atccagcctc aggggtctcc gccattttg       5160 gtgaactgca agatgacctc aggtaggtg tgttagtcca ccaggggccc ctctccccat       5220
aggccctgtt gtctttcttt aaattgaaaa caaaacaaaa caaaaaaatt aaaggcaggg      5280
tcttgctatg ttgcccaagc tggtcttttt tttttttttt tttttgaga tggagttttg       5340 ctcttggagc tggagtgcaa tgccacgatc tcagctcact gaaacctccg cctcccgggt      5400
tcaagcaatt ctccagcgtc agcctcccca gtagctgaga ctacaggtgc gagcaaccac      5460
acccagctaa ttttttgtatt tttagtagag actgggtttc accatgttgg tctggctggt     5520
ctcaaactcc tgacctcaaa tgatttgccg actttggcct cccaaaatgc tgggattata     5580
ggcattagcc actgctcctg gcctcttttc tttaaaatgc agcccttgtc tgggtgtagt      5640
ggctcatatc tgtaatcccg cactttggg aggcctatca tgaggatcac ttgagcccag       5700
aagttcgaga ccagcctgga caacatagtg agagctcatc tttacaaaaa attttgtaaa      5760
agtaaaaaaa aaggccaagt gcagtggctc acacctgtaa tcccagcact tgggaggtt       5820 gaggcagaca gatcacgagg tcaggagttc gagaccagcc tgaccaacat ggtgaaaccc     5880
cgtctctact aaaaatacaa aaattagccg ggcatggtgg tgtgcacctg taatcccagc     5940
tactcaggtg gctgaggcag gagaatctct tgaacctggg aggcagaggt tgcagtgagc     6000
tgagatgacg ccaccgcact ccagcctggg cgacagagcg agactccgtc ccccatcaa      6060 aaaaataaaa aagagaaaat aaaataaaat aaaataaaat tcagcccttg ctgggcatgg      6120
tggcacatgc ctgtagtccc agctactcgg gaggccaagg caggagggtc acttcagccc     6180
aggagttaaa ggctgccgtg agccgtgatc acacctgtga atagccaccg cactccaacc     6240
tgggcaacac aacaaaacct cgtttctaaa aaaaacaaa ggctgagcac ggtggcttac       6300
acctgaaatg ccagcacttt ggaggctga ggcgggcaaa tcacttgagg tcagaagttc       6360
aagaccagcc tggccaacat ggtgaaaccc tatctctacc aacataaaca ttagccgggc     6420
gtgcctgtga ttccagctgc ttgtgggct gaagcacaag aatcgcttga gccccgaagg      6480
cagaggttgc agtgagctga gattgcggca ctgcgatcca gcctgggcaa cagagtgaga     6540
ctccatctct aaaaaaaaa aaaaaaaaa agaaagcttt ttttttccact gagaagtcct       6600 ttccattaca agaggttaca acacgggtt ttacccagtt cagctggccc agagaggctt      6660
```

```
tgcagatttc cactgcctac tccctcccac actcagtccc tgctgggttc ttgggacaaa    6720
gatcttccca aggccagccc ataatattcc tccctctgac ccaccctcct cgagtcctcc    6780
agggatgagt gagggagctg ctgtcttcct gggtttggag ggggtttggt gcttggcagc    6840
cagatgaggg agtgggtcg tctgtgaaga gggacttcct ggtgaccttg tacctttctg     6900
ggcagatgga ggctggacag taattcagag gcgccacgat ggctcagtgg acttcaaccg    6960
gccctgggaa gcctacaagg cggggtttgg ggatccccac ggtaggtgtt tctagtgggg    7020
acagaggcag gggaggaaga gggaccctca gaagtggccc tgcctcatgg agtggcctct    7080
cccactccag gcgagttctg gctgggtctg gagaaggtgc atagcatcac ggggaccgc     7140 aacagccgcc tggccgtgca gctgcgggac tgggatggca acgccgagtt gctgcagttc    7200
tccgtgcacc tgggtggcga ggacacggcc tatagcctgc agctcactgc acccgtggcc    7260
ggccagctgg gcgccaccac cgtcccaccc agcggcctct ccgtacccttc tccacttgg    7320 gaccaggatc acgacctccg cagggacaag aactgcgcca agagcctctc tggtgagcag    7380
gccctgccat gccacaccca gccagcagct ccctcctta tctttctgct gctctgtcct    7440
gccttcaacc ccacattgca tctgtttcct gcccccacct cttccttaca tgccgtgtgt    7500
gtgattgggc cactaactta gcctatctgg cctcagtttt cccatcctga aaagggtctt    7560
gaccgtcttt acttttattt acttatgtgt ttgtttattt atttatttat gtatttattt    7620
tttgagacgg agtctcactt tgtcacccag gctggagtgc tttgtggcac gatcttggct    7680
cactgcaagc tccacctcct gagttcacac cattctcctg cctcagcctc ccgagtagct    7740
gggactatag gtgcccacca ccacgcctgg ctaatttttt tgtatttta gtagagatgg    7800 ggtttcaccg tgttagccag gatggtctcg atctcctgac ctcgtgatct gcctgcctca    7860
gcctcccaaa gtgctgggat tacaggcgtg agccaccgcg cccggcctac ttatttattt    7920
tttgagacag agtcccgctg tgtctcccag gctggagtgc aagtgacgtg atcttggctc    7980
actgcagcct ccgcctcctg ggttcaagtg attctcctgc ctcagcctcc tgagtagctg    8040
ggattacagg ttcccgccac catgcacaga taattgtttt gtattttag tagagacggg     8100 gtttcaccat gttggccagg gtggtcttga actcctgacc tcaagtgatc tgcccacctc    8160
ggcctcccaa agtgttggga ttacaggcgt gagccacaat acccggccac aaacatcttt    8220
ataatggtgc tccacaggat tctttttttt ttttttttt tgaaacaggg tctcactctg    8280
ttgcctaagc tggagtgcag tggtgcgatc tcggctcact gcaacctcca cctcccgggt    8340
tcaagcaatt ctcaaaaaaa aaaaaaatt aggcacggtg gctcacactt gcaatcccag    8400
cactttggga ggctgaagcg agtggatcac ttgagcccag gagaccaatc tgagcaacag    8460
ggcgaaatcc tgtctcaatt aaaaatacaa aaaactagct gggcatggtg gtgcctgcct    8520
gtgttcccat ctacttggga ggctgagttg ggaggatctc ttgagcctag gagataaggc    8580
tgcagtgagc tgagactgcg ccactgcact caagcctggg tgacagagtg agaccctgc     8640 ctcaaaagaa aaagaaaaaa tgcaggcatg gtggctcaca cctgtggtcc cagctacttg    8700
ggaggcccag gtacaagaat cacttgagcc cgtaaggttg acgctgcatt gagccatcac    8760
cacaccactg cactccagcc tgggcaatgg agccaggccc tgtctcaaaa aaaattgttt    8820
ttaaacttaa aaataaggcc gggtgtgggg gctcacacct gtaatcccag cactttggga    8880
ggccgaggtg ggtggatcac ctgaggtcag gagttcaaaa ctagcctggc caacatggtg    8940
aaaccctgtc tctactaaaa atacaaaaat taggccaggc gcagtgggtc atacctgtaa    9000
```

-continued

```
tcccagcact ttgggaggct gaggagggtg gatcacatga ggtaaggagt ttgagaccaa    9060
cctggccaac atggtgaaac cccctcacta ctaaaaatac aaaaactagc caggcgtggt    9120
ggcgggtgcc tgtaatcccg gctactcagg aggctgaggc atgagaatcc cttgaacctg    9180
ggaggcagag gtgcagtgag ccgagattgt gccactgcac tccagcctgg gagatagagt    9240
gagactcagt ctcaaaaaaa aagaccaaaa attagccagg tgtggtggca ggcgcctgta    9300
atcccagcta ctcgggaggc tgagggagga gaatcactta aacctgagag acggaggttg    9360
cagtgagctg agatcgcacc actgcactcc agcctgggtg acagagtaag actcaatctc    9420
aaaaaaaaaa aagtcaagtc caaagccagc cctggtcccc aacctgcctc atcctcaacc    9480
ctatccctat ctcctttcag ccccatcggt ggctcaaaga cctgaccatg ttccctctcc    9540
cctgaccccg gcaggaggct ggtggtttgg cacctgcagc cattccaacc tcaacggcca    9600
gtacttccgc tccatcccac agcagcggca gaagcttaag aagggaatct tctggaagac    9660 ctggcgggc cgctactacc cgctgcaggc caccaccatg ttgatccagc ccatggcagc    9720
agaggcagcc tcctagcgtc ctggctgggc ctggtcccag gccacgaaa gacggtgact    9780 cttggctctg cccgaggatg tggccgttcc ctgcctgggc aggggctcca aggaggggcc    9840
atctggaaac ttgtgcacag agaagaagac cacgactgga gaagcccct ttctgagtgc    9900 agggggctg catgcgttgc ctcctgagat cgaggctgca ggatatgctc agactctaga    9960
ggcgtggacc aagggcatg gagcttcact ccttgctggc cagggagttg gggactcaga   10020 ggaccactt ggggccagcc agactggcct caatggcgga ctcagtcaca ttgactgacg   10080
gggaccaggg cttgtgtggg tcgagagcgc cctcatggtg ctggtgctgt tgtgtgtagg   10140 tccctgggg acacaagcag gcgccaatgg tatctgggcg gagctcacag agttcttgga   10200 ataaagcaa cctcagaaca ctt                                            10223
```

<210> SEQ ID NO 3
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 3
aggctaagtt agtggcc                                                      17

<210> SEQ ID NO 4
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 4
gccagatagg ctaagtt                                                      17

<210> SEQ ID NO 5
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 5
ctggaaagaa tcggatc					17

<210> SEQ ID NO 6
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 6
cgctggaaag aatcgga					17

<210> SEQ ID NO 7
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 7
gctagtctcg acagcag					17

<210> SEQ ID NO 8
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 8
gatcctcatg ataggcc					17

<210> SEQ ID NO 9
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 9
ggccgtcgga gcaccgc					17

<210> SEQ ID NO 10
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 10
catgctgtgg ttcgaga					17

<210> SEQ ID NO 11
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 11
cgtgcgccag gacattc					17

```
<210> SEQ ID NO 12
<211> LENGTH: 16
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 12
cgtgcgccag gacatt                                                      16

<210> SEQ ID NO 13
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 13
tccgtgcgcc aggacat                                                     17

<210> SEQ ID NO 14
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 14
ggagtccgtg cgccagg                                                     17

<210> SEQ ID NO 15
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 15
tgcgctccgc gtgttcg                                                     17

<210> SEQ ID NO 16
<211> LENGTH: 16
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 16
tgcgctccgc gtgttc                                                      16

<210> SEQ ID NO 17
<211> LENGTH: 16
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 17
gtgcgctccg cgtgtt                                                      16
```

<210> SEQ ID NO 18
<211> LENGTH: 17
<212> TYPE: DNA
<213> ORGANISM: Artificial Sequence
<220> FEATURE:
<223> OTHER INFORMATION: antisense oligonucleotides hybridizing with human ANGPLT4

<400> SEQUENCE: 18
gtcgaaatga gtctgca                                                17

<210> SEQ ID NO 19
<211> LENGTH: 17
<212> TYPE: DNA
<213> ORGANISM: Artificial Sequence
<220> FEATURE:
<223> OTHER INFORMATION: antisense oligonucleotides hybridizing with human ANGPLT4

<400> SEQUENCE: 19
gcacgtctgg aggctca                                                17

<210> SEQ ID NO 20
<211> LENGTH: 17
<212> TYPE: DNA
<213> ORGANISM: Artificial Sequence
<220> FEATURE:
<223> OTHER INFORMATION: antisense oligonucleotides hybridizing with human ANGPLT4

<400> SEQUENCE: 20
ttgagcacgt ctggagg                                                17

<210> SEQ ID NO 21
<211> LENGTH: 17
<212> TYPE: DNA
<213> ORGANISM: Artificial Sequence
<220> FEATURE:
<223> OTHER INFORMATION: antisense oligonucleotides hybridizing with human ANGPLT4

<400> SEQUENCE: 21
ggatcgcagt gccgcaa                                                17

<210> SEQ ID NO 22
<211> LENGTH: 14
<212> TYPE: DNA
<213> ORGANISM: Artificial Sequence
<220> FEATURE:
<223> OTHER INFORMATION: non sense artificical sequence

<400> SEQUENCE: 22
aaaaaaaaaa aaaa                                                   14

<210> SEQ ID NO 23
<211> LENGTH: 17
<212> TYPE: DNA
<213> ORGANISM: Artificial Sequence
<220> FEATURE:
<223> OTHER INFORMATION: antisense oligonucleotides hybridizing with human ANGPLT4

<400> SEQUENCE: 23
gctgaattcg caggtgc                                                17

<210> SEQ ID NO 24

```
<211> LENGTH: 16
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 24
gatcgcagtg ccgcaa                                                    16

<210> SEQ ID NO 25
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 25
gtgttgtaac ctcttgt                                                   17

<210> SEQ ID NO 26
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 26
ccgtgttgta acctctt                                                   17

<210> SEQ ID NO 27
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 27
cctcatggtc taggtgc                                                   17

<210> SEQ ID NO 28
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 28
cacctcatgg tctaggt                                                   17

<210> SEQ ID NO 29
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 29
ggcgcctctg aattact                                                   17

<210> SEQ ID NO 30
<211> LENGTH: 17
```

```
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 30
cgtggcgcct ctgaatt                                                    17

<210> SEQ ID NO 31
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 31
tcgtggcgcc tctgaat                                                    17

<210> SEQ ID NO 32
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 32
ccgccttgta ggcttcc                                                    17

<210> SEQ ID NO 33
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 33
actcggcgtt gccatcc                                                    17

<210> SEQ ID NO 34
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 34
gccgtgtcct cgccacc                                                    17

<210> SEQ ID NO 35
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 35
gaggtcgtga tcctggt                                                    17

<210> SEQ ID NO 36
<211> LENGTH: 17
<212> TYPE: DNA
```

<213> ORGANISM: Artificial Sequence
<220> FEATURE:
<223> OTHER INFORMATION: antisense oligonucleotides hybridizing with human ANGPLT4

<400> SEQUENCE: 36
gcggaggtcg tgatcct                                                          17

<210> SEQ ID NO 37
<211> LENGTH: 17
<212> TYPE: DNA
<213> ORGANISM: Artificial Sequence
<220> FEATURE:
<223> OTHER INFORMATION: antisense oligonucleotides hybridizing with human ANGPLT4

<400> SEQUENCE: 37
cctgcggagg tcgtgat                                                          17

<210> SEQ ID NO 38
<211> LENGTH: 17
<212> TYPE: DNA
<213> ORGANISM: Artificial Sequence
<220> FEATURE:
<223> OTHER INFORMATION: antisense oligonucleotides hybridizing with human ANGPLT4

<400> SEQUENCE: 38
ctcttggcgc agttctt                                                          17

<210> SEQ ID NO 39
<211> LENGTH: 17
<212> TYPE: DNA
<213> ORGANISM: Artificial Sequence
<220> FEATURE:
<223> OTHER INFORMATION: antisense oligonucleotides hybridizing with human ANGPLT4

<400> SEQUENCE: 39
gctcttggcg cagttct                                                          17

<210> SEQ ID NO 40
<211> LENGTH: 17
<212> TYPE: DNA
<213> ORGANISM: Artificial Sequence
<220> FEATURE:
<223> OTHER INFORMATION: antisense oligonucleotides hybridizing with human ANGPLT4

<400> SEQUENCE: 40
ggctcttggc gcagttc                                                          17

<210> SEQ ID NO 41
<211> LENGTH: 17
<212> TYPE: DNA
<213> ORGANISM: Artificial Sequence
<220> FEATURE:
<223> OTHER INFORMATION: antisense oligonucleotides hybridizing with human ANGPLT4

<400> SEQUENCE: 41
ggtgccaaac caccagc                                                          17

<210> SEQ ID NO 42
<211> LENGTH: 17
<212> TYPE: DNA
<213> ORGANISM: Artificial Sequence

```
<220> FEATURE:
<223> OTHER INFORMATION: antisense oligonucleotides hybridizing with
      human ANGPLT4

<400> SEQUENCE: 42
ggagcggaag tactggc                                                      17

<210> SEQ ID NO 43
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 43
atggagcgga agtactg                                                      17

<210> SEQ ID NO 44
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 44
ggatggagcg gaagtac                                                      17

<210> SEQ ID NO 45
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 45
ggctggatca acatggt                                                      17

<210> SEQ ID NO 46
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 46
atgtgactga gtccgcc                                                      17

<210> SEQ ID NO 47
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 47
caatgtgact gagtccg                                                      17

<210> SEQ ID NO 48
<211> LENGTH: 17
<212> TYPE: DNA
<213> ORGANISM: Artificial Sequence
<220> FEATURE:
```

```
<223> OTHER INFORMATION: antisense oligonucleotides hybridizing with
      human ANGPLT4

<400> SEQUENCE: 48
gaactctgtg agctccg                                                   17

<210> SEQ ID NO 49
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 49
ctggtggact aacacac                                                   17

<210> SEQ ID NO 50
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 50
tggacctgac aaggaga                                                   17

<210> SEQ ID NO 51
<211> LENGTH: 16
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 51
cacacggcat gtaagg                                                    16

<210> SEQ ID NO 52
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 52
aggctagtct cgacagc                                                   17

<210> SEQ ID NO 53
<211> LENGTH: 17
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 53
gatcgcagtg ccgcaat                                                   17

<210> SEQ ID NO 54
<211> LENGTH: 17
<212> TYPE: DNA
<213> ORGANISM: Artificial Sequence
<220> FEATURE:
<223> OTHER INFORMATION: antisense oligonucleotides hybridizing with
``` human ANGPLT4

<400> SEQUENCE: 54
cgtgttgtaa cctcttg                                                    17

<210> SEQ ID NO 55
<211> LENGTH: 15
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 55
gatcgcagtg ccgca                                                      15

<210> SEQ ID NO 56
<211> LENGTH: 15
<212> TYPE: DNA
<213> ORGANISM: Artificial Sequence
<220> FEATURE:
<223> OTHER INFORMATION: antisense oligonucleotides hybridizing with
      human ANGPLT4

<400> SEQUENCE: 56
ggatcgcagt gccgc                                                      15

<210> SEQ ID NO 57
<211> LENGTH: 18
<212> TYPE: DNA
<213> ORGANISM: Artificial Sequence
<220> FEATURE:
<223> OTHER INFORMATION: oligonucleotide negative control
<220> FEATURE:
<221> NAME/KEY: modified_base
<222> LOCATION: (1)..(17)
<223> OTHER INFORMATION: nucleotide may be modified with
      phosphorothioate (PTO)
<220> FEATURE:
<221> NAME/KEY: modified_base
<222> LOCATION: (1)..(3)
<223> OTHER INFORMATION: nucleotide may be modified as locked nucleic
      acid (LNA)
<220> FEATURE:
<221> NAME/KEY: modified_base
<222> LOCATION: (15)..(17)
<223> OTHER INFORMATION: nucleotide may be modified as locked nucleic
      acid (LNA)

<400> SEQUENCE: 57
cgtttaggct atgtactt                                                   18

<210> SEQ ID NO 58
<211> LENGTH: 1916
<212> TYPE: DNA
<213> ORGANISM: Mus musculus

<400> SEQUENCE: 58
gctttataaa gtggggcttt aggtgcaacc gtgaaacgct tatgagctac gggctccaga     60
tcttcttctg caccagagca agtctaagtc tgagccggct ccccagaac tccagctgct     120 gggtcttgaa ctcctgcgtt ccggagtcct agcgttgctg cacccaaggc cacccccaga    180
atcatgcgct gcgctccgac agcaggcgct gccctggtgc tatgcgcggc tactgcgggg    240
cttttgagcg cgcaagggcg ccctgcacag ccagagccac cgcgctttgc atcctgggac    300
gagatgaact tgctggctca cgggctgcta cagctcggcc atgggctgcg cgaacacgtg    360

```
gagcgcaccc gtgggcagct gggcgcgctg gagcgccgca tggctgcctg tggtaacgct      420
tgtcaggggc caagggaaa agatgcaccc ttcaaagact ccgaggatag agtccctgaa       480
ggccagactc ctgagactct gcagagtttg cagactcagc tcaaggctca aaacagcaag      540
atccagcaat tgttccagaa ggtggcccag cagcagagat acctatcaaa gcagaatctg      600
agaatacaga atcttcagag ccagatagac ctcttggccc ccacgcacct agacaatgga      660
gtagacaaga cttcgagggg aaagaggctt cccaagatga cccagctcat tggcttgact      720
cccaacgcca cccacttaca caggccgccc cgggactgcc aggaactctt ccaagaaggg      780
gagcggcaca gtggactttt ccagatccag cctctggggt ctccaccatt tttggtcaac      840
tgtgagatga cttcagatgg aggctggaca gtgattcaga gacgcctgaa cggctctgtg      900
gacttcaacc agtcctggga agcctacaag gatggcttcg agatccccca aggcgagttc      960
tggctgggcc tggaaaagat gcacagcatc acagggaacc gaggaagcca attggctgtg     1020
cagctccagg actgggatgg caatgccaaa ttgctccaat ttcccatcca tttgggggt      1080 gaggacacag cctacagcct gcagctcact gagcccacgg ccaatgagct gggtgccacc     1140
aatgtttccc ccaatggcct ttccctgccc ttctctactt gggaccaaga ccatgacctc     1200
cgtggggacc ttaactgtgc caagagcctc tctggtggct ggtggtttgg tacctgtagc     1260
cattccaatc tcaatggaca atacttccac tctatcccac ggcaacggca ggagcgtaaa     1320
aagggtatct tctggaaaac atggaagggc cgctactatc ctctgcaggc taccaccctg     1380
ctgatccagc ccatggaggc tacagcagcc tcttagcctc ctcactggag cctggttcca     1440
ggcctaagaa gacagtgact ttggttgtgg ccctgagatt tggccattct ctgctggggg     1500
caggagctct aagtagggct atctgcgtct tgtggacaaa gaagaagccc gtaactggag     1560
agactggagg accccttttc cgtgttgggg tctgcaagca ttgttgtctg aaacagtcag     1620
agcaacagga aacaaatggc ccagatccag aaaacatggg ctcgaggggc actgaatatc     1680
acttctcgcc taccagagaa gttggggatg cagagggacc actacagtcc aactagctgg     1740
gcccttaatg gcggactcag tcatattgac tgactggaga cagggtgcca ggagccctgg     1800
atacactcat ggtgctgttg taggtgctgt ggatgcacag gtgctaactg tggttcccag     1860
gcacagctca cagcattctt acaataaaaa caacctcaga acaaaaaaaa aaaaaa        1916
```

<210> SEQ ID NO 59
<211> LENGTH: 7826
<212> TYPE: DNA
<213> ORGANISM: Mus musculus

<400> SEQUENCE: 59

```
gctttataaa gtggggcttt aggtgcaacc gtgaaacgct tatgagctac gggctccaga       60
tcttcttctg caccagagca agtctaagtc tgagccggct cccccagaac tccagctgct      120
gggtcttgaa ctcctgcgtt ccggagtcct agcgttgctg cacccaaggc cacccccaga      180
atcatgcgct gcgctccgac agcaggcgct gccctggtgc tatgcgcggc tactgcgggg      240
cttttgagcg cgcaagggcg ccctgcacag ccagagccac cgcgctttgc atcctgggac      300
gagatgaact tgctggctca cgggctgcta cagctcggcc atgggctgcg cgaacacgtg      360
gagcgcaccc gtgggcagct gggcgcgctg gagcgccgca tggctgcctg tggtaacgct      420
tgtcaggggc caagggaaa agatgcaccc ttcaaagact ccgaggatag agtccctgaa       480
ggccagactc ctgagactct gcagagtttg caggtaggcg catctactag gactctgact      540
ctacttagac taacgagtct agtactccag gacctgggtg gagaagggcc tcagagcaga      600
```

-continued

```
ctgtgaaagg gtagaaggga gggtgaataa gaggaggttg ccgacataaa gccaggtctt    660
cactagcctt gcatatcttc agactcagct caaggctcaa aacagcaaga tccagcaatt    720
gttccagaag gtggcccagc agcagagata cctatcaaag cagaatctga gaatacagaa    780
tcttcagagc caggtaatta ccccagcaat tgggcccaaat gggaaagagg aaacaaagtg    840
ggggtgaaat gtagtgatga aatgtggcta agcagttgtt atggcatgag tcaaaagatc    900
taaccacccg tttcctgccc ggtcttagat agacctcttg gccccacgc acctagacaa    960
tggagtagac aagacttcga ggggaaagag gcttcccaag atgacccagc tcattggctt    1020
gactcccaac gccacccact acacagtga gtatctctgg tctttgctgt catctggcaa    1080
ctccccaacc accccacttg ccattccaat ccttagcctt cttgtcaggt ccaccttaat    1140
aggaaagaaa gagattctgg ccttgggttc ctgtgggctc actaggctct catcaagggt    1200
atttttatat attgcaccct cttcacttat gatcctgctt ggccagacca ccccaccatt    1260
ctttcccagc aagaatcttc ccaaaatctt attagccgtt aaccagaaca agtgaggaa    1320
ggcagatcat aaggagctaa agtttcaggg gttctgggag atggtggtgt agctcaggga    1380
catcatgcaa aggaatccag ggctgtgtgt ggatgtgtgt gcgttcccga ggtttggaac    1440
cctccaacat ctcttgatgt aactataaaa gggaaaacca gagtaagcac accccacccc    1500
cggctcctag actagacaca tcctcttaca tcttacagat acagatcctt tgtcctgtat    1560
gcttccatcc agtcacatac acatatatac ataacagttt cgatcacaat ttctaggtct    1620
tagattgtgg atgtccatgc ccaatacttt gtttcaaatt gaagtgtgtg tggagctacg    1680
cagtgcggga tgggcgggtg ggggatgggg ggcacagagt cagaggctcc cagttccaac    1740
cctgagttca tgcctattcg ttcaccccttc ttgacatctg tggctctcca cagccaacta    1800
ggtgaaagtt tggatatccc cttcacaccc taaggctgct tgctggcttt cagcccaatc    1860
ctccttagac ttaattcctc ccctggcttt tacttaggca agtacctagg catggcgagg    1920
gtcatggatg agcttttcca gggtcggcag gcataggttc tggatgggtg atgtggtgga    1980
agagaagagc tgaggggtg gttttgtggc tttggaactc ccagactcag cctagccaag    2040
tagaggaaag ttcagagctg gagagacaaa cagctggccc taatgggaac cacatggtg    2100
gtttggcagt gtgcctgtcc cgattggatg agaggaaagt aggggaaagg gagctagctg    2160
cccgagggat tggaaagtat acttcccatc tttctgggtc tgccccact cctggcagtg    2220
cagacggagc tggctggcag aaagtgcctg catgccctc ccccagtgac ctttctccta    2280
ctttccctgg ctgggctggg ggtggttctt cctgaattta gaggacttgt caaggccaag    2340
ttctttctct cctcctctcc tcttttcctt tcttcctct tccccttct tctggtaaca    2400
gacatagccg tatcccacac acacacccag cctcagtctc ccagtcccac tgtcagcatc    2460
ttctactaat tcagagtacc cctttgctca gtcagctcag ctcttgcctt accccagatc    2520
caccccgtcc attgtttgaa gtcttcactg aaacactgac tgtggggtag gctttaggtg    2580
gttacaggtc cctactgtgg acaaacttcc tcctcgtctc tggcctcagt gggaggagtg    2640
gggacatgcc tccagatgac tcttcatcag cgacaatacc tctgttcact tttgggagtc    2700
taacagggct tgagagagtg gaatagcatc cttttagaag ctgagaccca gagaaaggaa    2760
tgggaaaatg gaatccctgg catcaggacc atgtgctgat tgtcaataac aggaaggtgt    2820
gatacatggg aaaaaggctc agggagagaa gcctttgtga cctgagaggg tagacaagca    2880
gagtgggaag agtgaagatt ggtcaaggga ctgaccgttc cttagtgtgc cttgaggacc    2940
```

```
ctactggaga atgctataat gaggcaggaa cgagtttagg caaatcaccc tggggctcat    3000
cctctaccac ccagccttca cactcaccag tctcctgaaa tcactggggg cttctctcct    3060
gcttcactct ctccctttgt ctactttcag ggccgccccg ggactgccag gaactcttcc    3120
aagaagggga gcggcacagt ggacttttcc agatccagcc tctggggtct ccaccatttt    3180
tggtcaactg tgagatgact tcaggtagga tgtgctgaca cccaccccccc caaggagcct    3240 ccttgccatg cacagccctg atgtcataaa ataaagccat gtatagatca ataattacaa    3300
gcacttacct agcttgtata agctcctgag atccttccac agtaacacac accctattat    3360
gcagcttgta ggatgtagcc tgtaggaggt atatagataa tcttcttccc tattgacagg    3420
catcgcaagc tcagtgatag gtttctgtgg ttaaggtgta cagctgtcca ggcctagtca    3480
tctacaaggt gagatcaagg ccagcctggg taacttagta taaccctgtc atgcaataac    3540
aaaatataag tgagctgggg gcatagctta atgggaaagt gcctcctaca atgtacaaga    3600
ccctaaattc aatgcataga accacagttg gatatggtga cttgtgccta tatttataat    3660
cccaatactt gggaggttga ggcaaaatga ttgttgaaag tgcaaggcca gccttatctc    3720
agtcttcatg ggctgggaat aaagctcagt tggtaaagcg cttccattga atgtatgaag    3780
ccctggcttc catctccaac actgcataaa atgggtatga tagtgcaagt ctgctaccca    3840
aaactctgga ggtggtagca ggctgatgag gagtttgaga tcatccacag ttacatagtg    3900
agttgaagga cagcttgggc tataggaaaa aggtagtcta aggtagagac tctgtttcaa    3960
acaacaaaac acatatactc ctggttcctg caggctccta ggatagaagt ctgttctgat    4020
cccaccccct gcggggactg atgagtgtgt tgcccttcct gggattgtat gggagcatga    4080
tattaggctt gcaagctagg tagggctatc agtttccctg tgagaaggga cttctggtga    4140 cttttttgtct ttctgggcag atggaggctg acagtgatt cagagacgcc tgaacggctc    4200
tgtggacttc aaccagtcct gggaagccta caaggatggc ttcggagatc cccaaggtag    4260
gtgtttctct ggaggccata gtcatggaag gagcaaaggg tgcgagagtt gagcctggct    4320
cacatatgat ttctcttgat tcaggcgagt tctggctggg cctggaaaag atgcacagca    4380
tcacagggaa ccgaggaagc caattggctg tgcagctcca ggactgggat ggcaatgcca    4440
aattgctcca atttcccatc catttggggg gtgaggacac agcctacagc ctgcagctca    4500
ctgagcccac ggccaatgag ctgggtgcca ccaatgtttc ccccaatggc ctttccctgc    4560
ccttctctac ttgggaccaa gaccatgacc tccgtgggga ccttaactgt gccaagagcc    4620
tctctggtaa gcaggtttta ttcccactgt agcctacatt cagtcccaaa gtgtgtatcc    4680
atgccctgcc ccccttttct ccttgcctcc tgtgtgccta tgggccagtc attgaattaa    4740
tctctgctgt tttcagtttc cctgtcttta agtaacata atcatggtgc ctgcttttga    4800
aaattcaact gagaacattt gtgggtgtgt agctgccaca gggcaaagcc aagacaaacc    4860
cttgtcttat tcttttcaat tctgaggtat agggtcttgt gccattctgg cacagagcta    4920
caccctgacc cctggtgttt tgttttttgtt gtctgtttga ctcagggtct tatatagctc    4980
tagctggcct tgaacttgtt atacagctaa agataagctt aaagggtcag cctcggagct    5040
ggaaagatgg ctcagtggtt aagagcactg actgctcttc caggggtcc tgagttcaat    5100 tcccagcaac tccatggtgg ctcacaacca cctccaatgg ggtctgatgc cctcttctgg    5160
tgtgtctgaa gagagcaatg gtgtattcat atacattaaa taataaacc atttaaaaag    5220 ggagggggc atcagcctct aactcctgag tgttggggta acaggcatgt gccattgtgc    5280
tcctgaggat caatcccaca attccatgtc tggtaggcaa gcactgtaac aaatgagcta    5340
```

```
cagtactagc tcttttttctg cttcacttat tcagtcagga tcaaattata aagagcaggc   5400
tggcctcaaa cttcctatca tactgctgag cactgtgact acaaatttct acccacaaac   5460
tgcttcatag tgtagctcat ttggcagaga acctacctaa catgagtgaa ggcctaggtt   5520
tcattaccca taccatataa aacacacatg gttgtgcaat gtcaaccata gactcagaaa   5580
gaggaggcag gtaaagcaga cattttaaat tgtctttggc cacgtggaga gtttgaggcc   5640
agcccgatag gagaccccgt cacaaaacaa aaataggact tatgagatgg ctcagccagt   5700
aacagtgttt gcctacaatc ctgaagacct aagtttgatc tccaagactc acatagtaga   5760
aagagatcac tggctcgctc ccacaagctg tcctctgacc ttcatacccca ctgtggcatg   5820 tacacccaca cacatataca cgggaacaca agtaaataa atgtaataaa ttctaaaggt   5880
gtaaaatcca aagttcatct tgtctccaac tgtgctctct ctctctctct ctcctctctc   5940
tctctctctc tctctcagta tggaaaccca agaccttgac cacatctcct gttctttaac   6000
cctataggtg gctggtggtt tggtacctgt agccattcca atctcaatgg acaatacttc   6060
cactctatcc cacggcaacg gcaggagcgt aaaaagggta tcttctggaa aacatggaag   6120
ggccgctact atcctctgca ggctaccacc ctgctgatcc agcccatgga ggctacagca   6180
gcctcttagc ctcctcactg gagcctggtt ccaggcctaa aagacagtg actttggttg   6240 tggccctgag atttggccat tctctgctgg gggcaggagc tctaagtagg gctatctgcg   6300
tcttgtggac aaagaagaag cccgtaactg gagagactgg aggacccctt ttccgtgttg   6360
gggtctgcaa gcattgttgt ctgaaacagt cagagcaaca ggaaacaaat ggcccagatc   6420
cagaaaacat gggctcgagg ggcactgaat atcacttctc gcctaccaga aagttgggg    6480 atgcagaggg accactacag tccaactagc tgggcccctta atggcggact cagtcatatt   6540
gactgactgg agacagggtg ccaggagccc tggatacact catggtgctg ttgtaggtgc   6600
tgtggatgca caggtgctaa ctgtggttcc caggcacagc tcacagcatt cttacaataa   6660
aaacaacctc agaacatttt gttctctgtt gtttcatttg attttttcaaa gtgaatagtt   6720 tcaaagttca agtaaacatg ttcctcggac atcgtattcc cagatccgtt aaggacagaa   6780
ctggttggct attccttccc agtgatttca gcttccttct tttagtattt catgatgtga   6840
gcctctcttg tttatatttc aaaatctcaa aacaggtcca gggagatggc tcagtgatta   6900
ggaacattcg ttcttccaga gggcctgggt ttggttccca gcctttacat agcagctaac   6960
aatagcctat aactctactt caaggggggtc caatgccgcc tctgacctct actggctcct   7020
gtacaaatgt gataatatgc aaatatttag gcactcatat agaaaagaaa gtattgttta   7080
aaaaacagag ttagggaaat ggcttaatga ttccaaacac ttgctgtcta agcctggtga   7140
ctgagttcaa gcacccaaaa ggtcaaagga cagaacagat tccgcaaagt tggcctttga   7200
ccaccacata caagccatgg cacttgggct gtcacacaga tatatacaca ataattgttt   7260
tttttttaat tttaaaagt taaaaatcat ataactcatg cagtccaatc attagggaag   7320
ttggtgatag agacaagtaa aaagtctttc tgatcagtac tcggtgggt acacacagat   7380 ctccagcccc tggagctgg acataggagc tttgcaaact ctaagccaga ctaggcaata   7440
caacaagatc ctgtatcaca aacagggtga gtactgtaga tgtagctcaa ctggacatac   7500
gaagcatgca cagaccctgg gttctttccc agcagcactg cataaataaa gtatagcgct   7560
agataacact gtaatgctcg tatttgggag gtggaggcat gaggattaga agttgaggta   7620
acctgggcta caagaaagaa aaagaagaga gaaaagcaaa atgagatgaa gttaattttta   7680
```

```
gaaatctaaa cccgatgtca tattccatac ttgtaatttc agcacttggg gagctgaggc    7740
agggggacca gaattaccat gagtttgagt ccaacttagg ctatatagta agaccttgac    7800
taataaaaac aaagacgtta aaaag                                          7826
```

```
<210> SEQ ID NO 60
<211> LENGTH: 15
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 60
gttgcaccta aagcc                                                     15

<210> SEQ ID NO 61
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 61
acggttgcac ctaaagc                                                   17

<210> SEQ ID NO 62
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 62
acggttgcac ctaaag                                                    16

<210> SEQ ID NO 63
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 63
tcacggttgc acctaa                                                    16

<210> SEQ ID NO 64
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 64
ttcacggttg caccta                                                    16

<210> SEQ ID NO 65
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4
```

<400> SEQUENCE: 65
ataagcgttt cacggtt                                                      17

<210> SEQ ID NO 66
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 66
cataagcgtt tcacggt                                                      17

<210> SEQ ID NO 67
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 67
cgtagctcat aagcgtt                                                      17

<210> SEQ ID NO 68
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 68
gctaggactc cggaac                                                       16

<210> SEQ ID NO 69
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 69
acgctaggac tccgaa                                                       17

<210> SEQ ID NO 70
<211> LENGTH: 15
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 70
aacgctagga ctccg                                                        15

<210> SEQ ID NO 71
<211> LENGTH: 15
<212> TYPE: DNA
<213> ORGANISM: Artificial Sequence
<220> FEATURE:
<223> OTHER INFORMATION: antisense oligonucleotides hybridizing with
      murine ANGPLT4

```
<400> SEQUENCE: 71
agcgcatgat tctgg                                                    15

<210> SEQ ID NO 72
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 72
cggagcgcag cgcatga                                                  17

<210> SEQ ID NO 73
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 73
agccgcgcat agcacca                                                  17

<210> SEQ ID NO 74
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 74
tagccgcgca tagcac                                                   16

<210> SEQ ID NO 75
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 75
agtagccgcg catagca                                                  17

<210> SEQ ID NO 76
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 76
cagtagccgc gcatagc                                                  17

<210> SEQ ID NO 77
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 77
```

```
cagtagccgc gcatag                                                    16

<210> SEQ ID NO 78
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 78
gcagtagccg cgcata                                                    16

<210> SEQ ID NO 79
<211> LENGTH: 15
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 79
ccttgcgcgc tcaaa                                                     15

<210> SEQ ID NO 80
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 80
gatgcaaagc gcggtg                                                    16

<210> SEQ ID NO 81
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 81
aggatgcaaa gcgcggt                                                   17

<210> SEQ ID NO 82
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 82
ccacgtgttc gcgcag                                                    16

<210> SEQ ID NO 83
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 83
```
ctccacgtgt tcgcgca                                                  17

<210> SEQ ID NO 84
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 84
tgcgctccac gtgttcg                                                  17

<210> SEQ ID NO 85
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 85
tgcgctccac gtgttc                                                   16

<210> SEQ ID NO 86
<211> LENGTH: 15
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 86
tgcgctccac gtgtt                                                    15

<210> SEQ ID NO 87
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 87
atgcggcgct ccagcg                                                   16

<210> SEQ ID NO 88
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 88
ctgacaagcg ttaccac                                                  17

<210> SEQ ID NO 89
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 89
cctgacaagc gttacca                                                  17

<210> SEQ ID NO 90
<211> LENGTH: 15
<212> TYPE: DNA
<213> ORGANISM: Artificial Sequence
<220> FEATURE:
<223> OTHER INFORMATION: antisense oligonucleotides hybridizing with murine ANGPLT4

<400> SEQUENCE: 90
cctgacaagc gttac                                                15

<210> SEQ ID NO 91
<211> LENGTH: 16
<212> TYPE: DNA
<213> ORGANISM: Artificial Sequence
<220> FEATURE:
<223> OTHER INFORMATION: antisense oligonucleotides hybridizing with murine ANGPLT4

<400> SEQUENCE: 91
attgtctagg tgcgtg                                               16

<210> SEQ ID NO 92
<211> LENGTH: 17
<212> TYPE: DNA
<213> ORGANISM: Artificial Sequence
<220> FEATURE:
<223> OTHER INFORMATION: antisense oligonucleotides hybridizing with murine ANGPLT4

<400> SEQUENCE: 92
ccattgtcta ggtgcgt                                              17

<210> SEQ ID NO 93
<211> LENGTH: 17
<212> TYPE: DNA
<213> ORGANISM: Artificial Sequence
<220> FEATURE:
<223> OTHER INFORMATION: antisense oligonucleotides hybridizing with murine ANGPLT4

<400> SEQUENCE: 93
cgttcaggcg tctctga                                              17

<210> SEQ ID NO 94
<211> LENGTH: 16
<212> TYPE: DNA
<213> ORGANISM: Artificial Sequence
<220> FEATURE:
<223> OTHER INFORMATION: antisense oligonucleotides hybridizing with murine ANGPLT4

<400> SEQUENCE: 94
agagccgttc aggcgt                                               16

<210> SEQ ID NO 95
<211> LENGTH: 15
<212> TYPE: DNA
<213> ORGANISM: Artificial Sequence
<220> FEATURE:
<223> OTHER INFORMATION: antisense oligonucleotides hybridizing with murine ANGPLT4

<400> SEQUENCE: 95
gctcattggc cgtgg                                                15

```
<210> SEQ ID NO 96
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 96
agtggaagta ttgtcca                                                    17

<210> SEQ ID NO 97
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 97
tacgctcctg ccgttgc                                                    17

<210> SEQ ID NO 98
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 98
ttacgctcct gccgttg                                                    17

<210> SEQ ID NO 99
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 99
tttttacgct cctgccg                                                    17

<210> SEQ ID NO 100
<211> LENGTH: 15
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 100
ttttacgctc ctgcc                                                      15

<210> SEQ ID NO 101
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 101
agaggatagt agcggcc                                                    17
```

```
<210> SEQ ID NO 102
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 102
acaagacgca gatagcc                                                  17

<210> SEQ ID NO 103
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 103
ggcgagaagt gatattc                                                  17

<210> SEQ ID NO 104
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 104
taggcgagaa gtgatat                                                  17

<210> SEQ ID NO 105
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 105
gtaggcgaga agtgat                                                   16

<210> SEQ ID NO 106
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 106
gagtccgcca ttaagg                                                   16

<210> SEQ ID NO 107
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 107
actgagtccg ccattaa                                                  17

<210> SEQ ID NO 108
```

```
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 108
atatgactga gtccgcc                                                  17

<210> SEQ ID NO 109
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 109
aatatgactg agtccgc                                                  17

<210> SEQ ID NO 110
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 110
cgctaggact ccggaa                                                   16

<210> SEQ ID NO 111
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 111
aacgctagga ctccgga                                                  17

<210> SEQ ID NO 112
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 112
aacgctagga ctccgg                                                   16

<210> SEQ ID NO 113
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 113
caacgctagg actccg                                                   16

<210> SEQ ID NO 114
<211> LENGTH: 17
```

```
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 114
gcaacgctag gactccg                                                    17

<210> SEQ ID NO 115
<211> LENGTH: 15
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 115
gtagccgcgc atagc                                                      15

<210> SEQ ID NO 116
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 116
agtagccgcg catagc                                                     16

<210> SEQ ID NO 117
<211> LENGTH: 15
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 117
agtagccgcg catag                                                      15

<210> SEQ ID NO 118
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 118
gcagtagccg cgcatag                                                    17

<210> SEQ ID NO 119
<211> LENGTH: 15
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 119
cagtagccgc gcata                                                      15

<210> SEQ ID NO 120
<211> LENGTH: 17
<212> TYPE: DNA
```

```
<213> ORGANISM: Artificial Sequence
<220> FEATURE:
<223> OTHER INFORMATION: antisense oligonucleotides hybridizing with
      murine ANGPLT4

<400> SEQUENCE: 120
ccgcagtagc cgcgcat                                                       17

<210> SEQ ID NO 121
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 121
ccttgcgcgc tcaaaa                                                        16

<210> SEQ ID NO 122
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 122
ccttgcgcgc tcaaaa                                                        16

<210> SEQ ID NO 123
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 123
atgcaaagcg cggtgg                                                        16

<210> SEQ ID NO 124
<211> LENGTH: 15
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 124
atgcaaagcg cggtg                                                         15

<210> SEQ ID NO 125
<211> LENGTH: 15
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 125
cgctccacgt gttcg                                                         15

<210> SEQ ID NO 126
<211> LENGTH: 16
<212> TYPE: DNA
<213> ORGANISM: Artificial Sequence
```

```
<220> FEATURE:
<223> OTHER INFORMATION: antisense oligonucleotides hybridizing with
      murine ANGPLT4

<400> SEQUENCE: 126
gcgctccacg tgttcg                                                   16

<210> SEQ ID NO 127
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 127
tgagtccgcc attaagg                                                  17

<210> SEQ ID NO 128
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 128
atgactgagt ccgcca                                                   16

<210> SEQ ID NO 129
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 129
tatgactgag tccgcc                                                   16

<210> SEQ ID NO 130
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 130
aatatgactg agtccgc                                                  17

<210> SEQ ID NO 131
<211> LENGTH: 16
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 131
aatatgactg agtccg                                                   16

<210> SEQ ID NO 132
<211> LENGTH: 17
<212> TYPE: DNA
<213> ORGANISM: Artificial Sequence
<220> FEATURE:
```

```
<223> OTHER INFORMATION: antisense oligonucleotides hybridizing with
      murine ANGPLT4

<400> SEQUENCE: 132
cctagtagat gcgccta                                                     17

<210> SEQ ID NO 133
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 133
tcgttagtct aagtaga                                                     17

<210> SEQ ID NO 134
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 134
agtactagac tcgttag                                                     17

<210> SEQ ID NO 135
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 135
tcggcaacct cctctta                                                     17

<210> SEQ ID NO 136
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 136
gctttatgtc ggcaacc                                                     17

<210> SEQ ID NO 137
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 137
ttgactcatg ccataac                                                     17

<210> SEQ ID NO 138
<211> LENGTH: 17
<212> TYPE: DNA
<213> ORGANISM: Artificial Sequence
<220> FEATURE:
<223> OTHER INFORMATION: antisense oligonucleotides hybridizing with
```

-continued murine ANGPLT4

<400> SEQUENCE: 138
gttaacggct aataaga                                              17

<210> SEQ ID NO 139
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 139
tctggttaac ggctaat                                              17

<210> SEQ ID NO 140
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 140
actttagctc cttatga                                              17

<210> SEQ ID NO 141
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 141
gatcgaaact gttatgt                                              17

<210> SEQ ID NO 142
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 142
tcctctcatc caatcgg                                              17

<210> SEQ ID NO 143
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 143
acggctatgt ctgttac                                              17

<210> SEQ ID NO 144
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

```
<400> SEQUENCE: 144
ggacctgtaa ccaccta                                              17

<210> SEQ ID NO 145
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 145
gtattgtcgc tgatgaa                                              17

<210> SEQ ID NO 146
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 146
gatttgccta aactcgt                                              17

<210> SEQ ID NO 147
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 147
gagcttgcga tgcctgt                                              17

<210> SEQ ID NO 148
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 148
gtagatgact aggcctg                                              17

<210> SEQ ID NO 149
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 149
tcaatggaag cgcttta                                              17

<210> SEQ ID NO 150
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4
```

<400> SEQUENCE: 150
gtagcagact tgcacta                                                17

<210> SEQ ID NO 151
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 151
ctcatgttag gtaggtt                                                17

<210> SEQ ID NO 152
<211> LENGTH: 17
<212> TYPE: DNA
<213> ORGANISM: Artificial Sequence
<220> FEATURE:
<223> OTHER INFORMATION: antisense oligonucleotides hybridizing with
      murine ANGPLT4

<400> SEQUENCE: 152
acgtggccaa agacaat                                                17

<210> SEQ ID NO 153
<211> LENGTH: 24
<212> TYPE: DNA
<213> ORGANISM: Artificial Sequence
<220> FEATURE:
<223> OTHER INFORMATION: positive control CpG oligonucleotide

<400> SEQUENCE: 153
tcgtcgtttt gtcgttttgt cgtt                                        24

<210> SEQ ID NO 154
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 154
caccggagag catcga                                                 16

<210> SEQ ID NO 155
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 155
cacggcatgt aaggaag                                                17

<210> SEQ ID NO 156
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 156
acacacggca tgtaagg                                                17

```
<210> SEQ ID NO 157
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 157
tagtctcgac agcaggt                                              17

<210> SEQ ID NO 158
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 158
ggttcgagat gaacgga                                              17

<210> SEQ ID NO 159
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 159
tcgagatgaa cggaga                                               16

<210> SEQ ID NO 160
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 160
tctgcatcgg acacacg                                              17

<210> SEQ ID NO 161
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 161
aacttagaga accgcga                                              17

<210> SEQ ID NO 162
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 162
gccgtgaact tagagaa                                              17

<210> SEQ ID NO 163
<211> LENGTH: 16
<212> TYPE: DNA
<213> ORGANISM: Artificial Sequence
<220> FEATURE:
<223> OTHER INFORMATION: antisense oligonucleotide
```

```
<400> SEQUENCE: 163
ttagagaacc gcgagt                                                  16

<210> SEQ ID NO 164
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 164
tgaccaggaa gacgctt                                                 17

<210> SEQ ID NO 165
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 165
tcgaaatgag tctgcac                                                 17

<210> SEQ ID NO 166
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 166
cgttgagcac gtctgga                                                 17

<210> SEQ ID NO 167
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 167
cgttgagcac gtctgg                                                  16

<210> SEQ ID NO 168
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 168
cacacgtcca gttctca                                                 17

<210> SEQ ID NO 169
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 169
gcggatcggt caggagt                                                 17

<210> SEQ ID NO 170
<211> LENGTH: 17
```

```
<212> TYPE: DNA
<213> ORGANISM: Artificial Sequence
<220> FEATURE:
<223> OTHER INFORMATION: antisense oligonucleotide

<400> SEQUENCE: 170
taccacacac cgtcctg                                                    17

<210> SEQ ID NO 171
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 171
ccttgtacca cacaccg                                                    17

<210> SEQ ID NO 172
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 172
ttgtaccaca caccgt                                                     16

<210> SEQ ID NO 173
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 173
cttaacagtg gatgacc                                                    17

<210> SEQ ID NO 174
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 174
cgaggacggt ttttat                                                     16

<210> SEQ ID NO 175
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 175
aggatccgct cagctcg                                                    17

<210> SEQ ID NO 176
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 176
```
tcgtgtgagg atccgct                                                    17

<210> SEQ ID NO 177
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 177
aatcggatca cagtcgt                                                    17

<210> SEQ ID NO 178
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 178
tagcacggcg gtggcgg                                                    17

<210> SEQ ID NO 179
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 179
tagcacggcg gtggcg                                                     16

<210> SEQ ID NO 180
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 180
gcggcgactt ggactg                                                     16

<210> SEQ ID NO 181
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 181
ggacgcaaag cgcggc                                                     16

<210> SEQ ID NO 182
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 182
aggacgcaaa gcgcgg                                                     16

<210> SEQ ID NO 183
<211> LENGTH: 17
<212> TYPE: DNA
<213> ORGANISM: Artificial Sequence

```
<220> FEATURE:
<223> OTHER INFORMATION: antisense oligonucleotide

<400> SEQUENCE: 183
gcggctgaca ttgtgag                                                  17

<210> SEQ ID NO 184
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 184
ataggccgtg tcctcgc                                                  17

<210> SEQ ID NO 185
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 185
tataggccgt gtcctcg                                                  17

<210> SEQ ID NO 186
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 186
agtactggcc gttgagg                                                  17

<210> SEQ ID NO 187
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 187
gaagtactgg ccgttga                                                  17

<210> SEQ ID NO 188
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 188
tcttaagctt ctgccgc                                                  17

<210> SEQ ID NO 189
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 189
agtcaccgtc tttcgtg                                                  17
```

```
<210> SEQ ID NO 190
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 190
cgccattgag gccagtc                                                  17

<210> SEQ ID NO 191
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 191
ctgagtccgc cattgag                                                  17

<210> SEQ ID NO 192
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 192
attggcgcct gcttgtg                                                  17

<210> SEQ ID NO 193
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 193
ataccattgg cgcctgc                                                  17

<210> SEQ ID NO 194
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 194
tgagtccgcc attgagg                                                  17

<210> SEQ ID NO 195
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 195
actgagtccg ccattga                                                  17

<210> SEQ ID NO 196
<211> LENGTH: 17
<212> TYPE: DNA
<213> ORGANISM: Artificial Sequence
<220> FEATURE:
<223> OTHER INFORMATION: antisense oligonucleotide
```

```
<400> SEQUENCE: 196
tgactgagtc cgccatt                                                  17

<210> SEQ ID NO 197
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 197
tgtgactgag tccgcca                                                  17

<210> SEQ ID NO 198
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 198
ccccgtcagt caatgtg                                                  17

<210> SEQ ID NO 199
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 199
ggtccccgtc agtcaat                                                  17

<210> SEQ ID NO 200
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 200
ttcacggttg cacctaa                                                  17

<210> SEQ ID NO 201
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 201
ataagcgttt cacggt                                                   16

<210> SEQ ID NO 202
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 202
gctaggactc cggaacg                                                  17

<210> SEQ ID NO 203
```

```
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 203
cagcaacgct aggactc                                                    17

<210> SEQ ID NO 204
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 204
gtgcagcaac gctagga                                                    17

<210> SEQ ID NO 205
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 205
ccgcgcatag caccagg                                                    17

<210> SEQ ID NO 206
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 206
atgcaaagcg cggtggc                                                    17

<210> SEQ ID NO 207
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 207
ccacgtgttc gcgcagc                                                    17

<210> SEQ ID NO 208
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 208
agcgttacca caggcag                                                    17

<210> SEQ ID NO 209
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 209
```
tctatcctcg gagtctt                                                    17

<210> SEQ ID NO 210
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 210
ctcgaagtct tgtctac                                                    17

<210> SEQ ID NO 211
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 211
gaagtattgt ccattga                                                    17

<210> SEQ ID NO 212
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 212
cagaggatag tagcggc                                                    17

<210> SEQ ID NO 213
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 213
cagtctctcc agttacg                                                    17

<210> SEQ ID NO 214
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 214
gcgagaagtg atattc                                                     16

<210> SEQ ID NO 215
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 215
tcaatatgac tgagtcc                                                    17

<210> SEQ ID NO 216
<211> LENGTH: 17
<212> TYPE: DNA

```
<213> ORGANISM: Artificial Sequence
<220> FEATURE:
<223> OTHER INFORMATION: antisense oligonucleotide

<400> SEQUENCE: 216
tccagtcagt caatatg                                                  17

<210> SEQ ID NO 217
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 217
ctccagtcag tcaatat                                                  17

<210> SEQ ID NO 218
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 218
gagtcctagt agatgcg                                                  17

<210> SEQ ID NO 219
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 219
gttagtctaa gtagagt                                                  17

<210> SEQ ID NO 220
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 220
agtactagac tcgtta                                                   16

<210> SEQ ID NO 221
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 221
gcaacctcct cttattc                                                  17

<210> SEQ ID NO 222
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 222
aagatatgca aggctag                                                  17
```

```
<210> SEQ ID NO 223
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 223
gactcatgcc ataacaa                                                    17

<210> SEQ ID NO 224
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 224
gtggacctga caagaag                                                    17

<210> SEQ ID NO 225
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 225
aacggctaat aagattt                                                    17

<210> SEQ ID NO 226
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 226
gttctggtta acggcta                                                    17

<210> SEQ ID NO 227
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 227
ggtgtgctta ctctggt                                                    17

<210> SEQ ID NO 228
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 228
cctagaaatt gtgatcg                                                    17

<210> SEQ ID NO 229
<211> LENGTH: 17
<212> TYPE: DNA
<213> ORGANISM: Artificial Sequence
<220> FEATURE:
```

```
<223> OTHER INFORMATION: antisense oligonucleotide

<400> SEQUENCE: 229
aacgaatagg catgaac                                                    17

<210> SEQ ID NO 230
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 230
actttcacct agttggc                                                    17

<210> SEQ ID NO 231
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 231
ctctacttgg ctaggct                                                    17

<210> SEQ ID NO 232
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 232
ggtactctga attagta                                                    17

<210> SEQ ID NO 233
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 233
tgtaaccacc taaagcc                                                    17

<210> SEQ ID NO 234
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 234
aggtattgtc gctgatg                                                    17

<210> SEQ ID NO 235
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 235
gaacagaggt attgtcg                                                    17
```

```
<210> SEQ ID NO 236
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 236
catgtatcac accttcc                                                    17

<210> SEQ ID NO 237
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 237
taaactcgtt cctgcct                                                    17

<210> SEQ ID NO 238
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 238
gcctaaactc gttcctg                                                    17

<210> SEQ ID NO 239
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 239
atctcaggag cttatac                                                    17

<210> SEQ ID NO 240
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 240
acaagctgca taatagg                                                    17

<210> SEQ ID NO 241
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 241
tatcactgag cttgcga                                                    17

<210> SEQ ID NO 242
<211> LENGTH: 17
<212> TYPE: DNA
<213> ORGANISM: Artificial Sequence
<220> FEATURE:
<223> OTHER INFORMATION: antisense oligonucleotide
```

```
<400> SEQUENCE: 242
aatggaagcg ctttacc                                              17

<210> SEQ ID NO 243
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 243
tagcagactt gcactat                                              17

<210> SEQ ID NO 244
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 244
aggctcaact ctcgcac                                              17

<210> SEQ ID NO 245
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 245
aagagctagt actgtag                                              17

<210> SEQ ID NO 246
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 246
tataatttga tcctgac                                              17

<210> SEQ ID NO 247
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 247
ggttctctgc caaatga                                              17

<210> SEQ ID NO 248
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 248
cgtggccaaa gacaatt                                              17

<210> SEQ ID NO 249
<211> LENGTH: 16
```

```
<212> TYPE: DNA
<213> ORGANISM: Artificial Sequence
<220> FEATURE:
<223> OTHER INFORMATION: Negative control oligonucleotide

<400> SEQUENCE: 249
tacgcgcggt tgttta                                                    16

<210> SEQ ID NO 250
<211> LENGTH: 16
<212> TYPE: DNA
<213> ORGANISM: Artificial Sequence
<220> FEATURE:
<223> OTHER INFORMATION: Negative control oligonucleotide

<400> SEQUENCE: 250
ttagcgcgcg aatatg                                                    16

<210> SEQ ID NO 251
<211> LENGTH: 17
<212> TYPE: DNA
<213> ORGANISM: Artificial Sequence
<220> FEATURE:
<223> OTHER INFORMATION: Negative control oligonucleotide

<400> SEQUENCE: 251
cgaataaccg tcgtgtt                                                   17

<210> SEQ ID NO 252
<211> LENGTH: 17
<212> TYPE: DNA
<213> ORGANISM: Artificial Sequence
<220> FEATURE:
<223> OTHER INFORMATION: Negative control oligonucleotide

<400> SEQUENCE: 252
gactcgttaa accgata                                                   17
```

ANGPTL4 OLIGONUCLEOTIDES INFLUENCING THE REGULATION OF THE FATTY ACID METABOLISM

PRIORITY AND CROSS REFERENCE TO RELATED APPLICATIONS

This application is the U.S. National Stage Application under 35 U.S.C. § 371 of International Application No. PCT/EP2019/081161, filed Nov. 13, 2019, designating the U.S. and published in the English language as WO 2020/099478 A2 on May 22, 2020, which claims the benefit of European Patent Application No. EP 18206087.1, filed Nov. 13, 2018. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled ZACC231001APCSEQLIST.txt, created and last saved on May 11, 2021, which is 83,731 bytes in size. The information in the Electronic Sequence Listing is incorporated herein by reference in its entirety.

FIELD

The present invention refers to an inhibitor of ANGPTL4 such as an antisense oligonucleotide and a pharmaceutical composition comprising such an inhibitor as well as its use for treating a cardiovascular disease, obesity, diabetes type II, homozygote familial hypercholesterolemia (HoFH), heterozygote familial hypercholesterolemia (HeFH) or dislipidemia.

TECHNICAL BACKGROUND

Disturbed plasma lipids are well-known risk factors in cardiometabolic disease. Successful treatment for elevated LDL-cholesterol has been given since the mid-80's and the following decades focus has broadened towards other lipid classes such as HDL-cholesterol and triglycerides. Epidemiological studies have revealed that increased plasma triacylglycerol (TG) and concomitant remnant cholesterol is an independent risk factor for coronary heart disease (Cullen, 2000). Furthermore, hypertriglyceridemia (HTG) is a hallmark of the metabolic syndrome (MS) and is often accompanied by obesity and insulin resistance (Reaven, 1995). The increased risk of type 2 diabetes and cardiovascular disease (CVD) associated with metabolic syndrome and HTG suggests that maintenance of plasma TG homeostasis is highly desirable.

Patients with severe hypertriglyceridemia can also develop pancreatitis (Athyros, 2002), particularly when TG levels exceed 1000-1500 mg/dl (Tsuang, 2009). As many as 40 different genes are now known to regulate plasma TG (Johansen, 2011), but only a few monogenetic disorders are known to markedly increase TG (Nordestgaard and Varbo, 2014). These comprises FCS which is described in more detail below.

Lipolysis is a key step in clearance of TG-rich lipoproteins that takes place on the luminal surface of capillaries of heart, skeletal muscle, and adipose tissues. LPL synthesized in muscle and adipocytes is translocated to capillary endothelial cells. Rare genetic defects in lipoprotein lipase (LPL) (Benlian, 1996), the main enzyme responsible for the hydrolysis of TG on lipoproteins, can lead to familial chylomicronemia syndrome (FCS) characterized by plasma TG levels well over >10 mmol. Homozygous defects in apolipoprotein C-II (apoC-II), a key protein activator of LPL, can also lead to a similar hypertriglyceridemic phenotype (Breckenridge, 1978). More recently, defects in GPIHBP1, a protein that links LPL to the surface of endothelial cells (Beigneux, 2007), and mutations in apolipoprotein A-V (ApoA-V) (Ishihara, 2005) have also been described to cause hypertriglyceridemia in humans. Genetic defects in the lipase specific chaperone LMF1 has also been found to promote FCS. Taken together about 2-3:1 000 000 patients have FCS.

Not only LPL activating factors affect the LPL system; loss of function mutations in LPL negative regulators such as apoC3 and ANGPTL4, ANGPTL3 or ANGPTL8 has been shown to promote a favorable plasma lipid profile and a reduced risk for metabolic diseases. ANGPTL4 is a regulator of different lipases and LPL in particular. The protein is unfolding chaperones that break up the dimeric catalytically active form of LPL into inactive monomers which is an irreversible event. The ANGPTLs are the only known factors to regulate LPL in this manner, compared to e.g. apoC3 which displaces LPL from lipid substrates. In addition ANGPTL4 affects hepatic lipase and endothelial lipase thus affecting not only the TG moiety of plasma lipids but also LDL-c and HDL-c. ANGPTL4 is a fasting induced factor expressed also by the liver but to a relevant extent by adipose tissue and skeletal muscle as well, i.e., ANGPTL4 is expressed ubiquitary. The expression of ANGPTL4 is regulated by different stimuli; it is for example induced in the liver by Peroxisome Proliferator-Activator Receptor (PPAR) α, PPARδ and the glucocorticoid receptor (GR), respectively. Animal models deficient for these ANGPTLs show increased LPL activity and decreased plasma lipids and mice with transgenic overexpression for the human variants show the opposite. The findings from animal studies are supported by human deficiency and loss of function mutations which correlates for ANGPTL4 with plasma TG levels and HDL-c. The ANGPTL4 gene shows a link to cardiometabolic diseases.

Thus, information to date provides new insights into the coordinate activities of LPL, GPIHBP1, ANGPTLs and apoA-V in plasma TG homeostasis. Among these factors, ANGPTL4 also regulates plasma cholesterol levels i.e. LDL-c, HDL-c and remnant-c intriguingly without being all dependent on the LDL-receptor which in most cases is non-functional in homozygote familial hypercholesterolemia (HoFH) and heterozygote familial hypercholesterolemia (HeFH). This provides an opportunity for an "all-purpose" plasma lipid drug while targeting ANGPTL4.

ANGPTL4 regulates the activity of the lipoprotein lipase that plays an important role in the intake of free fatty acids into the liver. Dysregulation of lipoprotein lipase can lead to a lipid excess in the cells, which results for example in obesity, diabetes type II or cardiovascular diseases.

ANGPTL4 knock-out mice show reduced triglyceride (TG) level based on increased degradation of very low-density lipoprotein (VLDL) and reduced VLDL production. The cholesterol level is influenced moderately. Food having high lipid level results in ANGPTL4 knock-out mice which are treated with monoclonal antibodies to reduced viability due to lesions of lipogranuloma of the intestinal tissue, the effluent lymphatic system and/or the mesenteric lymph nodes (Desai et al., 2007 PNAS). Humans being heterozygous for the ANGPTL4 variant E40K show significant lower plasma TG level when fasting. Also the high density lipoprotein (HDL) cholesterol levels were significantly higher in E40K heterozygous humans. As the combination of high TG and low HDL cholesterol level leads to an increased risk to suffer from cardiovascular diseases, the reduction or inhibition of ANGPTL4 may reduce the risk. ANGPTL4 null alleles exist in humans, but a pathology comparable to ANGPTL4 knock-out mice has not been identified so far.

Oligonucleotides of the present invention inhibiting the expression of ANGPTL4 reduce for example the plasma lipid level independent of LDL receptor functionality, which is relevant for example for use of the oligonucleotides in treating homozygote familial hypercholesterolemia (HoFH) or heterozygote familial hypercholesterolemia (HeFH), where the LDL receptor is defect.

ANGPTL4 is not only involved in the regulation of the fatty acid metabolism, but it is also involved in influenza infection. ANGPTL4 is for example upregulated by STAT3-mediated mechanism during influenza pneumonia and is a potential biomarker for respiratory infection and pneumonia (Li et al., Cell Reports 10, February 2015).

So far no antisense oligonucleotide exists which is highly efficient in reduction and inhibition, respectively, of ANGPTL4 expression and hybridizes with ANGPTL4 mRNA and/or pre-mRNA. Studies with siRNA to inhibit ANGPTL4 expression showed that in vivo inhibition is only possible if siRNA is packed in suitable packaging material. Even if siRNA is packed the efficiency on the inhibition of mRNA expression can often not be improved.

An oligonucleotide of the present invention is very successful in the inhibition of the expression of ANGPTL4. The mode of action of an oligonucleotide differs from the mode of action of an antibody or small molecule, and oligonucleotides are highly advantageous regarding for example
  (i) the penetration into tissues,
  (ii) the blocking of multiple functions and activities, respectively, of a target,
  (iii) the combination of oligonucleotides with each other or an antibody or a small molecule, and
  (iv) the inhibition of intracellular effects which are not accessible or not specifically accessible for an antibody or inhibitable via a small molecule.

SUMMARY

The present invention refers to an ANGPTL4 inhibitor consisting of an oligonucleotide comprising or consisting of for example 12 to 22 nucleotides, 15 to 20 nucleotides, or 15, 16, 17, 18, 19 or 20 nucleotides, wherein at least one of the nucleotides is modified. The ANGPTL4 oligonucleotide hybridizes for example with a nucleic acid sequence of ANGPTL4 of SEQ ID NO.1 (human; NM_139314), ANGPTL4 of SEQ ID NO. 2 (human; GRCh38_19_8364151_8374373) ANGPTL4 of SEQ ID NO.58 (mouse; NM_020581.2) and/or ANGPTL4 of SEQ ID NO.59 (mouse; GRCm38:17:33773750:33781575), wherein the oligonucleotide inhibits the expression of ANGPTL4. The modified nucleotide is for example selected from the group consisting of a bridged nucleic acid such as LNA, cET, ENA, 2'Fluoro modified nucleotide, 2'O-Methyl modified nucleotide, 2' O-Methoxyethyl modified nucleotide and a combination thereof.

The ANGPTL4 oligonucleotide of the present invention hybridizes for example with an active area selected from position 1732-1759 (e.g., A24044He, SEQ ID NO.47; A24076He, SEQ ID NO.47) and/or from position 234-261 (e.g. A24102He, SEQ ID NO. 177; A24103He, SEQ ID NO. 178) and/or from position 1264-1293 (e.g. A24110He, SEQ ID NO. 186; A24111He, SEQ ID NO. 187) of SEQ ID NO. 1 and/or from position 2800-2872 (eg. A24083Hi, SEQ ID NO. 158; A24085Hi, SEQ ID NO. 160; A24086Hi, SEQ ID NO. 161; A24087Hi, SEQ ID NO. 162) and/or from position 3415-3442 (e.g. A24089Hi, SEQ ID NO. 164) and/or from position 4968-4994 (e.g. A24097Hi, SEQ ID NO. 172) of SEQ ID NO.2 or a combination thereof. It inhibits the expression of ANGPTL4 for example at a nanomolar or micromolar concentration.

The present invention is further directed to a pharmaceutical composition comprising an ANGPTL4 inhibitor of the present invention and a pharmaceutically acceptable carrier, excipient, dilutant or a combination thereof. The inhibitor and the pharmaceutical composition, respectively, are for use in a method of preventing and/or treating a disorder, where an ANGPTL4 imbalance is involved. Such disorder is for example a cardiometabolic disease, obesity, diabetes such as type 2 diabetes mellitus, hypercholesterolemia, hypertriglyceridemia (HTG), dyslipidemia, pancreatitis, metabolic syndrome, familial chylomicronemia syndrome (FCS), influenza infection and/or cancer. Hypercholesterolemia is for example homozygote familial hypercholesterolemia (HoFH) and heterozygote familial hypercholesterolemia (HeFH), cancer is for example breast cancer, lung cancer, malignant melanoma, lymphoma, skin cancer, bone cancer, prostate cancer, liver cancer, brain cancer, cancer of the larynx, gall bladder, pancreas, testicular, rectum, parathyroid, thyroid, adrenal, neural tissue, head and neck, colon, stomach, bronchi, kidneys, basal cell carcinoma, squamous cell carcinoma, metastatic skin carcinoma, osteo sarcoma, Ewing's sarcoma, reticulum cell sarcoma, liposarcoma, myeloma, giant cell tumor, small-cell lung tumor, islet cell tumor, primary brain tumor, meningioma, acute and chronic lymphocytic and granulocytic tumors, acute and chronic myeloid leukemia, hairy-cell tumor, adenoma, hyperplasia, medullary carcinoma, intestinal ganglioneuromas, Wilm's tumor, seminoma, ovarian tumor, leiomyomater tumor, cervical dysplasia, retinoblastoma, soft tissue sarcoma, malignant carcinoid, topical skin lesion, rhabdomyosarcoma, Kaposi's sarcoma, osteogenic sarcoma, malignant hypercalcemia, renal cell tumor, polycythermia vera, adenocarcinoma, anaplastic astrocytoma, glioblastoma multiforma, leukemia, or epidermoid carcinoma.

The ANGPTL4 inhibitor or the pharmaceutical composition of the present invention comprising the ANGPTL4 inhibitor are administered locally or systemically.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

More specifically, all referenced documents are incorporated by reference to the same extent as if each individual document was specifically and individually indicated to be incorporated by reference.

BRIEF DESCRIPTION OF THE DRAWINGS

FIG. 1 shows an initial screen of 42 human ANGPTL4-specific antisense oligonucleotides. A control oligonucleotide that does not have sequence complementarity to any human or mouse mRNA (Neg1; SEQ ID NO.57) was included as a control. Human epithelioid cervix carcinoma cells (HeLa) were treated with the respective oligonucleotides at a single concentration of 10 µM for three days. Three days after start of treatment, cells were lysed and ANGPTL4 and HPRT1 mRNA levels were determined using the QuantiGene Singleplex RNA assay. HPRT1 was used as a housekeeping gene for normalization of ANGPTL4 expression. Residual ANGPTL4-mRNA expression relative to mock-treated cells ("no oligo" set as 1). Triplicate wells, mean+/−SD (FIG. 1).

FIG. 2 depicts another screen of human ANGPTL4-specific antisense oligonucleotides in SK-OV3 cells to investigate the residual ANGPTL4 mRNA expression.

FIG. 3 depicts further human ANGPTL4-specific antisense oligonucleotides tested in HeLa cells at a concentration of 10 µM. Four of the tested antisense oligonucleotides show more than 50% knockdown of ANGPTL4 mRNA (equivalent to residual mRNA level of <0.5), FIG. 4 shows another screen of further ANGPTL4-specific antisense oligonucleotides in SK-OV3 cells to investigate the residual ANGPTL4 mRNA expression.

FIG. 5 depicts HEK-Blue™ hTLR9 cells used to study the stimulation of human TLR9 by monitoring the activation of nuclear factor 'kappa-light-chain-enhancer' of activated B-cells (NF-kB)-dependent secreted embryonic alkaline phosphatase (SEAP)-production in vitro. ANGPTL4 oligonucleotides A24022Hi (SEQ ID NO.25), A24023Hi (SEQ ID NO.26), A24071Hi (SEQ ID NO.54) and A24076He (SEQ ID NO.47) as well as controls Neg1 (SEQ ID NO.57) and ODN2006 (5'-TCGTCGTTTTGTCGTTTTGTCGTT-3' PTO-modified-Invivogen cat. no. tlrl-2006; SEQ ID NO.153) were analyzed.

FIG. 6 shows the human ANGPTL4-specific antisense oligonucleotides A24022Hi (SEQ ID NO. 25), A24023Hi (SEQ ID NO. 26), A24071Hi (SEQ ID NO.54) and A24076He (SEQ ID NO.47) with most potent knockdown efficacy in HeLa and SK-OV3 cells, which were selected for determination of half maximal inhibitory concentration ($IC_{50}$) values. Primary hepatocytes were treated with the respective ANGPTL4 antisense oligonucleotides at different concentrations (5000 nM, 1000 nM, 200 nM, 40 nM, 8 nM, 1.6 nM) for three days and simultaneously treated with PPARγ (1 µM). Three days after start of treatment, mRNA expression was analyzed using the QuantiGene Singleplex RNA assay as depicted in FIG. 6. For graphic representation mock-treated cells were set as 0.32 nM.

FIG. 7 shows a first single dose efficacy screen of the additional ANGPTL4-specific antisense oligonucleotides (ASOs) in primary hepatocytes. 25,000 cells/well were seeded in 96-well collagen I-coated flat bottom plates and treated with the respective ASOs at a final concentration of 5 µM. To induce ANGPTL4 mRNA expression, cells were simultaneously treated with 1 µM PPARγ. As a vehicle control, cells were treated with equal amount of DMSO ("DMSO"). Every 24 h, 70 µl of supernatant was replaced with fresh medium containing PPARγ as well as the respective ASOs at 5 µM or DMSO. After three days, cells were lysed and human HPRT1 as well as human ANGPTL4 mRNA expression was measured using the QuantiGene RNA Singleplex assay. ANGPTL4-mRNA expression values were normalized to expression of the housekeeping gene HPRT1. Residual ANGPTL4-mRNA expression relative to mock-treated cells ("no oligo" set as 1 (n=42), SD=0.24) is shown. Solid line and dotted lines indicate 70% and 0% knockdown efficacy (upper graph) or 100% HPRT1 expression of mock-treated cells ("no oligo" set as 100 (n=42), SD=35.8, graph below), respectively. Data are represented as mean of triplicate wells+/−SD. Positive control ASOs are marked by an asterix.

FIG. 8 depicts a second single dose efficacy screen of the additional ANGPTL4-specific ASOs in primary hepatocytes. 25,000 cells/well were seeded in 96-well collagen I-coated flat bottom plates and treated with the respective ASOs at a final concentration of 5 µM. To induce ANGPTL4 mRNA expression, cells were simultaneously treated with 1 µM PPARγ. As a vehicle control, cells were treated with equal amount of DMSO ("DMSO") or left untreated ("−DMSO"). Every 24 h, 70 µl of supernatant was replaced with fresh medium containing PPARγ as well as the respective ASOs at 5 µM or DMSO or medium only. After three days, cells were lysed and human HPRT1 as well as human ANGPTL4 mRNA expression were measured using the QuantiGene RNA Singleplex assay. ANGPTL4-mRNA expression values were normalized to expression of the housekeeping gene HPRT1. Residual ANGPTL4-mRNA expression relative to mock-treated cells ("no oligo" set as 1 (n=36), SD=0.24) is shown. Solid line and dotted lines indicate 70% and 0% knockdown efficacy (upper graph) or 100% HPRT1 expression of mock-treated cells ("no oligo" set as 100 (n=36), SD=19.3, graph below), respectively. Data are represented as mean of sextuplicate (A24076He and negative control oligonucleotides), nonuplicate (−DMSO) or triplicate (all other ASOs) wells+/−SD. Positive control ASO is marked by an asterix.

FIG. 9 depicts NF-kB-activation in HEK-Blue hTLR9 SEAP reporter cells. HEK-Blue-hTLR9 cells were seeded in flat-bottom 96-well plates and treated with the indicated oligonucleotides for 24 h. Cell supernatants were harvested after the incubation and incubated for 4 h (FIGS. 9A, 9C and 9D) or 3.5 h (FIG. 9B) with QUANTI-Blue solution. SEAP activity was determined by measurement of the optical density (OD) at 620 nm. Data for ANGPTL4-specific ASOs and neg1 treated cells are depicted as mean of triplicates+/−SD of OD units relative to OD units from cells stimulated with 5000 nM ODN2006 (set to 100%). Data for ODN2006 treated cells are depicted as mean+/−SD of sextuplicates (A), as mean+/−SD of triplicates (D) or as the mean+/−SD of the means of triplicates on each plate (B-C).

FIG. 10 shows $IC_{50}$ determination of selected ANGPTL4 ASOs. 25,000 primary human hepatocytes/well were seeded in 96-well plates and treated with different concentrations (5000 nM, 1000 nM, 200 nM, 40 nM, 8 nM, 1.6 nM) of the respective ASO. Every 24 h, 70 µl of supernatant was replaced with fresh medium containing the respective ASOs at indicated concentrations. After three days, cells were lysed and HPRT1 and ANGPTL4 mRNA expression was measured using the QuantiGene RNA Singleplex assay. ANGPTL4-mRNA expression values were normalized to expression of the housekeeping gene HPRT1. Residual ANGPTL4-mRNA expression relative to mock-treated cells (set as 1 (n=36), SD=0.26). Data are represented as mean of triplicate wells +/−SD.

FIG. 11 shows the efficacy of selected ANGPTL4 ASOs on target gene expression after transfection of cynomolgus hepatocytes. 25,000 primary cynomolgus hepatocytes/well were seeded in 96-well plates and transfected with different concentrations (2 nM, 0.2 nM) of the respective ASO. After 24 h incubation at 37° C., cells were lysed and HPRT1 and ANGPTL4 mRNA expression were measured using the QuantiGene RNA Singleplex assay. ANGPTL4-mRNA expression values were normalized to expression of the housekeeping gene HPRT1. Residual ANGPTL4-mRNA expression relative to mock-treated cells (set as 1 (n=12), SD=0.25) is depicted. Data are represented as mean of triplicate wells+/−SD.

FIG. 12 depicts mouse embryonic fibroblasts (3T3 cells) separately treated with the mouse ANGPTL4-specific antisense oligonucleotides as shown in FIG. 12 at a single concentration of 10 µM. Three days after start of treatment, the mRNA levels were determined by QuantiGene RNA Singleplex assay. Hprt1 was used as a housekeeping gene for normalization of ANGPTL4 expression. Eight ANGPTL4 antisense oligonucleotides, which are A24047M (SEQ ID NO.106), A24020M (SEQ ID NO.79), A24017M (SEQ ID NO.76), A24021M (SEQ ID NO.80), A24049M (SEQ ID NO.108), A24018M (SEQ ID NO.77), A24041M (SEQ ID NO.100) and A24010M (SEQ ID NO.69), reduced the normalized ANGPTL4 expression by more than 50%.

FIG. 13 depicts mouse renal carcinoma Renca cells separately treated with the ANGPTL4-specific antisense oligonucleotides as shown in FIG. 13 at a single concentration of 10 µM. After three days the mRNA levels were determined by QuantiGene RNA Singleplex assay. Hprt1 was used as a housekeeping gene for normalization of ANGPTL4 expression. A24020M (SEQ ID NO.79) and A24019M (SEQ ID NO.78) resulted in ANGPTL4 knockdown of more than 50% (equivalent to residual mRNA level of <0.5).

FIG. 14 depicts 9 already tested as well as 24 further mouse ANGPTL4-specific antisense oligonucleotides tested in mouse breast cancer cells 4T1. Cells were treated with 5 µM of respective ANGPTL4 antisense oligonucleotides as shown in FIG. 14 without using a transfection reagent. After three days, cell supernatant was replaced by fresh medium containing 5 µM of the respective ANGPTL4 antisense oligonucleotides and incubated for further three days. Afterwards, the mRNA levels were determined by QuantiGene RNA Singleplex assay. Gapdh was used as a housekeeping gene for normalization of ANGPTL4 expression. 12 of the tested antisense oligonucleotides, which are A24017M (SEQ ID NO.76), A24070M (SEQ ID NO.127), A24020M (SEQ ID NO.79), A24019M (SEQ ID NO.78), A24069M (SEQ ID NO.126), A24021M (SEQ ID NO.80), A24011M (SEQ ID NO.70), A24073M (SEQ ID NO. 130), A24018M (SEQ ID NO.77), A24055M (SEQ ID NO.114), A24010M (SEQ ID NO.69), and A24065M (SEQ ID NO.79) show more than 80% knockdown of ANGPTL4 mRNA (equivalent to residual mRNA level of <0.2).

FIG. 15 shows 21 mouse ANGPTL4-specific antisense oligonucleotides tested in 4T1 cells by treating them with 5 µM of the respective ANGPTL4 antisense oligonucleotide as shown in FIG. 15. After three days, cell supernatant was replaced by fresh medium containing 5 µM of the respective ANGPTL4 antisense oligonucleotide and incubated for additional three days. Afterwards, the mRNA levels were determined by QuantiGene RNA Singleplex assay. Hprt1 was used as a housekeeping gene for normalization of ANGPTL4 expression. A24047M (SEQ ID NO.106), A24095Mi (SEQ ID NO. 151), A24093Mi (SEQ ID NO. 149), A24020M (SEQ ID NO.79), A24090Mi (SEQ ID NO. 146), and A24082Mi (SEQ ID NO. 139) show more than 50% knockdown of ANGPTL4 mRNA (equivalent to residual mRNA level of <0.5).

FIG. 16 depicts A24018M (SEQ ID NO.77), A24019M (SEQ ID NO.78), A24020M (SEQ ID NO.79), A24021M (SEQ ID NO.80), A24047M (SEQ ID NO.106), A24054M (SEQ ID NO.113), A24065M (SEQ ID NO.79), A24070M (SEQ ID NO.127), A24072M (SEQ ID NO.129), A24082M (SEQ ID NO.139) and A24095Mi (SEQ ID NO.151) with most potent knockdown efficacy in 3T3, Renca and 4T1 cells, which were selected for determination of half maximal inhibitory concentration ($IC_{50}$) values. 4T1 cells were treated with these ANGPTL4 antisense oligonucleotides at different concentrations (5000 nM, 1000 nM, 200 nM, 40 nM, 8 nM, 1.6 nM) for three days. After three days, cell supernatant was replaced by fresh medium containing 5 µM of the respective ANGPTL4 antisense oligonucleotides and incubated for additional three days. Then, mRNA expression was analyzed using the QuantiGene Singleplex RNA assay.

FIG. 17 shows a $1^{st}$ single dose efficacy screen of additional mouse Angptl4-specific ASOs in 4T1 cells. 2,500 4T1 cells/well were seeded in 96-well flat bottom plates and treated with the respective ASOs at a final concentration of 5 µM. Three days after treatment, cell supernatant was replaced by fresh medium w/ ASO and cells were incubated for further three days at 37° C. Afterwards, cells were lysed and mouse Hprt1 and mouse Angptl4 mRNA expression were measured using the QuantiGene RNA Singleplex assay. Angptl4-mRNA expression values were normalized to expression of the housekeeping gene Hprt1. Residual Angptl4-mRNA expression relative to mock-treated cells ("no oligo" set as 1 (n=37), SD=0.21) is shown. Solid line and dotted line indicate 75% and 0% knockdown efficacy (upper graph) or 100% Hprt1 level (graph below) ("no oligo" set as 1 (n=37), SD=0.17), respectively. Data are represented as mean of triplicate wells+/−SD.

FIG. 18 shows a $2^{nd}$ single-dose screen of mouse Angptl4-specific ASOs in Renca cells. 2,500 Renca cells/well were seeded in 96-well flat bottom plates and treated with the respective ASOs at a final concentration of 5 µM. Three days after treatment, cell supernatant was replaced by fresh medium w/ ASO and cells were incubated for further three days at 37° C. Afterwards, cells were lysed and mouse Hprt1 and mouse Angptl4 mRNA expression were measured using the QuantiGene RNA Singleplex assay. Angptl4-mRNA expression values were normalized to expression of the housekeeping gene Hprt1. Residual Angptl4-mRNA expression relative to mock-treated cells ("no oligo" set as 1 (n=37), SD=0.37) is shown. Solid line and dotted line indicate 75% and 0% knockdown efficacy (upper graph) or 100% Hprt1 level (graph below) ("no oligo" set as 1 (n=37), SD=0.36), respectively. Data are represented as mean of triplicate wells+/−SD.

FIG. 19 shows $IC_{50}$ determination of selected Angptl4 ASOs. 15,000 primary mouse hepatocytes/well were seeded in 96-well flat bottom plates and treated with different concentrations (5000 nM, 1000 nM, 200 nM, 40 nM, 8 nM, 1.6 nM) of the respective ASO. After three days, cells were lysed and Hprt1 and Angptl4 mRNA expression were measured using the QuantiGene RNA Singleplex assay. Angptl4-mRNA expression values were normalized to expression of the housekeeping gene Hprt1. Residual Angptl4-mRNA expression relative to mock-treated cells (set as 1 (n=36), SD=0.17). Neg1 is displayed in black. Graph below shows Hprt1 raw values relative to no oligo (set as 100 (n=36), SD=13.0). Data are represented as mean of triplicate wells+/−SD.

DETAILED DESCRIPTION

The present invention provides a successful inhibitor of ANGPTL4 expression, which is a human or mouse oligonucleotide hybridizing with mRNA and/or pre-mRNA sequences of ANGPTL4 and inhibits the expression and activity, respectively, of ANGPTL4. mRNA comprises only exons of the ANGPTL4 encoding nucleic acid sequence, whereas pre-mRNA comprises exons and introns of the ANGPTL4 encoding nucleic acid sequence. Thus, the oligonucleotides of the present invention represent an interesting and highly efficient tool for use in a method of preventing and/or treating disorders, where the ANGPTL4 expression and activity, respectively, is increased.

In the following, the elements of the present invention will be described in more detail. These elements are listed with specific embodiments, however, it should be understood that they may be combined in any manner and in any number to create additional embodiments. The variously described examples and embodiments should not be construed to limit the present invention to only the explicitly described embodiments. This description should be understood to support and encompass embodiments which combine the explicitly described embodiments with any number of the disclosed elements. Furthermore, any permutations and combinations of all described elements in this application should be considered disclosed by the description of the present application unless the context indicates otherwise.

Throughout this specification and the claims, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example"), provided herein is intended merely to better illustrate the invention and does not pose a limitation on the scope of the invention otherwise claimed. No language in the specification should be construed as indicating any non-claimed element essential to the practice of the invention.

An inhibitor which is an oligonucleotide of the present invention is for example an antisense oligonucleotide (ASO) consisting of or comprising 10 to 25 nucleotides, 12 to 22 nucleotides, 15 to 20 nucleotides or 16 to 18 nucleotides. The oligonucleotides for example consist of or comprise 10, 11, 12, 13, 14, 15, 16, 17, 18, 19, 20, 21, 22, 23, 24 or 25 nucleotides.

The oligonucleotide of the present invention forms for example a gapmer consisting of or comprising a central block of at least 5 nucleotides, i.e., deoxynucleotides and/or ribonucleotides, which is flanked by for example naturally and/or artificially modified nucleotides such as deoxynucleotides and/or ribonucleotides.

The oligonucleotides of the present invention comprise at least one nucleotide which is modified. The modified nucleotide is for example a bridged nucleotide such as a locked nucleic acid (LNA, e.g., 2',4'-LNA), cET, ENA, a 2'Fluoro modified nucleotide, a 2'O-Methyl modified nucleotide, 2' O-Methoxyethyl modified nucleotide or a combination thereof. In some embodiments, the oligonucleotide of the present invention comprises one or more nucleotides having the same or different modifications. In addition, the oligonucleotide of the present invention optionally comprises a modified phosphate backbone, wherein the phosphate is for example a phosphorothioate.

The oligonucleotide of the present invention comprises the one or more modified nucleotide at the 3'- and/or 5'-end of the oligonucleotide and/or at any position within the oligonucleotide, wherein modified nucleotides follow in a row of for example 1, 2, 3, 4, 5, or 6 modified nucleotides, or a modified nucleotide is combined with one or more unmodified nucleotides. The following Tables 1 to 4 present examples of ANGPTL4 oligonucleotides comprising modified nucleotides for example LNA which are indicated by (+) and phosphorothioate (PTO) indicated by (*). The ANGPTL4 oligonucleotides consisting of or comprising the sequences of Table 1 or 2 (human), or Table 3 or 4 (mouse) may comprise any other modified nucleotide and/or any other combination of modified and unmodified nucleotides. ANGPTL4 oligonucleotides of Table 1 hybridize with mRNA and/or pre-m RNA of human ANGPTL4:

TABLE 1

List of antisense oligonucleotides hybridizing with human ANGPLT4 mRNA and/or pre-mRNA for example of SEQ ID NO. 1 and/or SEQ ID NO. 2;

| Seq ID | Name | Antisense Sequence 5'-3' | Antisense Sequence 5'-3' with PTO (*) and LNA (+) |
|---|---|---|---|
| 3 | A24001Hi | AGGCTAAGTTAGTGGCC | +A*G*C*T*A*A*G*T*T*A*G*T*G*G*+C*+C |
| 4 | A24002Hi | GCCAGATAGGCTAAGTT | +G*+C*C*A*G*A*T*A*G*G*C*T*A*A*+G*+T*+T |
| 5 | A24003He | CTGGAAAGAATCGGATC | +C*+T*G*+G*A*A*A*G*A*A*T*C*G*G*+A*+T*+C |
| 6 | A24004He | CGCTGGAAAGAATCGGA | +C*G*+C*T*G*G*A*A*A*G*A*A*T*+C*+G*+G*+A |
| 7 | A24005Hi | GCTAGTCTCGACAGCAG | +G*C*+T*A*G*T*C*T*C*G*A*C*A*G*C*+A*+G |
| 8 | A24006Hi | GATCCTCATGATAGGCC | +G*+A*T*C*C*T*C*A*T*G*A*T*A*G*G*+C*+C |
| 9 | A24007He | GGCCGTCGGAGCACCGC | +G*+G*C*C*G*T*C*G*G*A*G*C*A*C*C*G*+C |
| 10 | A24008Hi | CATGCTGTGGTTCGAGA | +C*+A*+T*G*C*T*G*T*G*G*T*T*C*G*+A*+G*+A |
| 11 | A24009He | CGTGCGCCAGGACATTC | +C*+G*T*G*C*G*C*C*A*G*G*A*C*A*+T*+T*+C |

TABLE 1-continued

List of antisense oligonucleotides hybridizing with
human ANGPLT4 mRNA and/or pre-mRNA for example of
SEQ ID NO. 1 and/or SEQ ID NO. 2;

| Seq ID | Antisense Name | Antisense Sequence 5'-3' | Antisense Sequence 5'-3' with PTO (*) and LNA (+) |
|---|---|---|---|
| 12 | A24010He | CGTGCGCCAGGACATT | +C*+G*+T*G*C*G*C*C*A*G*G*A*C+A*+T*+T |
| 13 | A24011He | TCCGTGCGCCAGGACAT | +T*C*C*G*T*G*C*G*C*C*A*G*G*A*+C*A+T |
| 14 | A24012He | GGAGTCCGTGCGCCAGG | +G*G*A*G*T*C*C*G*T*G*C*G*C*C*+A*G*+G |
| 15 | A24013He | TGCGCTCCGCGTGTTCG | +T*+G*C*G*C*T*C*C*G*C*G*T*G*T*T*+C*+G |
| 16 | A24014He | TGCGCTCCGCGTGTTC | +T*+G*C*G*C*T*C*C*G*C*G*T*G*T*T*+C |
| 17 | A24015He | GTGCGCTCCGCGTGTT | +G*+T*G*C*G*C*T*C*C*G*C*G*T*G*T*+T |
| 18 | A24016Hi | GTCGAAATGAGTCTGCA | +G*+T*+C*G*A*A*A*T*G*A*G*T*C*T*+G*+C*+A |
| 19 | A24017Hi | GCACGTCTGGAGGCTCA | +G*+C*+A*C*G*T*C*T*G*G*A*G*G*C*+T*+C*+A |
| 20 | A24018Hi | TTGAGCACGTCTGGAGG | +T*+T*+G*A*G*C*A*C*G*T*C*T*G*G*+A*+G*+G |
| 21 | A24019Hi | GGATCGCAGTGCCGCAA | +G*+G*+A*T*C*G*C*A*G*T*G*C*C*G*C*+C*+A*+A |
| 23 | A24020He | GCTGAATTCGCAGGTGC | +G*C*+T*G*A*A*T*T*C*G*C*A*G*G*+T*G*+C |
| 24 | A24021Hi | GATCGCAGTGCCGCAA | +G*+A*+T*C*G*C*A*G*T*G*C*C*G*+C*+A*+A |
| 25 | A24022Hi | GTGTTGTAACCTCTTGT | +G*+T*+G*T*T*G*T*A*A*C*C*T*C*T*+T*+G*+T |
| 26 | A24023Hi | CCGTGTTGTAACCTCTT | +C*+C*+G*T*G*T*T*G*T*A*A*C*C*T*+C*+T*+T |
| 27 | A24024He | CCTCATGGTCTAGGTGC | +C*+C*+T*+C*A*T*G*G*T*C*T*A*G*G*+T*+G*+C |
| 28 | A24025He | CACCTCATGGTCTAGGT | +C*A*+C*C*T*C*A*T*G*G*T*C*T*A*+G*+T |
| 29 | A24026He | GGCGCCTCTGAATTACT | +G*G*C*G*C*C*T*C*T*G*A*A*T*T*+A*+C*+T |
| 30 | A24027He | CGTGGCGCCTCTGAATT | +C*+G*+T*G*G*C*G*C*C*T*C*T*G*A*+A*+T*+T |
| 31 | A24028He | TCGTGGCGCCTCTGAAT | +T*C*G*T*G*G*C*G*C*C*T*C*T*G*A*+A*+T |
| 32 | A24029He | CCGCCTTGTAGGCTTCC | +C*+C*+G*C*C*T*T*G*T*A*G*G*C*T*T*C*+C |
| 33 | A24030He | ACTCGGCGTTGCCATCC | +A*+C*+T*C*G*G*C*G*T*T*G*C*C*A*T*C*+C |
| 34 | A24031He | GCCGTGTCCTCGCCACC | +G*+C*C*G*T*G*T*C*C*T*C*G*C*C*A*C*+C |
| 35 | A24032He | GAGGTCGTGATCCTGGT | +G*+A*+G*G*T*C*G*T*G*A*T*C*C*T*+G*+G*+T |
| 36 | A24033He | GCGGAGGTCGTGATCCT | +G*+C*+G*G*A*G*G*T*C*G*T*G*A*T*C*+C*+T |
| 37 | A24034He | CCTGCGGAGGTCGTGAT | +C*C*T*G*C*G*G*A*G*G*T*C*G*T*+G*+A*+T |
| 38 | A24035He | CTCTTGGCGCAGTTCTT | +C*+T*+C*T*T*G*G*C*G*C*A*G*T*T*+C*+T*+T |
| 39 | A24036He | GCTCTTGGCGCAGTTCT | +G*+C*+T*C*T*T*G*G*C*G*C*A*G*T*+T*+C*+T |
| 40 | A24037He | GGCTCTTGGCGCAGTTC | +G*+G*+C*T*C*T*T*G*G*C*G*C*A*G*T*+T*+C |
| 41 | A24038He | GGTGCCAAACCACCAGC | +G*+G*+T*G*C*C*A*A*A*C*C*A*C*C*+A*+G*+C |
| 42 | A24039He | GGAGCGGAAGTACTGGC | +G*+G*+A*+G*C*G*G*A*A*G*T*A*C*T*+G*+G*+C |
| 43 | A24040He | ATGGAGCGGAAGTACTG | +A*+T*+G*G*A*G*C*G*G*A*A*G*T*+A*+C*+T*+G |
| 44 | A24041He | GGATGGAGCGGAAGTAC | +G*+G*+A*+T*G*G*A*G*C*G*G*A*A*G*+T*+A*+C |
| 45 | A24042He | GGCTGGATCAACATGGT | +G*+G*+C*T*G*G*A*T*C*A*A*C*A*T*+G*+G*+T |
| 46 | A24043He | ATGTGACTGAGTCCGCC | +A*+T*+G*T*G*A*C*T*G*A*G*T*C*C*+G*+C*+C |
| 47 | A24044He | CAATGTGACTGAGTCCG | +C*+A*+A*+T*G*T*G*A*C*T*G*A*G*T*+C*+C*+G |
| 48 | A24046He | GAACTCTGTGAGCTCCG | +G*+A*+A*C*T*C*T*G*T*G*A*G*C*T*C*C*+G |
| 49 | A24063Hi | CTGGTGGACTAACACAC | +C*+T*+G*G*T*G*G*A*C*T*A*A*C*A*+C*+A*+C |

TABLE 1-continued

List of antisense oligonucleotides hybridizing with human ANGPLT4 mRNA and/or pre-mRNA for example of SEQ ID NO. 1 and/or SEQ ID NO. 2;

| Seq ID | Antisense Name | Antisense Sequence 5'-3' | Antisense Sequence 5'-3' with PTO (*) and LNA (+) |
|---|---|---|---|
| 50 | A24064Hi | TGGACCTGACAAGGAGA | +T*+G*+G*A*C*C*T*G*A*C*A*A*G*G*+A*+G*+A |
| 51 | A24065Hi | CACACGGCATGTAAGG | +C*+A*+C*A*C*G*G*C*A*T*G*T*A*+A*+G*+G |
| 4 | A24066Hi | GCCAGATAGGCTAAGTT | +G*+C*+C*A*G*A*T*A*G*G*C*T*A*A*+G*+T*+T |
| 52 | A24067Hi | AGGCTAGTCTCGACAGC | +A*+G*+G*C*T*A*G*T*C*T*C*G*A*C*+A*+G*+C |
| 8 | A24068Hi | GATCCTCATGATAGGCC | +G*+A*+T*C*C*T*C*A*T*G*A*T*A*G*+G*+C*+C |
| 53 | A24069Hi | GATCGCAGTGCCGCAAT | +G*+A*+T*C*G*C*A*G*T*G*C*C*G*C*+A*+A*+T |
| 53 | A24070Hi | GATCGCAGTGCCGCAAT | +G*A*T*C*G*C*A*G*T*G*C*C*G*C*+A*+A*+T |
| 54 | A24071Hi | CGTGTTGTAACCTCTTG | +C*+G*+T*G*T*T*G*T*A*A*C*C*T*C*+T*+T*+G |
| 55 | A24072Hi | GATCGCAGTGCCGCA | +G*+A*+T*C*G*C*A*G*T*G*C*C*+G*+C*+A |
| 55 | A24073Hi | GATCGCAGTGCCGCA | +G*+A*+T*C*G*C*A*G*T*G*C*C*G*+C*+A |
| 56 | A24074Hi | GGATCGCAGTGCCGC | +G*+G*+A*T*C*G*C*A*G*T*G*C*+C*+G*+C |
| 5 | A24075He | CTGGAAAGAATCGGATC | +C*+T*+G*G*A*A*A*G*A*A*T*C*G*G*+A*+T*+C |
| 47 | A24076He | CAATGTGACTGAGTCCG | +C*+A*+A*T*G*T*G*A*C*T*G*A*G*T*+C*+C*+G |
| 47 | A24077He | CAATGTGACTGAGTCCG | +C*+A*+A*T*G*T*G*A*C*T*G*A*G*+T*+C*+C*+G |
| 57 | Neg1 | | +C*+G*+T*T*T*A*G*G*C*T*A*T*G*T*A*+C*+T*+T |

Neg1 is an oligonucleotide representing a negative control which is not hybridizing with ANGPTL4 of SEQ ID NO. 1 or SEQ ID NO. 2.
"He" means "human exonic region" and is an oligonucleotide primarily hybridizing with mRNA of human ANGPTL4, and
"Hi" is an oligonucleotide hybridizing with introns of ANGPTL4 pre-mRNA.

ANGPTL4 oligonucleotides of Table 2 also hybridize with mRNA and/or pre-m RNA of human ANGPTL4:

TABLE 2

List of antisense oligonucleotides hybridizing with human ANGPLT4 mRNA and/or pre-mRNA for example of SEQ ID NO. 1 and/or SEQ ID NO. 2;

| Seq ID | Antisense Name | Antisense Sequence 5'-3' | Antisense Sequence 5'-3' with PTO (*) and LNA (+) |
|---|---|---|---|
| 154 | A24078Hi | CACCGGAGAGCATCGA | +C*+A*+C*C*G*G*A*G*A*G*C*A*T*+C*+G*+A |
| 155 | A24079Hi | CACGGCATGTAAGGAAG | +C*+A*+C*G*G*C*A*T*G*T*A*A*G*G*+A*+A*+G |
| 156 | A24080Hi | ACACACGGCATGTAAGG | +A*+C*+A*C*A*C*G*G*C*A*T*G*T*A*+A*+G*+G |
| 157 | A24081Hi | TAGTCTCGACAGCAGGT | +T*+A*+G*T*C*T*C*G*A*C*A*G*C*A*+G*+G*+T |
| 158 | A24082Hi | GGTTCGAGATGAACGGA | +G*+G*+T*T*C*G*A*G*A*T*G*A*A*C*+G*+G*+A |
| 159 | A24083Hi | TCGAGATGAACGGAGA | +T*+C*+G*A*G*A*T*G*A*A*C*G*G*+A*+G*+A |
| 160 | A24084Hi | TCTGCATCGGACACACG | +T*+C*+T*G*C*A*T*C*G*G*A*C*A*C*+A*+C*+G |
| 161 | A24085Hi | AACTTAGAGAACCGCGA | +A*+A*+C*T*T*A*G*A*G*A*A*C*C*G*+C*+G*+A |
| 162 | A24086Hi | GCCGTGAACTTAGAGAA | +G*+C*+C*G*T*G*A*A*C*T*T*A*G*A*+G*+A*+A |
| 163 | A24087Hi | TTAGAGAACCGCGAGT | +T*+T*+A*G*A*G*A*A*C*C*G*C*G*+A*+G*+T |
| 164 | A24088Hi | TGACCAGGAAGACGCTT | +T*+G*+A*C*C*A*G*G*A*A*G*A*C*G*+C*+T*+T |
| 165 | A24089Hi | TCGAAATGAGTCTGCAC | +T*+C*+G*A*A*A*T*G*A*G*T*C*T*G*+C*+A*+C |

TABLE 2-continued

List of antisense oligonucleotides hybridizing with
human ANGPLT4 mRNA and/or pre-mRNA for example of
SEQ ID NO. 1 and/or SEQ ID NO. 2;

| Seq ID | Name | Antisense Sequence 5'-3' | Antisense Sequence 5'-3' with PTO (*) and LNA (+) |
|---|---|---|---|
| 166 | A24090Hi | CGTTGAGCACGTCTGGA | +C*+G*+T*T*G*A*G*C*A*C*G*T*C*T*+G*+G*+A |
| 167 | A24091Hi | CGTTGAGCACGTCTGG | +C*+G*+T*T*G*A*G*C*A*C*G*T*C*+T*+G*+G |
| 168 | A24092Hi | CACACGTCCAGTTCTCA | +C*+A*+C*A*C*G*T*C*C*A*G*T*T*C*+T*+C*+A |
| 169 | A24093Hi | GCGGATCGGTCAGGAGT | +G*+C*+G*G*A*T*C*G*G*T*C*A*G*G*+A*+G*+T |
| 170 | A24094Hi | TACCACACACCGTCCTG | +T*+A*+C*C*A*C*A*C*A*C*C*G*T*C*+C*+T*+G |
| 171 | A24095Hi | CCTTGTACCACACACCG | +C*+C*+T*T*G*T*A*C*C*A*C*A*C*A*+C*+C*+G |
| 172 | A24096Hi | TTGTACCACACACCGT | +T*+T*+G*T*A*C*C*A*C*A*C*A*C*+C*+G*+T |
| 173 | A24097Hi | CTTAACAGTGGATGACC | +C*+T*+T*A*A*C*A*G*T*G*G*A*T*G*+A*+C*+C |
| 174 | A24098He | CGAGGACGGTTTTTAT | +C*+G*+A*+G*G*A*C*G*G*T*T*T*T*+T*+A*+T |
| 175 | A24099He | AGGATCCGCTCAGCTCG | +A*+G*+A*T*C*C*G*C*T*C*A*G*C*+T*+C*+G |
| 176 | A24100He | TCGTGTGAGGATCCGCT | +T*+C*+G*T*G*T*G*A*G*G*A*T*C*C*+G*+C*+T |
| 177 | A24101He | AATCGGATCACAGTCGT | +A*+A*+T*C*G*G*A*T*C*A*C*A*G*T*+C*+G*+T |
| 178 | A24102He | TAGCACGGCGGTGGCGG | +T*+A*+G*C*A*C*G*G*C*G*G*T*G*G*+C*+G*+G |
| 179 | A24103He | TAGCACGGCGGTGGCG | +T*+A*+G*C*A*C*G*G*C*G*G*T*G*+G*+C*+G |
| 180 | A24104He | GCGGCGACTTGGACTG | +G*+C*+G*G*C*G*A*C*T*T*G*G*A*+C*+T*+G |
| 181 | A24105He | GGACGCAAAGCGCGGC | +G*+G*+A*C*G*C*A*A*A*G*C*G*C*+G*+G*+C |
| 182 | A24106He | AGGACGCAAAGCGCGG | +A*+G*+G*A*C*G*C*A*A*A*G*C*G*+C*+G*+G |
| 183 | A24107He | GCGGCTGACATTGTGAG | +G*+C*+G*G*C*T*G*A*C*A*T*T*G*T*+G*+A*+G |
| 184 | A24108He | ATAGGCCGTGTCCTCGC | +A*+T*+A*G*G*C*C*G*T*G*T*C*C*T*+C*+G*+C |
| 185 | A24109He | TATAGGCCGTGTCCTCG | +T*+A*+T*A*G*G*C*C*G*T*G*T*C*C*+T*+C*+G |
| 186 | A24110He | AGTACTGGCCGTTGAGG | +A*+G*+T*A*C*T*G*G*C*C*G*T*T*G*+A*+G*+G |
| 187 | A24111He | GAAGTACTGGCCGTTGA | +G*+A*+A*G*T*A*C*T*G*G*C*C*G*T*+T*+G*+A |
| 188 | A24112He | TCTTAAGCTTCTGCCGC | +T*+C*+T*T*A*A*G*C*T*T*C*T*G*C*+C*+G*+C |
| 189 | A24113He | AGTCACCGTCTTTCGTG | +A*+G*+T*C*A*C*C*G*T*C*T*T*T*C*+G*+T*+G |
| 190 | A24114He | CGCCATTGAGGCCAGTC | +C*+G*+C*C*A*T*T*G*A*G*G*C*C*A*+G*+T*+C |
| 191 | A24115He | CTGAGTCCGCCATTGAG | +C*+T*+G*A*G*T*C*C*G*C*C*A*T*T*+G*+A*+G |
| 192 | A24116He | ATTGGCGCCTGCTTGTG | +A*+T*+T*G*G*C*G*C*C*T*G*C*T*T*+G*+T*+G |
| 193 | A24117He | ATACCATTGGCGCCTGC | +A*+T*+A*C*C*A*T*T*G*G*C*G*C*C*+T*+G*+C |
| 190 | A24118He | CGCCATTGAGGCCAGTC | +C*+G*+C*C*A*T*T*G*A*G*G*C*C*A*+G*+T*+C |
| 194 | A24119He | TGAGTCCGCCATTGAGG | +T*+G*+A*G*T*C*C*G*C*C*A*T*T*G*+A*+G*+G |
| 191 | A24120He | CTGAGTCCGCCATTGAG | +C*+T*+G*A*G*T*C*C*G*C*C*A*T*T*+G*+A*+G |
| 195 | A24121He | ACTGAGTCCGCCATTGA | +A*+C*+T*G*A*G*T*C*C*G*C*C*A*T*+T*+G*+A |
| 196 | A24122HMe | TGACTGAGTCCGCCATT | +T*+G*+A*C*T*G*A*G*T*C*C*G*C*C*+A*+T*+T |
| 197 | A24123He | TGTGACTGAGTCCGCCA | +T*+G*+T*G*A*C*T*G*A*G*T*C*C*G*+C*+C*+A |
| 46 | A24124He | ATGTGACTGAGTCCGCC | +A*+T*+G*T*G*A*C*T*G*A*G*T*C*C*+G*+C*+C |
| 198 | A24125He | CCCCGTCAGTCAATGTG | +C*+C*+C*C*G*T*C*A*G*T*C*A*A*T*+G*+T*+G |

TABLE 2-continued

List of antisense oligonucleotides hybridizing with
human ANGPLT4 mRNA and/or pre-mRNA for example of
SEQ ID NO. 1 and/or SEQ ID NO. 2;

| Seq ID | Name | Antisense Sequence 5'-3' | Antisense Sequence 5'-3' with PTO (*) and LNA (+) |
|---|---|---|---|
| 199 | A24126He | GGTCCCCGTCAGTCAAT | +G*+G*+T*C*C*C*C*G*T*C*A*G*T*C*+A*+A*+T |
| 57 | Neg1 | | +C*+G*+T*T*T*A*G*G*C*T*A*T*G*T*A*+C*+T*+T |
| 249 | R01002 | | +T*+A*+C*G*C*G*C*G*T*T*G*T*+T*+T*+A |
| 250 | R01009 | | +T*+T*+A*G*C*G*C*G*C*G*A*A*T*+A*+T*+G |
| 251 | R01014 | | +C*+G*+A*A*T*A*A*C*C*G*T*C*G*T*+G*+T*+T |
| 252 | R01019 | | +G*+A*+C*T*C*G*T*T*A*A*A*C*C*G*+A*+T*+A |

Neg1, R01002, R01009, R01014 and R01019 are oligonucleotides representing negative controls which are not hybridizing with ANGPTL4 of SEQ ID NO. 1 or SEQ ID NO. 2.
"He" means "human exonic region" and is an oligonucleotide primarily hybridizing with mRNA of human ANGPTL4, and
"Hi" is an oligonucleotide hybridizing with introns of ANGPTL4 pre-mRNA.
"HMe" indicates an oligonucleotide hybridizing with "human and mouse exonic region" of ANGPTL4.

Oligonucleotides of Table 3 hybridize particularly with mRNA and/or pre-m RNA of mouse ANGPTL4:

TABLE 3

List of antisense oligonucleotides hybridizing with
mouse ANGPLT4 mRNA and/or pre-mRNA for example of
SEQ ID NO. 58 and/or SEQ ID NO. 59;

| Seq ID | Name | Antisense Sequence 5'-3' | Antisense Sequence 5'-3' with PTO (*) and LNA (+) |
|---|---|---|---|
| 60 | A24001M | GTTGCACCTAAAGCC | +G*+T*+T*G*C*A*C*C*T*A*A*A*+G*+C*+C |
| 61 | A24002M | ACGGTTGCACCTAAAGC | +A*+C*+G*G*T*T*G*C*A*C*C*T*A*A*+A*+G*+C |
| 62 | A24003M | ACGGTTGCACCTAAAG | +A*+C*+G*G*T*T*G*C*A*C*C*T*A*+A*+A*+G |
| 63 | A24004M | TCACGGTTGCACCTAA | +T*+C*+A*C*G*G*T*T*G*C*A*C*C*+T*+A*+A |
| 64 | A24005M | TTCACGGTTGCACCTA | +T*+T*+C*A*C*G*G*T*T*G*C*A*C*+C*+T*+A |
| 65 | A24006M | ATAAGCGTTTCACGGTT | +A*+T*+A*A*G*C*G*T*T*T*C*A*C*G*+G*+T*+T |
| 66 | A24007M | CATAAGCGTTTCACGGT | +C*+A*+T*A*A*G*C*G*T*T*T*C*A*C*+G*+G*+T |
| 67 | A24008M | CGTAGCTCATAAGCGTT | +C*+G*+T*A*G*C*T*C*A*T*A*A*G*C*+G*+T*+T |
| 68 | A24009M | GCTAGGACTCCGGAAC | +G*+C*+T*A*G*G*A*C*T*C*C*G*G*+A*+A*+C |
| 69 | A24010M | ACGCTAGGACTCCGGAA | +A*+C*+G*C*T*A*G*G*A*C*T*C*C*G*+G*+A*+A |
| 70 | A24011M | AACGCTAGGACTCCG | +A*+A*+C*G*C*T*A*G*G*A*C*T*+C*+C*+G |
| 71 | A24012M | AGCGCATGATTCTGG | +A*G*+C*G*C*A*T*G*A*T*T*C*+T*G*+G |
| 72 | A24013M | CGGAGCGCAGCGCATGA | +C*G*+G*A*G*C*G*C*A*G*C*G*C*A*+T*G*+A |
| 73 | A24014M | AGCCGCGCATAGCACCA | +A*+G*+C*C*G*C*G*C*A*T*A*G*C*A*+C*+C*+A |
| 74 | A24015M | TAGCCGCGCATAGCAC | +T*+A*+G*C*C*G*C*G*C*A*T*A*G*+C*+A*+C |
| 75 | A24016M | AGTAGCCGCGCATAGCA | +A*+G*+T*A*G*C*C*G*C*G*C*A*T*A*+G*+C*+A |
| 76 | A24017M | CAGTAGCCGCGCATAGC | +C*+A*+G*T*A*G*C*C*G*C*G*C*A*T*+A*+G*+C |
| 77 | A24018M | CAGTAGCCGCGCATAG | +C*+A*+G*T*A*G*C*C*G*C*G*C*A*+T*+A*+G |
| 78 | A24019M | GCAGTAGCCGCGCATA | +G*+C*+A*G*T*A*G*C*C*G*C*G*C*+A*+T*+A |
| 79 | A24020M | CCTTGCGCGCTCAAA | +C*+C*T*T*G*C*G*C*G*C*T*C*+A*+A*+A |
| 80 | A24021M | GATGCAAAGCGCGGTG | +G*+A*+T*G*C*A*A*A*G*C*G*C*G*+G*+T*+G |

TABLE 3-continued

List of antisense oligonucleotides hybridizing with mouse ANGPLT4 mRNA and/or pre-mRNA for example of SEQ ID NO. 58 and/or SEQ ID NO. 59;

| Seq ID | Antisense Name | Antisense Sequence 5'-3' | Antisense Sequence 5'-3' with PTO (*) and LNA (+) |
|---|---|---|---|
| 81 | A24022M | AGGATGCAAAGCGCGGT | +A*+G*+G*A*T*G*C*A*A*A*G*C*G*C*+G*+G*+T |
| 82 | A24023M | CCACGTGTTCGCGCAG | +C*+C*+A*C*G*T*G*T*T*C*G*C*G*+C*+A*+G |
| 83 | A24024M | CTCCACGTGTTCGCGCA | +C*+T*+C*C*A*C*G*T*G*T*T*C*G*C*+G*+C*+A |
| 84 | A24025M | TGCGCTCCACGTGTTCG | +T*+G*+C*G*C*T*C*C*A*C*G*T*G*T*+T*+C*+G |
| 85 | A24026M | TGCGCTCCACGTGTTC | +T*+G*+C*G*C*T*C*C*A*C*G*T*G*+T*+T*+C |
| 86 | A24027M | TGCGCTCCACGTGTT | +T*+G*+C*G*C*T*C*C*A*C*G*T*+G*+T*+T |
| 87 | A24028M | ATGCGGCGCTCCAGCG | +A*+T*G*C*G*G*C*G*C*T*C*C*A*G*C*+G |
| 88 | A24029M | CTGACAAGCGTTACCAC | +C*+T*+G*A*C*A*A*G*C*G*T*T*A*C*+C*+A*+C |
| 89 | A24030M | CCTGACAAGCGTTACCA | +C*+C*+T*G*A*C*A*A*G*C*G*T*T*A*+C*+C*+A |
| 90 | A24031M | CCTGACAAGCGTTAC | +C*+C*+T*G*A*C*A*A*G*C*G*T*+T*+A*+C |
| 91 | A24032M | ATTGTCTAGGTGCGTG | +A*+T*+T*G*T*C*T*A*G*G*T*G*C*+G*+T*+G |
| 92 | A24033M | CCATTGTCTAGGTGCGT | +C*+C*+A*T*T*G*T*C*T*A*G*G*T*G*+C*+G*+T |
| 93 | A24034M | CGTTCAGGCGTCTCTGA | +C*G*+T*T*C*A*G*G*C*G*T*C*T*C*+T*G*+A |
| 94 | A24035M | AGAGCCGTTCAGGCGT | +A*+G*+A*G*C*C*G*T*T*C*A*G*G*+C*G*+T |
| 95 | A24036M | GCTCATTGGCCGTGG | +G*C*+T*C*A*T*T*G*G*C*C*G*+T*G*+G |
| 96 | A24037M | AGTGGAAGTATTGTCCA | +A*+G*T*G*G*A*A*G*T*A*T*T*G*T*+C*C*+A |
| 97 | A24038M | TACGCTCCTGCCGTTGC | +T*+A*+C*G*C*T*C*C*T*G*C*C*G*T*+T*+G*+C |
| 98 | A24039M | TTACGCTCCTGCCGTTG | +T*+T*+A*C*G*C*T*C*C*T*G*C*C*G*+T*+T*+G |
| 99 | A24040M | TTTTACGCTCCTGCCG | +T*+T*+T*T*T*A*C*G*C*T*C*C*T*G*+C*+C*+G |
| 100 | A24041M | TTTTACGCTCCTGCC | +T*+T*+T*T*A*C*G*C*T*C*C*T*+G*+C*+C |
| 101 | A24042M | AGAGGATAGTAGCGGCC | +A*+G*A*G*G*A*T*A*G*T*A*G*C*G*G*+C*+C |
| 102 | A24043M | ACAAGACGCAGATAGCC | +A*+C*+A*A*G*A*C*G*C*A*G*A*T*A*+G*+C*+C |
| 103 | A24044M | GGCGAGAAGTGATATTC | +G*+G*+C*G*A*G*A*A*G*T*G*A*T*A*+T*+T*+C |
| 104 | A24045M | TAGGCGAGAAGTGATAT | +T*+A*+G*G*C*G*A*G*A*A*G*T*G*A*+T*+A*+T |
| 105 | A24046M | GTAGGCGAGAAGTGAT | +G*+T*+A*G*G*C*G*A*G*A*A*G*T*+G*+A*+T |
| 106 | A24047M | GAGTCCGCCATTAAGG | +G*+A*+G*T*C*C*G*C*C*A*T*T*A*+A*+G*+G |
| 107 | A24048M | ACTGAGTCCGCCATTAA | +A*+C*+T*G*A*G*T*C*C*G*C*C*A*T*+T*+A*+A |
| 108 | A24049M | ATATGACTGAGTCCGCC | +A*+T*+A*T*G*A*C*T*G*A*G*T*C*C*+G*+C*+C |
| 109 | A24050M | AATATGACTGAGTCCGC | +A*+A*+T*A*T*G*A*C*T*G*A*G*T*+C*+C*+G*+C |
| 110 | A24051M | CGCTAGGACTCCGGAA | +C*+G*C*T*A*G*G*A*C*T*C*C*G*+G*+A*+A |
| 111 | A24052M | AACGCTAGGACTCCGGA | +A*+A*C*G*C*T*A*G*G*A*C*T*C*C*G*+G*+A |
| 112 | A24053M | AACGCTAGGACTCCGG | +A*+A*+C*G*C*T*A*G*G*A*C*T*C*C*+G*+G |
| 113 | A24054M | CAACGCTAGGACTCCG | +C*+A*+A*+C*G*C*T*A*G*G*A*C*T*+C*+C*+G |
| 114 | A24055M | GCAACGCTAGGACTCCG | +G*+C*+A*+A*C*G*C*T*A*G*G*A*C*T*+C*+C*+G |
| 115 | A24056M | GTAGCCGCGCATAGC | +G*+T*+A*G*C*C*G*C*G*C*A*T*+A*+G*+C |
| 116 | A24057M | AGTAGCCGCGCATAGC | +A*+G*+T*A*G*C*C*G*C*G*C*A*T*+A*+G*+C |

TABLE 3-continued

List of antisense oligonucleotides hybridizing with
mouse ANGPLT4 mRNA and/or pre-mRNA for example of
SEQ ID NO. 58 and/or SEQ ID NO. 59;

| Seq ID | Antisense Name | Antisense Sequence 5'-3' | Antisense Sequence 5'-3' with PTO (*) and LNA (+) |
|---|---|---|---|
| 117 | A24058M | AGTAGCCGCGCATAG | +A*+G*+T*A*G*C*C*G*C*G*C*A*+T*+A*+G |
| 118 | A24059M | GCAGTAGCCGCGCATAG | +G*+C*+A*G*T*A*G*C*C*G*C*G*C*A*+T*+A*+G |
| 118 | A24060M | GCAGTAGCCGCGCATAG | +G*+C*+A*+G*T*A*G*C*C*G*C*G*C*A*+T*+A*+G |
| 119 | A24061M | CAGTAGCCGCGCATA | +C*+A*+G*T*A*G*C*C*G*C*G*C*+A*+T*+A |
| 120 | A24062M | CCGCAGTAGCCGCGCAT | +C*C*G*C*A*G*T*A*G*C*C*G*C*G*+C*+A*+T |
| 121 | A24063M | CCTTGCGCGCTCAAAA | +C*C*+T*T*G*C*G*C*G*C*T*C*A*A*+A*+A |
| 122 | A24064M | CCTTGCGCGCTCAAAA | +C*+C*T*T*G*C*G*C*G*C*T*C*A*+A*+A*+A |
| 79 | A24065M | CCTTGCGCGCTCAAA | +C*+C*+T*T*G*C*G*C*G*C*T*C*+A*+A*+A |
| 123 | A24066M | ATGCAAAGCGCGGTGG | +A*+T*+G*C*A*A*A*G*C*G*C*G*+G*+T*+G*+G |
| 124 | A24067M | ATGCAAAGCGCGGTG | +A*+T*+G*C*A*A*A*G*C*G*C*G*+G*+T*+G |
| 125 | A24068M | CGCTCCACGTGTTCG | +C*G*+C*T*C*C*A*C*G*T*G*T*+T*+C*+G |
| 126 | A24069M | GCGCTCCACGTGTTCG | +G*+C*G*C*T*C*C*A*C*G*T*G*T*+T*+C*+G |
| 127 | A24070M | TGAGTCCGCCATTAAGG | +T*+G*+A*+G*T*C*C*G*C*C*A*T*T*A*+A*+G*+G |
| 128 | A24071M | ATGACTGAGTCCGCCA | +A*T*G*A*C*T*G*A*G*T*C*C*G*+C*+C*+A |
| 129 | A24072M | TATGACTGAGTCCGCC | +T*+A*+T*G*A*C*T*G*A*G*T*C*+G*+C*+C |
| 130 | A24073M | AATATGACTGAGTCCGC | +A*+A*+T*+A*T*G*A*C*T*G*A*G*T*+C*+C*+G*+C |
| 131 | A24074M | AATATGACTGAGTCCG | +A*+A*+T*A*T*G*A*C*T*G*A*G*T*+C*+C*+G |
| 132 | A24075Mi | CCTAGTAGATGCGCCTA | +C*+C*+T*A*G*T*A*G*A*T*G*C*G*C*C*+T*+A |
| 133 | A24076Mi | TCGTTAGTCTAAGTAGA | +T*+C*+G*T*T*A*G*T*C*T*A*A*G*T*+A*+G*+A |
| 134 | A24077Mi | AGTACTAGACTCGTTAG | +A*+G*+T*A*C*T*A*G*A*C*T*C*G*T*+T*+A*+G |
| 135 | A24078Mi | TCGGCAACCTCCTCTTA | +T*+C*+G*G*C*A*A*C*C*T*C*C*T*C*+T*+T*+A |
| 136 | A24079Mi | GCTTTATGTCGGCAACC | +G*+C*+T*T*T*A*T*G*T*C*G*G*C*A*+A*+C*+C |
| 137 | A24080Mi | TTGACTCATGCCATAAC | +T*+T*+G*A*C*T*C*A*T*G*C*C*A*T*+A*+A*+C |
| 138 | A24081Mi | GTTAACGGCTAATAAGA | +G*+T*+T*A*A*C*G*G*C*T*A*A*T*A*+A*+G*+A |
| 139 | A24082Mi | TCTGGTTAACGGCTAAT | +T*+C*+T*G*G*T*T*A*A*C*G*G*C*T*+A*+A*+T |
| 140 | A24083Mi | ACTTTAGCTCCTTATGA | +A*+C*+T*T*T*A*G*C*T*C*C*T*T*A*+T*+G*+A |
| 141 | A24084Mi | GATCGAAACTGTTATGT | +G*+A*+T*C*G*A*A*A*C*T*G*T*T*+A*+T*+G*+T |
| 141 | A24085Mi | AGAACCTATGCCTGCCG | +A*+G*+A*A*C*C*T*A*T*G*C*C*T*G*C*+C*+G |
| 142 | A24086Mi | TCCTCTCATCCAATCGG | +T*+C*+C*T*C*T*C*A*T*C*C*A*A*T*+C*+G*+G |
| 143 | A24087Mi | ACGGCTATGTCTGTTAC | +A*+C*+G*G*C*T*A*T*G*T*C*T*G*T*+T*+A*+C |
| 144 | A24088Mi | GGACCTGTAACCACCTA | +G*+G*+A*C*C*T*G*T*A*A*C*C*A*C*+C*+T*+A |
| 145 | A24089Mi | GTATTGTCGCTGATGAA | +G*+T*+A*T*T*G*T*C*G*C*T*G*A*T*+G*+A*+A |
| 146 | A24090Mi | GATTTGCCTAAACTCGT | +G*+A*+T*T*T*G*C*C*T*A*A*A*C*T*+C*+G*+T |
| 147 | A24091Mi | GAGCTTGCGATGCCTGT | +G*A*+G*C*T*T*G*C*G*A*T*G*C*C*T*+G*+T |
| 148 | A24092Mi | GTAGATGACTAGGCCTG | +G*+T*+A*G*A*T*G*A*C*T*A*G*G*C*C*+T*+G |
| 149 | A24093Mi | TCAATGGAAGCGCTTTA | +T*+C*+A*A*T*G*G*A*A*G*C*G*C*T*+T*+T*+A |
| 150 | A24094Mi | GTAGCAGACTTGCACTA | +G*+T*+A*G*C*A*G*A*C*T*T*G*C*A*+C*+T*+A |

TABLE 3-continued

List of antisense oligonucleotides hybridizing with
mouse ANGPLT4 mRNA and/or pre-mRNA for example of
SEQ ID NO. 58 and/or SEQ ID NO. 59;

| Seq ID | Antisense Name | Antisense Sequence 5'-3' | Antisense Sequence 5'-3' with PTO (*) and LNA (+) |
| --- | --- | --- | --- |
| 151 | A24095Mi | CTCATGTTAGGTAGGTT | +C*+T*+C*A*T*G*T*T*A*G*G*T*A*G*+G*+T*+T |
| 152 | A24096Mi | ACGTGGCCAAAGACAAT | +A*+C*+G*T*G*G*C*C*A*A*A*G*A*C*+A*+A*+T |
| 57 | Neg1 |  | +C*+G*+T*T*T*A*G*G*C*T*A*T*G*T*A*+C*+T*+T |

Neg1 is an oligonucleotide representing a negative control which is not hybridizing with ANGPLT4 of SEQ ID NO. 58 or SEQ ID NO. 59.
Oligonucleotides primarily hybridizing with mouse ANGPLT4 mRNA are indicated by "M", and oligonucleotides primarily hybridizing with mouse ANGPLT4 pre-mRNA are indicated by "Mi" as the oligonucleotides hybridize with an intron.

Oligonucleotides of Table 4 also hybridize particularly with mRNA and/or pre-m RNA of mouse ANGPTL4:

TABLE 4

List of antisense oligonucleotides hybridizing with
mouse ANGPLT4 mRNA and/or pre-mRNA for example of
SEQ ID NO. 58 and/or SEQ ID NO. 59;

| Seq ID | Antisense Name | Antisense Sequence 5'-3' | Antisense Sequence 5'-3' with PTO (*) and LNA (+) |
| --- | --- | --- | --- |
| 200 | A24097M | TTCACGGTTGCACCTAA | +T*+T*+C*A*C*G*G*T*T*G*C*A*C*C*+T*+A*+A |
| 201 | A24098M | ATAAGCGTTTCACGGT | +A*+T*+A*A*G*C*G*T*T*T*C*A*C*+G*+G*+T |
| 202 | A24099M | GCTAGGACTCCGGAACG | +G*+C*+T*A*G*G*A*C*T*C*C*G*G*A*+A*+C*+G |
| 203 | A24100M | CAGCAACGCTAGGACTC | +C*+A*+G*C*A*A*C*G*C*T*A*G*G*A*+C*+T*+C |
| 204 | A24101M | GTGCAGCAACGCTAGGA | +G*+T*+G*C*A*G*C*A*A*C*G*C*T*A*+G*+G*+A |
| 205 | A24102M | CCGCGCATAGCACCAGG | +C*+C*+G*C*G*C*A*T*A*G*C*A*C*C*+A*+G*+G |
| 206 | A24103M | ATGCAAAGCGCGGTGGC | +A*+T*+G*C*A*A*A*G*C*G*C*G*G*T*+G*+G*+C |
| 207 | A24104M | CCACGTGTTCGCGCAGC | +C*+C*+A*C*G*T*G*T*T*C*G*C*G*C*+A*+G*+C |
| 208 | A24105M | AGCGTTACCACAGGCAG | +A*+G*+C*G*T*T*A*C*C*A*C*A*G*G*+C*+A*+G |
| 209 | A24106M | TCTATCCTCGGAGTCTT | +T*+C*+T*A*T*C*C*T*C*G*G*A*G*T*+C*+T*+T |
| 210 | A24107M | CTCGAAGTCTTGTCTAC | +C*+T*+C*G*A*A*G*T*C*T*T*G*T*C*+T*+A*+C |
| 211 | A24108M | GAAGTATTGTCCATTGA | +G*+A*+A*G*T*A*T*T*G*T*C*C*A*T*+T*+G*+A |
| 212 | A24109M | CAGAGGATAGTAGCGGC | +C*+A*+G*A*G*G*A*T*A*G*T*A*G*C*+G*+G*+C |
| 213 | A24110M | CAGTCTCTCCAGTTACG | +C*+A*+G*T*C*T*C*T*C*C*A*G*T*T*+A*+C*+G |
| 214 | A24111M | GCGAGAAGTGATATTC | +G*+C*+G*A*G*A*A*G*T*G*A*T*A*+T*+T*+C |
| 107 | A24112M | ACTGAGTCCGCCATTAA | +A*+C*+T*G*A*G*T*C*C*G*C*C*A*T*+T*+A*+A |
| 108 | A24113M | ATATGACTGAGTCCGCC | +A*+T*+A*T*G*A*C*T*G*A*G*T*C*C*+G*+C*+C |
| 215 | A24114M | TCAATATGACTGAGTCC | +T*+C*+A*A*T*A*T*G*A*C*T*G*A*G*+T*+C*+C |
| 216 | A24115M | TCCAGTCAGTCAATATG | +T*+C*+C*A*G*T*C*A*G*T*C*A*A*T*+A*+T*+G |
| 217 | A24116M | CTCCAGTCAGTCAATAT | +C*+T*+C*C*A*G*T*C*A*G*T*C*A*A*+T*+A*+T |
| 218 | A24117Mi | GAGTCCTAGTAGATGCG | +G*+A*+G*T*C*C*T*A*G*T*A*G*A*T*+G*+C*+G |
| 219 | A24118Mi | GTTAGTCTAAGTAGAGT | +G*+T*+T*A*G*T*C*T*A*A*G*T*A*G*+A*+G*+T |
| 220 | A24119Mi | AGTACTAGACTCGTTA | +A*+G*+T*A*C*T*A*G*A*C*T*C*G*+T*+T*+A |
| 221 | A24120Mi | GCAACCTCCTCTTATTC | +G*+C*+A*A*C*C*T*C*C*T*C*T*T*A*+T*+T*+C |

TABLE 4-continued

List of antisense oligonucleotides hybridizing with mouse ANGPLT4 mRNA and/or pre-mRNA for example of SEQ ID NO. 58 and/or SEQ ID NO. 59;

| Seq ID | Antisense Name | Antisense Sequence 5'-3' | Antisense Sequence 5'-3' with PTO (*) and LNA (+) |
|---|---|---|---|
| 222 | A24121Mi | AAGATATGCAAGGCTAG | +A*+A*+G*A*T*A*T*G*C*A*A*G*G*C*+T*+A*+G |
| 223 | A24122Mi | GACTCATGCCATAACAA | +G*+A*+C*T*C*A*T*G*C*C*A*T*A*A*+C*+A*+A |
| 224 | A24123Mi | GTGGACCTGACAAGAAG | +G*+T*+G*G*A*C*C*T*G*A*C*A*A*G*+A*+A*+G |
| 225 | A24124Mi | AACGGCTAATAAGATTT | +A*+A*+C*G*G*C*T*A*A*T*A*A*G*A*+T*+T*+T |
| 226 | A24125Mi | GTTCTGGTTAACGGCTA | +G*+T*+T*C*T*G*G*T*T*A*A*C*G*G*+C*+T*+A |
| 227 | A24126Mi | GGTGTGCTTACTCTGGT | +G*+G*+T*G*T*G*C*T*T*A*C*T*C*T*+G*+G*+T |
| 228 | A24127Mi | CCTAGAAATTGTGATCG | +C*+C*+T*A*G*A*A*A*T*T*G*T*G*A*+T*+C*+G |
| 229 | A24128Mi | AACGAATAGGCATGAAC | +A*+A*+C*G*A*A*T*A*G*G*C*A*T*G*+A*+A*+C |
| 230 | A24129Mi | ACTTTCACCTAGTTGGC | +A*+C*+T*T*T*C*A*C*C*T*A*G*T*T*+G*+G*+C |
| 231 | A24130Mi | CTCTACTTGGCTAGGCT | +C*+T*+C*T*A*C*T*T*G*G*C*T*A*G*+G*+C*+T |
| 232 | A24131Mi | GGTACTCTGAATTAGTA | +G*+G*+T*A*C*T*C*T*G*A*A*T*T*A*+G*+T*+A |
| 233 | A24132Mi | TGTAACCACCTAAAGCC | +T*+G*+T*A*A*C*C*A*C*C*T*A*A*A*+G*+C*+C |
| 234 | A24133Mi | AGGTATTGTCGCTGATG | +A*+G*+G*T*A*T*T*G*T*C*G*C*T*G*+A*+T*+G |
| 235 | A24134Mi | GAACAGAGGTATTGTCG | +G*+A*+A*C*A*G*A*G*G*T*A*T*T*G*+T*+C*+G |
| 236 | A24135Mi | CATGTATCACACCTTCC | +C*+A*+T*G*T*A*T*C*A*C*A*C*C*T*+T*+C*+C |
| 237 | A24136Mi | TAAACTCGTTCCTGCCT | +T*+A*+A*A*C*T*C*G*T*T*C*C*T*G*+C*+C*+T |
| 238 | A24137Mi | GCCTAAACTCGTTCCTG | +G*+C*+C*T*A*A*A*C*T*C*G*T*T*C*+C*+T*+G |
| 239 | A24138Mi | ATCTCAGGAGCTTATAC | +A*+T*+C*T*C*A*G*G*A*G*C*T*T*A*+T*+A*+C |
| 240 | A24139Mi | ACAAGCTGCATAATAGG | +A*+C*+A*A*G*C*T*G*C*A*T*A*A*T*+A*+G*+G |
| 241 | A24140Mi | TATCACTGAGCTTGCGA | +T*+A*+T*C*A*C*T*G*A*G*C*T*T*G*+C*+G*+A |
| 242 | A24141Mi | AATGGAAGCGCTTTACC | +A*+A*+T*G*G*A*A*G*C*G*C*T*T*T*+A*+C*+C |
| 243 | A24142Mi | TAGCAGACTTGCACTAT | +T*+A*+G*C*A*G*A*C*T*T*G*C*A*C*+T*+A*+T |
| 244 | A24143Mi | AGGCTCAACTCTCGCAC | +A*+G*+G*C*T*C*A*A*C*T*C*T*C*G*+C*+A*+C |
| 245 | A24144Mi | AAGAGCTAGTACTGTAG | +A*+A*+G*A*G*C*T*A*G*T*A*C*T*G*+T*+A*+G |
| 246 | A24145Mi | TATAATTTGATCCTGAC | +T*+A*+T*A*A*T*T*T*G*A*T*C*C*T*+G*+A*+C |
| 247 | A24146Mi | GGTTCTCTGCCAAATGA | +G*+G*+T*T*C*T*C*T*G*C*C*A*A*A*+T*+G*+A |
| 248 | A24147Mi | CGTGGCCAAAGACAATT | +C*+G*+T*G*G*C*C*A*A*A*G*A*C*A*+A*+T*+T |
| 151 | A24148Mi | CTCATGTTAGGTAGGTT | +C*+T*+C*A*T*G*T*T*A*G*G*T*A*G*+G*+T*+T |
| 57 | Neg1 | | +C*+G*+T*T*T*A*G*G*C*T*A*T*G*T*A*+C*+T*+T |
| 249 | R01002 | | +T*+A*+C*G*C*G*C*G*G*T*T*G*T*+T*+T*+A |
| 250 | R01009 | | +T*+T*+A*G*C*G*C*G*C*G*A*A*T*+A*+T*+G |
| 251 | R01014 | | +C*+G*+A*A*T*A*A*C*C*G*T*C*G*T*+G*+T*+T |
| 252 | R01019 | | +G*+A*+C*T*C*G*T*T*A*A*A*C*C*G*+A*+T*+A |

Neg1, R01002, R01009, R01014 and R01019 are oligonucleotides representing negative controls which are not hybridizing with ANGPLT4 of SEQ ID NO. 58 or SEQ ID NO. 59. Oligonucleotides primarily hybridizing with mouse ANGPLT4 mRNA are indicated by "M", and oligonucleotides primarily hybridizing with mouse ANGPLT4 pre-mRNA are indicated by "Mi" as the oligonucleotides hybridize with an intron.

The oligonucleotides hybridize for example within a hybridizing active area which is an area enriched for ASOs with high activity. The hybridizing active area is for example one or more region(s) on the ANGPTL4 mRNA, e.g., of SEQ ID NO.1 and/or the ANGPTL4 pre-mRNA, e.g., of SEQ ID NO.2, where hybridization with an oligonucleotide highly likely results in a potent knockdown of the ANGPTL4 expression. In the present invention surprisingly several hybridizing active areas were identified for example selected from hybridizing active areas for example selected from position 1732-1759 (e.g., A24044He, SEQ ID NO.47; A24076He, SEQ ID NO.47) of SEQ ID NO. 1 and/or from position 6603-6631 (e.g., A24022Hi, SEQ ID NO.25; A24023Hi, SEQ ID NO.26; A24071Hi, SEQ ID NO.54) of SEQ ID NO.2. Further hybridizing active areas are from position 234-261 (e.g. A24102He, SEQ ID NO.178; A24103He, SEQ ID NO.179) and/or from position 1264-1293 (e.g. A24110He, SEQ ID NO.186; A24111He, SEQ ID NO.187) of human SEQ ID NO. 1 and/or from position 2800-2872 (e.g. A24083Hi, SEQ ID NO. 159; A24085Hi, SEQ ID NO.161; A24086Hi, SEQ ID NO.162; A24087Hi, SEQ ID NO. 163) and/or from position 3415-3442 (e.g. A24089Hi, SEQ ID NO.165) and/or from position 4968-4994 (e.g. A24097Hi, SEQ ID NO. 173) of human SEQ ID NO.2. Hybridizing active areas on mouse SEQ ID NO.58 or SEQ ID NO.59 are for example from position 137-163 (e.g. A24054M, SEQ ID NO.113) and/or from position 215-299 (e.g. A24018M, SEQ ID NO.77; A24019M, SEQ ID NO.78; A24020M, SEQ ID NO.79; A24021M, SEQ ID NO.80; A24065M, SEQ ID NO.79) and/or from position 1343-1371 (e.g. A24042M, SEQ ID NO.101; A24109M, SEQ ID NO.212) and/or from position 1738-1771 (e.g. A24047M, SEQ ID NO.106; A24070M, SEQ ID NO. 127; A24072M, SEQ ID NO. 129) of SEQ ID NO.58 and/or from position 1286-1314 (e.g. A24082Mi, SEQ ID NO.139; A24125Mi, SEQ ID NO.226) and/or from position 5485-5511 (e.g. A24095Mi, SEQ ID NO.151; A24148Mi, SEQ ID NO.151) of SEQ ID NO.59.

The oligonucleotide of the present invention inhibits for example at least about 50%, 55%, 60%, 65%, 70%, 75%, 80%, 85%, 90%, 92%, 93%, 94%, 95%, 96%, 97%, 98%, 99% or 100% of ANGPTL4 such as the, e.g., human or mouse, ANGPTL4 expression. The oligonucleotide of the present invention inhibits the expression of ANGPTL4 at a nanomolar or micromolar concentration for example in a concentration range of 0.1 nM to 100 µM, 0.5 nM to 15 nM, 0.6 nM to 10 nM, 1 nM to 10 µM, 5 nM to 5 µM, 10 nM to 1 µM, 15 nM to 950 nM, 20 nM to 900 nM, 25 nM to 850 nM, 30 nM to 800 nM, 35 nM to 750 nM, 40 nM to 700 nM, 45 nM to 650 nM, 50 nM to 500 nM, or 40 nM to 150 nM, or in a concentration of 0.1, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900 or 950 nM, or 1, 10 or 100 µM.

The ANGPTL4 oligonucleotide of the present invention is for example used in a concentration range of 1 nM to 10 µM, 5 nM to 6.6 µM, 10 nM to 5 µM, 15 nM to 3 µM, 20 nM to 2.2 µM, 25 nM to 1 µM, 30 nM to 800 nM, 50 nM to 500 nM, 60 nM to 300 nM, 70 nM to 250 nM, 80 nM to 200 nM, 90 nM to 120 nM, or in a concentration of 1, 1.6, 3, 5, 8, 9, 10, 15, 20, 25, 27, 30, 40, 50, 75, 82, 100, 200, 250, 300, 500, or 740 nM, or 1, 2.2, 3, 5, 6.6 or 10 µM.

The ANGPTL4 oligonucleotide of the present invention is for example administered once or repeatedly, e.g., every 12 h, every 24 h, every 48 h for some weeks, months or years, or it is administered every week, every two weeks, every three weeks or every months or every three or six months.

In some embodiments the present invention refers to a pharmaceutical composition comprising an ANGPTL4 oligonucleotide of the present invention and a pharmaceutically acceptable carrier, excipient and/or dilutant. Optionally, the pharmaceutical composition further comprises a chemotherapeutic, another disease specific active agent such as insulin, angiotensin-converting enzyme inhibitor, angiotensin receptor blocker, another oligonucleotide not of the present invention, an antibody, a HERA fusion protein, a ligand trap, a Fab fragment, a nanobody, a BiTe and/or a small molecule which is for example effective in tumor treatment, treatment of diabetes and its side effects, treatment of a cardiovascular disease, obesity, diabetes type II, hypercholesterolemia such as homozygote familial hypercholesterolemia (HoFH), heterozygote familial hypercholesterolemia (HeFH) or dyslipidemia.

The ANGPTL4 oligonucleotide or the pharmaceutical composition of the present invention is for use in a method of preventing and/or treating a disorder for example a disorder where an ANGPTL4 imbalance is involved. Optionally, the use of the oligonucleotide or the pharmaceutical composition of the present invention in a method of preventing and/or treating a disorder is combined with radiotherapy. The radiotherapy may be further combined with a chemotherapy (e.g., platinum, gemcitabine). The disorder is for example characterized by an ANGPTL4 imbalance, i.e., the ANGPTL4 level is increased in comparison to the level in a normal, healthy cell, tissue, organ or subject. The ANGPTL4 level is for example increased by an increased ANGPTL4 expression and activity, respectively. The ANGPTL4 level is measured by any standard method such as immunohistochemistry, western blot, quantitative real time PCR or QuantiGene assay known to a person skilled in the art.

The ANGPTL4 oligonucleotide or a pharmaceutical composition of the present invention is administered locally or systemically for example orally, sublingually, nasally, subcutaneously, intravenously, intraperitoneally, intramuscularly, intratumoral, intrathecal, transdermal, and/or rectal. Alternatively or in combination ex vivo treated immune cells are administered. The ANGPTL4 oligonucleotide is administered alone or in combination with another ANGPTL4 antisense oligonucleotide of the present invention and optionally in combination with another compound such as another oligonucleotide not of the present invention, an antibody, a HERA fusion protein, a ligand trap, a Fab fragment, a nanobody, a BiTe, a small molecule and/or a chemotherapeutic (e.g., platinum, gemcitabine) and/or another disease specific agent such as insulin, angiotensin-converting enzyme inhibitor, and/or angiotensin receptor blocker.

The oligonucleotide not of the present invention, an antibody, a HERA fusion protein, a ligand trap, a Fab fragment, a nanobody, a BiTe, and/or the small molecule are effective in preventing and/or treating a tumor, influenza infection, diabetes such as diabetes type II and its side effects, a cardiovascular disease, obesity, hypercholesterolemia such as homozygote familial hypercholesterolemia (HoFH), heterozygote familial hypercholesterolemia (HeFH) or dyslipidemia. An ANGPTL4 oligonucleotide or a pharmaceutical composition of the present invention is used for example in a method of preventing and/or treating a solid tumor or a hematologic tumor. Examples of cancers preventable and/or treatable by use of the oligonucleotide or pharmaceutical composition of the present invention are breast cancer, lung cancer, malignant melanoma, lymphoma, skin cancer, bone cancer, prostate cancer, liver cancer, brain cancer, cancer of the larynx, gall bladder, pancreas, testicular, rectum, parathyroid, thyroid, adrenal, neural tissue, head and neck, colon, stomach, bronchi, kidneys, basal cell carcinoma, squamous cell carcinoma, metastatic skin carcinoma, osteo sarcoma, Ewing's sarcoma, reticulum cell sarcoma, liposarcoma, myeloma, giant cell tumor, small-cell lung tumor, islet cell tumor, primary brain tumor, meningioma, acute and chronic lymphocytic and granulocytic tumors, acute and chronic myeloid leukemia, hairy-cell tumor, adenoma, hyperplasia, medullary carcinoma, intestinal ganglioneuromas, Wilm's tumor, seminoma, ovarian tumor, leiomyomater tumor, cervical dysplasia, retinoblastoma, soft tissue sarcoma, malignant carcinoid, topical skin lesion, rhabdomyosarcoma, Kaposi's sarcoma, osteogenic sarcoma, malignant hypercalcemia, renal cell tumor, polycythermia vera, adenocarcinoma, anaplastic astrocytoma, glioblastoma multiforma, leukemia, or epidermoid carcinoma.

Further examples of diseases preventable and/or treatable by use of the ANGPTL4 oligonucleotide or the pharmaceutical composition of the present invention other than cancer are for example diabetes such as diabetes type II and its side effects, a cardiovascular disease, obesity, hypercholesterolemia such as homozygote familial hypercholesterolemia (HoFH), heterozygote familial hypercholesterolemia (HeFH) or dyslipidemia.

In some examples two or more ANGPTL4 oligonucleotides of the present invention are administered together, at the same time point for example in a pharmaceutical composition or separately, or on staggered intervals. In some examples two or more ANGPTL4 oligonucleotides of the present invention are administered together, at the same time point for example in a pharmaceutical composition or separately, or on staggered intervals. In other examples, one or more oligonucleotides of the present invention are administered together with another compound such as another oligonucleotide not of the present invention, an antibody, a HERA fusion protein, a ligand trap, a Fab fragment, a nanobody, a BiTe, a small molecule and/or a chemotherapeutic, at the same time point for example in a pharmaceutical composition or separately, or on staggered intervals.

A subject of the present invention is for example a mammalian, a bird or a fish.

EXAMPLES

The following examples illustrate different embodiments of the present invention, but the invention is not limited to these examples. The following experiments are performed on cells endogenously expressing ANGPTL4, i.e., the cells do not represent an artificial system comprising transfected reporter constructs. Such artificial systems generally show a higher degree of inhibition and lower $IC_{50}$ values than endogenous systems which are closer to therapeutically relevant in vivo systems. Further, no transfecting agent is used in the following experiments, i.e., gymnotic delivery is performed. Transfecting agents are known to increase the activity of an oligonucleotide which influences the $IC_{50}$ value (see for example Zhang et al., Gene Therapy, 2011, 18, 326-333; Stanton et al., Nucleic Acid Therapeutics, Vol. 22, NO. 5, 2012). As artificial systems using a transfecting agent are hard or impossible to translate into therapeutic approaches and no transfection formulation has been approved so far for oligonucleotides, the following experiments are performed without any transfecting agent, except for the experiments of Example 11, where a transfection reagent was used.

Example 1: 1st Screen of Human ANGPTL4-Specific Antisense Oligonucleotides in HeLa Cells 5,000 HeLa cells/well were seeded in 96-well plates and treated with the respective antisense oligonucleotides as indicated in FIG. 1 at a final concentration of 10 µM. To induce ANGPTL4 mRNA expression, cells were simultaneously treated with 1 µM PPARδ (Sigma Aldrich, Cat. No. SML1491). PPARδ used in the example is for example based on a PPARδ stock solution (10 mM) that was prepared by dissolving 5 mg PPARδ (Molecular weight: 453.50) in 1.1 ml DMSO. For final concentration of 1 µM PPARδ, cells seeded in 96-well plates were incubated with 100 µl medium supplemented with 0.01 µl PPARδ stock solution. As a negative control, cells were treated with equal volume of DMSO. Three days after start of treatment, cells were lysed and human HPRT1 as well as human ANGPTL4 mRNA expression was measured using the QuantiGene RNA Singleplex assay (FIG. 1). The QuantiGene Assay used in the examples is for example built upon the branched DNA technology (bDNA), which relies on cooperative hybridization between a target mRNA and a specific probe set (part of QuantiGene Reagent System). The assay is performed according to manufacturer's protocol (Thermo Fisher Scientific) and is used for determination of RNA levels. It combines the QuantiGene Sample Processing Kit that is used for cell lysis and the QuantiGene Reagent System that is used for hybridization, amplification and detection of RNA of interest. The QuantiGene Reagent System is based on an RNA-specific probe set, designed to detect a particular RNA of interest.

ANGPTL4-mRNA expression values were normalized to expression of the housekeeping gene HPRT1. Residual ANGPTL4-mRNA expression relative to mock-treated cells ("no oligo" set as 1) is shown. Solid line and dotted lines indicate 70% and 50% or 0% knockdown efficacy, respectively. Data are represented as mean of triplicate wells+/−SD.

As shown in FIG. 1, two antisense oligonucleotides (A24022Hi (SEQ ID NO.25) and A24023Hi (SEQ ID NO.26)) reduced the normalized ANGPTL4 expression by more than 70% (equivalent to residual mRNA level of <0.3). Further, three antisense oligonucleotides (A24003He (SEQ ID NO.5), A24042He (SEQ ID NO.45), A24005Hi (SEQ ID NO.7)) showed knockdown efficacy between 70% and 50%, while control oligonucleotide (Neg1) did not reduce ANGPTL4 mRNA expression.

Example 2: 2nd Screen of Human ANGPTL4-Specific Antisense Oligonucleotides in SK-OV3 Cells 5,000 SK-OV3 cells/well were seeded in 96-well plates and treated with the respective ANGPTL4 antisense oligonucleotides at a final concentration of 10 µM. To induce ANGPTL4 mRNA expression, cells were simultaneously treated with 1 µM PPARδ (Sigma Aldrich, cat. no. SML1491; for preparation of 10 mM stock solution see example 1). For final concentration of 1 µM PPARS, cells seeded in 96-well plates were incubated with 100 µl medium supplemented with 0.01 µl PPARδ stock solution. As a negative control, cells were treated with equal volume of DMSO.

Three days after start of treatment, cells were lysed and human HPRT1 as well as human ANGPTL4 mRNA expression was measured using the QuantiGene RNA Singleplex assay. ANGPTL4-mRNA expression values were normalized to expression of the housekeeping gene HPRT1. Residual ANGPTL4-mRNA expression relative to mock-treated cells ("no oligo" set as 1) is shown in FIG. 2. Solid line and dotted lines indicate 60% and 0% knockdown efficacy, respectively. Data are represented as mean of triplicate wells+/−SD.

Repetition of the ANGPTL4 antisense oligonucleotide screening in SK-OV3 cells resulted in three ANGPTL4 antisense oligonucleotides (A24022Hi (SEQ ID NO.25), A24044He (SEQ ID NO.47), A24023Hi (SEQ ID NO.26)) with more than 60% knockdown efficiency.

Example 3: $1^{st}$ Single Dose Efficacy Screen of Further Human ANGPTL4-Specific Antisense Oligonucleotides in HeLa Cells 5,000 HeLa cells/well were seeded in 96-well plates and treated with the most efficient ANGPTL4 antisense oligonucleotides (A24022Hi (SEQ ID NO.25), A24023Hi (SEQ ID NO.26), A24044He (SEQ ID NO.47)) from $1^{st}$ screenings in HeLa (FIG. 1) and SK-OV3 (FIG. 2) as well as further ANGPTL4-specific antisense oligonucleotides (A24071Hi (SEQ ID NO.54), A24076He (SEQ ID NO.47), A24075He (SEQ ID NO.5), A24073Hi (SEQ ID NO.55), A24065Hi (SEQ ID NO.51), A24067Hi (SEQ ID NO.52), A24077He (SEQ ID NO.47), A24074Hi (SEQ ID NO.56)) at a final concentration of 10 µM. To induce ANGPTL4 mRNA expression, cells were simultaneously treated with 1 µM PPARδ (Sigma Aldrich, cat. no. SML1491; for preparation of 10 mM stock solution see example 1). For final concentration of 1 µM PPARδ, cells seeded in 96-well plates were incubated with 100 µl medium supplemented with 0.01 µl PPARδ stock solution. As a negative control, cells were treated with equal volume of DMSO.

Three days after start of treatment, cells were lysed and human HPRT1 as well as human ANGPTL4 mRNA expression was measured using the QuantiGene RNA Singleplex assay. ANGPTL4-mRNA expression values were normalized to expression of the housekeeping gene HPRT1. Residual ANGPTL4-mRNA expression relative to mock-treated cells ("no oligo" set as 1) is shown in FIG. 3. Solid line and dotted lines indicate 50% and 0% knockdown efficacy, respectively. Data are represented as mean of triplicate wells+/−SD.

As shown in FIG. 3, four of the tested ANGPTL4 antisense oligonucleotides (A24022Hi (SEQ ID NO.25), A24023Hi (SEQ ID NO.26), A24044He (SEQ ID NO.47), A24071Hi (SEQ ID NO.54)) show more than 50% knockdown of ANGPTL4 mRNA (equivalent to residual mRNA level of <0.5), while treatment with Neg1 negative control oligonucleotide did not result in decreased ANGPTL4 mRNA levels.

Example 4: $2^{nd}$ Single Dose Efficacy Screen of Further Human ANGPTL4-Specific Antisense Oligonucleotides in SK-OV3 Cells 5,000 SK-OV3 cells/well were seeded in 96-well plates and treated with the respective ANGPTL4 antisense oligonucleotides (A24071Hi (SEQ ID NO.54), A24022Hi (SEQ ID NO.25), A24076He (SEQ ID NO.47), A24044He (SEQ ID NO.47), A24023Hi (SEQ ID NO.26), A24077He (SEQ ID NO.47), A24075He (SEQ ID NO.5), A24073Hi (SEQ ID NO.55)) at a final concentration of 10 µM. To induce ANGPTL4 mRNA expression, cells were simultaneously treated with 1 µM PPARδ. (Sigma Aldrich, cat. no. SML1491; for preparation of 10 mM stock solution see example 1). For final concentration of 1 µM PPARδ, cells seeded in 96-well plates were incubated with 100 µl medium supplemented with 0.01 µl PPARδ stock solution. As a negative control, cells were treated with equal volume of DMSO.

Three days after start of treatment, cells were lysed and human HPRT1 as well as human ANGPTL4 mRNA expression was measured using the QuantiGene RNA Singleplex assay. ANGPTL4-mRNA expression values were normalized to expression of the housekeeping gene HPRT1. Residual ANGPTL4-mRNA expression relative to mock-treated cells ("no oligo" set as 1) is shown in FIG. 4. Solid line and dotted lines indicate 50% and 0% knockdown efficacy, respectively. Data are represented as mean of triplicate wells+/−SD.

Repetition of the optimized ANGPTL4-specific antisense oligonucleotide screening in SK-OV3 cells resulted in five ANGPTL4 antisense oligonucleotides (A24071Hi (SEQ ID NO.54), A24022Hi (SEQ ID NO.25), A24076He (SEQ ID NO.47), A24044He (SEQ ID NO.47), A24023Hi (SEQ ID NO.26)) with more than 50% knockdown efficiency (FIG. 4).

Example 5: In Vitro TLR9 Assay of Selected Human ANGPTL4-Specific Antisense Oligonucleotides Binding of immune stimulatory ligands, e.g. bacterial DNA or immune stimulatory oligonucleotides with or without unmethylated CpG dinucleotides results in TLR activation. As immune activation can lead to severe, possibly life threatening condition of excessive cytokine release, there is an urgent need for a preclinical test system that predicts cytokine release in humans.

HEK-Blue-hTLR9 (Invivogen cat. no. hkb-htlr9) cells were seeded in flat-bottom 96-well plates and treated with ANGPTL4 oligonucleotides A24022Hi (SEQ ID NO. 25), A24023Hi (SEQ ID NO. 26), A24071Hi (SEQ ID NO.54) and A24076He (SEQ ID NO.47) for 24 h. Then, cell supernatants were harvested and incubated for 4 h with QUANTI-Blue solution (Invivogen cat. no. rep-qbs). SEAP activity was determined by measurement of the optical density. Means and standard deviations of OD units relative to OD units from cells stimulated with 5000 nM ODN2006 (set as 100) are depicted in FIG. 5. Data are represented as mean of triplicate wells+/−SD.

As shown in FIG. 5, none of the tested ANGPTL4-specific antisense oligonucleotides induced TLR9 activation. In contrast, positive control CpG oligonucleotide ODN2006 (5'-TCGTCGTTTTGTCGTTTTGTCGTT-3' PTO-modified-Invivogen cat. no. tlrl-2006; SEQ ID NO. 153) clearly stimulated NFκB activation (FIG. 5).

Example 6: $IC_{50}$ Determination of Selected Human ANGPTL4-Specific Antisense Oligonucleotides 30,000 primary human hepatocytes/well were seeded in 96-well plates and treated with different ANGPTL4 antisense oligonucleotides in different concentrations of 5000 nM, 1000 nM, 200 nM, 40 nM, 8 nM and 1.6 nM: A24022Hi (SEQ ID NO.25), A24023Hi (SEQ ID NO.26), A24071Hi (SEQ ID NO.54) and A24076He (SEQ ID NO.47). To induce ANGPTL4 mRNA expression, cells were simultaneously treated with 1 µM PPARγ. (Sigma Aldrich, cat. no. R2408). PPARγ stock solution (10 mM) was prepared by dissolving 10 mg PPARγ (Molecular weight: 357.43) in 2.8 ml DMSO. For final concentration of 1 µM PPARγ, cells seeded in 96-well plates were incubated with 100 l medium supplemented with 0.01 µl PPARγ stock solution. As a negative control, cells were treated with equal volume of DMSO. Every 24 h, 70 µl of supernatant was replaced with fresh medium containing 1 µM PPARγ as well as the respective ANGPTL4 antisense oligonucleotides at indicated concentrations. Three days after start of treatment, cells were lysed and HPRT1 and ANGPTL4 mRNA expression was measured using the QuantiGene RNA Singleplex assay. ANGPTL4-mRNA expression values were normalized to expression of the housekeeping gene HPRT1. Residual ANGPTL4-mRNA expression relative to mock-treated cells (set as 1). For graphic representation mock-treated cells were set as 0.32 nM. Data are represented as mean of triplicate wells+/−SD.

FIG. 6 and Table 5 demonstrate that the selected ANGPTL4-specific antisense oligonucleotides inhibit ANGPTL4 mRNA expression dose-dependently with $IC_{50}$ values in the nanomolar range.

TABLE 5

$IC_{50}$ values of selected human ANGPTL4-specific antisense oligonucleotides determined in primary human hepatocytes.

| ASO | IC50 [nM] | R square |
|---|---|---|
| A24022Hi | 20 | 0.82 |
| A24023Hi | 25 | 0.83 |
| A24071Hi | 16 | 0.83 |
| A24076He | 66 | 0.76 |

Example 7: 1$^{st}$ Single-Dose Screens of Additional Human ANGPTL4-Specific Antisense Oligonucleotides (ASOs) in Primary Hepatocytes In total further 49 ANGPTL4-specific antisense-oligonucleotides were designed. Based on two initial screens in human cell lines (data not shown), 17 promising ASOs were selected for first screen in primary human hepatocytes (FIG. 7). Three control oligonucleotide (R01002, R01014, Neg1) with different lengths (16, 17 and 18 nucleotides, respectively) that do not have sequence complementarity to any human or mouse mRNA were included as negative controls, while three ANGPTL4-specific oligonucleotides with verified knockdown efficiency were used as positive controls (A24022Hi (SEQ ID NO.25), A24071Hi (SEQ ID NO.54), A24076He (SEQ ID NO.47)). Human primary hepatocytes (Lonza) were treated with the respective oligonucleotides at a single concentration of M for three days without the use of a transfection reagent. To induce ANGPTL4 mRNA expression, cells were simultaneously treated with 1 µM PPARγ (Sigma Aldrich, cat. no. R2408; for preparation of 10 mM stock solution see example 6). For final concentration of 1 µM PPARγ, cells seeded in 96-well plates were incubated with 100 l medium supplemented with 0.01 µl PPARγ stock solution. As a negative control, cells were treated with equal volume of DMSO.

Three days after start of treatment, cells were lysed and mRNA levels were determined by QuantiGene RNA Singleplex assay. Hypoxanthine phosphoribosyltransferase 1 (HPRT1) was used as a housekeeping gene for normalization of ANGPTL4 expression. As shown in FIG. 7, PPARγ stimulation resulted in ~50% increased ANGPTL4 levels (no oligo) compared to DMSO-treated cells.

Treatment with eight ANGPTL4-specific ASOs (A24096Hi (SEQ ID NO.172), A24103He (SEQ ID NO.179), A24091Hi (SEQ ID NO.167), A24123He (SEQ ID NO.197), A24083Hi (SEQ ID NO.159), A24087Hi (SEQ ID NO.163), A24102He (SEQ ID NO.178), A24116He (SEQ ID NO.192)) as well as with the positive control ASOs (A24022Hi (SEQ ID NO.25), A24071Hi (SEQ ID NO.54), A24076He (SEQ ID NO.47)) reduced ANGPTL4 expression by more than 70% (equivalent to residual ANGPTL4-mRNA expression of <0.3). Control oligonucleotides (Neg1, R01002, R01014) did not reduce ANGPTL4 mRNA expression.

Example 8: 2$^{nd}$ Single-Dose Screens of Additional Human ANGPTL4-Specific Antisense Oligonucleotides (ASOs) in Primary Hepatocytes Remaining newly designed ANGPTL4-specific ASOs were tested in primary hepatocytes under the experimental conditions of Example 7 (FIG. 8). These ASOs were well tolerated in a subsequent in vitro test (data not shown). One ANGPTL4-specific oligonucleotide with verified knockdown efficiency was used as positive control (A24076He (SEQ ID NO.47)), while three control oligonucleotides (R01009, R01019, Neg1) with different lengths (16, 17 and 18 nucleotides, respectively), that do not have sequence complementarity to any human or mouse mRNA were included as negative controls.

Treatment with ten ANGPTL4-specific ASOs (A24083Hi (SEQ ID NO.159), A24089Hi (SEQ ID NO.165), A24117He (SEQ ID NO.193), A24124He (SEQ ID NO.46), A24103He (SEQ ID NO.179), A24097Hi (SEQ ID NO.173), A24110He (SEQ ID NO.186), A24121He (SEQ ID NO.195), A24086Hi (SEQ ID NO.162), A24085Hi (SEQ ID NO.161)) reduced ANGPTL4 expression by more than 70% (equivalent to residual ANGPTL4-mRNA expression of <0.3), while incubation with positive control ASO A24076H decreased ANGPTL4 mRNA expression by about 63% (FIG. 8). Control oligonucleotides (Neg1, R01009, R01019) only slightly reduced ANGPTL4 mRNA expression (by 6-20%).

Example 9: Activation of Human Toll-Like Receptor 9 (hTLR9) in Response to Human Angiopoietin-Like Protein 4 (ANGPTL4)-Specific LNA-Modified Antisense Oligonucleotides A potential of human ANGPTL4-specific LNA-modified antisense oligonucleotides A24076H (SEQ ID NO.47), A24083Hi (SEQ ID NO.159), A24085Hi (SEQ ID NO.161), A24086Hi (SEQ ID NO.162), A24087Hi (SEQ ID NO.163), A24089Hi (SEQ ID NO.165), A24096Hi (SEQ ID NO.172), A24102He (SEQ ID NO.178), A24103He (SEQ ID NO.179), A24110He (SEQ ID NO.186), A24111He (SEQ ID NO.187), A24113He (SEQ ID NO.189), A24116He (SEQ ID NO.192) and A24123He (SEQ ID NO.197) were tested to activate TLR9. The experiment was conducted once (A24076H, A24096H, A24102He, A24113He, A24116He and A24123He) or twice (all other ASOs) in a TLR9 reporter cell line HEK-Blue-hTLR9 cells (Invivogen cat. no. hkb-htlr9) under the experimental conditions of Example 5. As shown in FIGS. 9A, 9B, 9C and 9D, no dose-dependent activation of NF-κB upon treatment of the cells with different concentrations of the respective human ANGPTL4 ASO was observed. In contrast, NF-κB was activated in a dose-dependent manner upon treatment with the positive control ODN2006 (5'-

TCGTCGTTTTGTCGTTTTGTCGTT-3' PTO-modified-Invivogen cat. no. tlrl-2006; SEQ ID NO. 153).

Example 10: IC$_{50}$ Determination of Selected Human ANGPTL4-Specific Antisense Oligonucleotides (ASOs)

Based on knockdown efficiency in primary hepatocytes (FIGS. 7 and 8), ASOs with most potent knockdown efficacy and no induction of caspase3/7 upon transfection (data not shown) were selected for determination of IC$_{50}$ values. As a positive control ANGPTL4-specific ASO A24076He (SEQ ID NO.47) with verified knockdown efficiency was used.

Primary human hepatocytes (Primacyt) were treated with ANGPTL4-specific ASOs or negative control oligonucleotides Neg1, R01009 and R01019 at different concentrations for three days. Simultaneously, cells were treated with PPARγ (1 µM) (Sigma Aldrich, cat. no. R2408; for preparation of 10 mM stock solution see example 6) to induce ANGPTL4 expression. For final concentration of 1 µM PPARγ, cells seeded in 96-well plates were incubated with 100 µl medium supplemented with 0.01 µl PPARγ stock solution. As a negative control, cells were treated with equal volume of DMSO. After three days, mRNA expression was analyzed using the QuantiGene Singleplex RNA assay.

Table 6 and FIG. 10 demonstrate that the eight ANGPTL4-specific ASOs (A24083Hi (SEQ ID NO.159), A24085Hi (SEQ ID NO.161), A24087Hi (SEQ ID NO.163), A24089Hi (SEQ ID NO.165), A24097Hi (SEQ ID NO.173), A24103He (SEQ ID NO.179), A24110He (SEQ ID NO.186) and A24111He (SEQ ID NO.187)) and the positive control A24076He (SEQ ID NO.47) inhibit ANGPTL4 mRNA expression dose-dependently with IC$_{50}$ values in the nanomolar range. Treatment with ASO A24086Hi (SEQ ID NO.162) did not result in dose-dependent reduction of ANGPTL4 mRNA expression (R squared=0.5). Therefore, data were not included.

Following Table 6 shows IC$_{50}$ values and R squares of selected human ANGPTL4-specific antisense oligonucleotides determined in primary human hepatocytes. *, R square below 0.85.

| ASO | IC$_{50}$ [nM] | R square |
|---|---|---|
| A24083Hi | 28 | 0.95 |
| A24085Hi | 62 | 0.87 |
| A24087Hi | 45 | 0.92 |
| A24089Hi | ~34 | 0.84* |
| A24097Hi | 90 | 0.65* |
| A24103He | 36 | 0.71* |
| A24110He | 12 | 0.93 |
| A24111He | 58 | 0.73* |
| A24076He | 99 | 0.87 |

Example 11: In Vitro Efficacy of Human ANGPTL4-Specific Oligonucleotides in Cynomolgus Hepatocytes In vivo tolerated human ANGPTL4-specific antisense oligonucleotides A24076H (SEQ ID NO.47) as well as three further human ANGPTL4-specific ASOs having only 1 mismatch to cynomolgus ANGPTL4 sequence (Table 7) were tested in primary cynomolgus hepatocytes (FIG. 11). All ASOs tested were shown to have verified knockdown efficiency in human cell lines and primary hepatocytes. Two control oligonucleotides (R01009, R01019) with different lengths (16 and 17 nucleotides, respectively), that do not have sequence complementarity to any human or mouse RNA were included as negative controls.

Table 7 shows human ANGPTL4-specific ASOs with proven knock-down efficiency in human cells that do not lead to caspase 3/7 induction in vitro. Depicted are cross-reactivity (CrossReact) as well as number of mismatches to cynomolgus (Mfa, *Macaca fascicularis*) ANGPTL4 sequence, as well as activity in primary cynomolgus hepatocytes in vitro (FIG. 11):

| Target | ASO ID | SEQ ID NO. | CrossReact_Mfa | Mismatches to Mfa sequence | Activity in Mfa hepatocytes |
|---|---|---|---|---|---|
| ANGPTL4 | A24076He | 47 | yes | 0 | + |
| | A24083Hi | 159 | no | 4 | NA |
| | A24085Hi | 161 | no | 4 | NA |
| | A24086Hi | 162 | no | 6 | NA |
| | A24087Hi | 163 | no | 3 | NA |
| | A24089Hi | 165 | no | 1 | + |
| | A24097Hi | 173 | no | 3 | NA |
| | A24103He | 179 | no | 5 | NA |
| | A24110He | 186 | no | 1 | + |
| | A24111He | 187 | no | 1 | + |

Primary cynomolgus hepatocytes (Primacyt) were transfected with ANGPTL4-specific ASOs or negative control oligonucleotides R01009 and R01019 at different concentrations for three days. Simultaneously, cells were treated with PPARδ (1 µM) (Sigma Aldrich, cat. no. R2408; for preparation of 10 mM stock solution see example 6) to induce ANGPTL4 expression. For final concentration of 1 µM PPARγ, cells seeded in 96-well plates were incubated with 100 µl medium supplemented with 0.01 µl PPARγ stock solution. As a negative control, cells were treated with equal volume of DMSO. After three days, mRNA expression was analyzed using the QuantiGene Singleplex RNA assay.

As shown in FIG. 11, treatment with PPARδ induced ANGPTL4 expression about 8-fold (FIG. 11, DMSO control). Treatment with the ANGPTL4-specific ASO A24076He (SEQ ID NO.47), which is completely cross-reactive to cynomolgus ANGPTL4 sequence led to more than 70% knock-down of ANGPTL4 (equivalent to residual mRNA expression of 0.3). Human ANGPTL4-specific oligonucleotides having one mismatch to cynomolgus sequence (A24089Hi (SEQ ID NO.165), A24110He (SEQ ID NO.186), A24111He (SEQ ID NO.187)) also reduced cynomolgus ANGPTL4 mRNA up to 51% (equivalent to residual ANGPTL4-mRNA expression of 0.49). Negative control oligonucleotide R01009 did not reduce Angptl4 expression in primary cynomolgus hepatocytes, while control oligonucleotide R01019 only slightly decreased ANGPTL4 mRNA expression by about 25% (equivalent to residual ANGPTL4-mRNA expression of 0.75) using a concentration of 2 nM.

Conclusion Based on Example 11

Taken together, the in vitro experiments led to the identification of highly potent human ANGPTL4 specific ASOs that are eligible for testing of an ASO-based ANGPTL4-targeting therapeutic in cynomolgus monkeys. Such a drug is used for example for the systemic treatment of dyslipidemia patients in order to reduce the ANGPTL4-mediated inhibition of lipoprotein lipase L preventing cellular lipid overload, obesity, diabetes type II and cardiovascular disease.

Example 12: 1$^{st}$ Single-Dose Screen of Mouse ANGPTL4-Specific Antisense Oligonucleotides in 3T3 Cells 4,500 3T3 cells/well were seeded in 96-well plates and treated with the ANGPTL4 antisense oligonucleotides as shown in FIG. 12 at a final concentration of 10 µM. Cells were lysed and mouse Hprt1 and mouse ANGPTL4 mRNA expression was measured using the QuantiGene RNA Singleplex assay. ANGPTL4-mRNA expression values were normalized to expression of the housekeeping gene Hprt1. Residual ANGPLT4-mRNA expression relative to mock-treated cells ("no oligo" set as 100) is shown in FIG. 12. Solid line and dotted line indicate 50% and 0% knockdown efficacy, respectively. Data are represented as mean of triplicate wells+/−SD.

As shown in FIG. 12, eight ANGPTL4 antisense oligonucleotides, i.e., A24047M (SEQ ID NO.106), A24020M (SEQ ID NO.79), A24017M (SEQ ID NO.76), A24021M (SEQ ID NO.80), A24049M (SEQ ID NO.108), A24018M (SEQ ID NO.77), A24041M (SEQ ID NO. 100) and A24010M (SEQ ID NO.69), reduced the normalized ANGPTL4 expression by more than 50%, while control oligonucleotide (Neg1) did not reduce ANGPTL4 mRNA expression (FIG. 12).

Example 13: 2$^{nd}$ Single-Dose Efficacy Screen of Mouse ANGPTL4-Specific Antisense Oligonucleotides in Renca Cells 5,000 Renca cells/well were seeded in 96-well plates and treated with the ANGPTL4 antisense oligonucleotides as shown in FIG. 13 at a final concentration of 10 µM. Three days after start of treatment, cells were lysed and mouse Hprt1 and mouse ANGPTL4 mRNA expression was measured using the QuantiGene RNA Singleplex assay. ANGPTL4-mRNA expression values were normalized to expression of the housekeeping gene Hprt1. Residual ANGPTL4-mRNA expression relative to mock-treated cells ("no oligo" set as 1) is shown. Solid line and dotted line indicate 50% and 0% knockdown efficacy, respectively. Data are represented as mean of triplicate wells+/−SD.

As shown in FIG. 13, treatment with two ANGPTL4-specific antisense oligonucleotides, which are A24020M (SEQ ID NO.79) and A24019M (SEQ ID NO.78) resulted in ANGPTL4 knockdown of more than 50% (equivalent to residual mRNA level of <0.5) (FIG. 13).

Example 14: Test of Further Mouse ANGPTL4-Specific Antisense Oligonucleotides in 4T1 Cells 2,500 4T1 cells/well were seeded in 96-well plates and treated with the ANGPTL4 antisense oligonucleotides (ASO) as shown in FIG. 14 at a final concentration of 5 µM. After 3 d, cell supernatant was replaced by fresh medium w/ ASO. Six days after start of treatment, cells were lysed and mouse Gapdh and mouse ANGPTL4 mRNA expression were measured using the QuantiGene RNA Singleplex assay. ANGPTL4-mRNA expression values were normalized to expression of the housekeeping gene Gapdh. Residual ANGPTL4-mRNA expression relative to Neg1-treated cells (set as 1) is shown. Solid line and dotted lines indicate 80% and 0% knockdown efficacy, respectively. Data are represented as mean of triplicate wells+/−SD.

As shown in FIG. 14, 12 of the tested antisense oligonucleotides, which are A24017M (SEQ ID NO.76), A24070M (SEQ ID NO.127), A24020M (SEQ ID NO.79), A24019M (SEQ ID NO.78), A24069M (SEQ ID NO.126), A24021M (SEQ ID NO.80), A24011M (SEQ ID NO.70), A24073M (SEQ ID NO.130), A24018M (SEQ ID NO.77), A24055M (SEQ ID NO.114), A24010M (SEQ ID NO.69), and A24065M (SEQ ID NO.79) show more than 80% knockdown of ANGPTL4 mRNA (equivalent to residual mRNA level of <0.2).

Example 15: Single-Dose Efficacy Screen of Intron-Targeting Mouse ANGPTL4-Specific Antisense Oligonucleotides in 4T1 Cells 2,500 4T1 cells/well were seeded in 96-well plates and treated with the ANGPTL4 antisense oligonucleotides (ASO) as shown in FIG. 15 at a final concentration of 5 µM. Three days after start of treatment, cell supernatant was replaced by fresh medium w/ASO and cells were incubated for additional 3 d. Then, cells were lysed and mouse Hprt1 and mouse ANGPTL4 mRNA expression was measured using the QuantiGene RNA Singleplex assay. ANGPTL4-mRNA expression values were normalized to expression of the housekeeping gene Hprt1. Residual ANGPTL4-mRNA expression relative to mock-treated cells ("no oligo" control set as 1) is shown. Solid line and dotted lines indicate 50% and 0% knockdown efficacy, respectively. Data are represented as mean of triplicate wells+/−SD.

As shown in FIG. 15, six of the tested ANGPTL4 antisense oligonucleotides, which are A24047M (SEQ ID NO.106), A24095Mi (SEQ ID NO.151), A24093Mi (SEQ ID NO.149), A24020M (SEQ ID NO.79), A24090Mi (SEQ ID NO.146), and A24082Mi (SEQ ID NO.139) show more than 50% knockdown of ANGPTL4 mRNA (equivalent to residual mRNA level of <0.5).

Example 16: IC$_{50}$ Determination of Selected Mouse ANGPTL4-Specific Antisense Oligonucleotides 2,500 4T1 cells/well were seeded in 96-well plates and treated with the respective ANGPTL4 antisense oligonucleotides (ASO) A24018M (SEQ ID NO.77), A24019M (SEQ ID NO.78), A24020M (SEQ ID NO.79), A24021M (SEQ ID NO.80), A24047M (SEQ ID NO.106), A24054M (SEQ ID NO.113), A24065M (SEQ ID NO.79), A24070M (SEQ ID NO.127), A24072M (SEQ ID NO.129), A24082M (SEQ ID NO.139) and A24095Mi (SEQ ID NO.151) at different concentrations of 5000 nM, 1000 nM, 200 nM, 40 nM, 8 nM and 1.6 nM. Three days after start of treatment, cell supernatant was replaced by fresh medium w/ ASO and cells were incubated for additional 3 d. Then, cells were lysed and mouse Hprt1 and mouse ANGPTL4 mRNA expression was measured using the QuantiGene RNA Singleplex assay. ANGPTL4-mRNA expression values were normalized to expression of the housekeeping gene Hprt1. Residual ANGPTL4-mRNA expression relative to mock-treated cells ("no oligo" control set as 1) is shown. Data are represented as mean of triplicate wells+/−SD.

FIG. 16 and Table 8 demonstrate that the selected ANGPTL4-specific antisense oligonucleotides inhibit ANGPTL4 mRNA expression dose-dependently with $IC_{50}$ values in the nanomolar range.

TABLE 8

$IC_{50}$ values of selected mouse ANGPTL4-specific antisense oligonucleotides determined in 4T1 cells.

| ASO | $IC_{50}$ [nM] | R square |
|---|---|---|
| A24018M | 447 | 0.90 |
| A24019M | 122 | 0.87 |
| A24020M | 475 | 0.91 |
| A24021M | 283 | 0.68 |
| A24047M | 556 | 0.70 |
| A24054M | 350 | 0.85 |
| A24065M | 380 | 0.80 |
| A24070M | 329 | 0.59 |
| A24072M | 61 | 0.92 |
| A24082Mi | 56 | 0.65 |
| A24095Mi | 223 | 0.64 |

Example 17: 1$^{st}$ Single-Dose Screen of Additional Mouse Angptl4-Specific ASOs in 4T1 Cells Mouse Angptl4-specific antisense-oligonucleotides were designed. In the initial screen 53 ASOs targeting Angptl4 mRNA were tested. Three control oligonucleotides (R01002, R01014, Neg1) with different lengths (16, 17 and 18 nucleotides, respectively), that do not have sequence complementarity to any human or mouse mRNA were included as negative controls, whereas three ANGPTL4-specific oligonucleotides (A24047M (SEQ ID NO.106), A24072M (SEQ ID NO.129), A24095Mi (SEQ ID NO.151)) with verified knockdown efficiency were used as positive controls. Mouse breast cancer cells (4T1 cells) were treated with the respective oligonucleotides at a single concentration of 5 µM. After three days, cell supernatant was replaced by fresh medium containing 5 µM of the respective ASO and incubated for further three days. Afterwards, cells were lysed and mRNA levels were determined by Quanti-Gene RNA Singleplex assay. Hprt1 was used as a housekeeping gene for normalization of Angptl4 expression.

As shown in FIG. 17, 15 ASOs (A24146Mi (SEQ ID NO.247), A24047M (SEQ ID NO.106), A24126Mi (SEQ ID NO.227), A24120Mi (SEQ ID NO.221), A24104M (SEQ ID NO.207), A24108M (SEQ ID NO.211), A24110M (SEQ ID NO.213), A24139Mi (SEQ ID NO.240), A24103M (SEQ ID NO.206), A24112M (SEQ ID NO.107), A24122HMe (SEQ ID NO.196), A24113M (SEQ ID NO.108), A24125Mi (SEQ ID NO.226), A24099M (SEQ ID NO.202), A24095Mi (SEQ ID NO.151)) reduced Angptl4 expression by more than 75% (equivalent to residual Angptl4-mRNA expression of <0.25), while control oligonucleotides (Neg1, R01002, R01014) reduced Angptl4 mRNA expression by less than 50% (equivalent to residual Angptl4-mRNA expression of >0.5) (FIG. 17).

Example 18: 2$^{nd}$ Single-Dose Screen of Mouse Angptl4-Specific ASOs in Renca Cells For further confirmation in a different cell line, the same treatment as in Example 17 was applied to mouse Renca cells. Thereby, treatment with 19 Angptl4-specific ASOs (A24143Mi (SEQ ID NO.244), A24047M (SEQ ID NO.106), A24095Mi (SEQ ID NO.151), A24125Mi (SEQ ID NO.226), A24110M (SEQ ID NO.213), A24148Mi (SEQ ID NO.151), A24120Mi (SEQ ID NO.221), A24104M (SEQ ID NO.207), A24109M (SEQ ID NO.212), A24139Mi (SEQ ID NO.240), A24103M (SEQ ID NO.206), A24122HMe (SEQ ID NO.196), A24131Mi (SEQ ID NO.232), A24138Mi (SEQ ID NO.239), A24123Mi (SEQ ID NO.224), A24146Mi (SEQ ID NO.247), A24117Mi (SEQ ID NO.218), A24130Mi (SEQ ID NO.231), A24144Mi (SEQ ID NO.245)) resulted in Angptl4 knockdown of more than 75% (equivalent to residual Angptl4-mRNA expression of <0.25) (FIG. 18).

Example 19: $IC_{50}$ Determination of Selected Mouse ANGPTL4-Specific Antisense Oligonucleotides Based on results of knockdown efficiencies in 4T1 and Renca cells (FIG. 17, 18), nine ASOs (A24103M (SEQ ID NO.206), A24110M (SEQ ID NO.213), A24122HMe (SEQ ID NO.196), A24120Mi (SEQ ID NO.221), A24125Mi (SEQ ID NO.226), A24139Mi (SEQ ID NO.240), A24143Mi (SEQ ID NO.244), A24146Mi (SEQ ID NO.247), A24148Mi (SEQ ID NO.151)) with most potent knockdown efficacy Renca and 4T1 cells were selected for determination of half maximal inhibitory concentration ($IC_{50}$) values.

Primary mouse hepatocytes were treated with the respective ASO at different concentrations for three days. After three days, mRNA expression was analyzed using the QuantiGene Singleplex RNA assay. FIG. 19 and Table 9 demonstrate that the selected Angptl4-specific ASOs inhibit Angptl4 mRNA expression dose-dependently with $IC_{50}$ values in the nanomolar range.

Table 9 shows $IC_{50}$ values of selected Angptl4-specific ASOs determined in primary human hepatocytes. *, R square below 0.85; ASOs with increased potential to induce caspase3/7 leading to dose-dependent decrease of Hprt1 levels:

| ASO | $IC_{50}$ [nM] | R square |
|---|---|---|
| A24103M | 159 | 0.90 |
| A24110M | 346 | 0.72* |
| A24122HMe | 117 | 0.98 |
| A24120Mi | 126 | 0.86 |
| A24125Mi | 70 | 0.91 |
| A24139Mi | 250 | 0.92 |
| A24143Mi | 60 | 0.84* |
| A24146Mi | 26 | 0.98 |
| A24148Mi | 88 | 0.97 |
| A24047M | 89 | 0.96 |
| A24072M | 118 | 0.96 |
| A24095Mi | 72 | 0.94 |

Conclusion Based on the Examples 7-11 and 17-19

Testing a set of 47 further ASOs with specificity for human ANGPTL4, several ASOs were selected that potently reduce the expression of human ANGPTL4 in primary hepatocytes on the mRNA level. Treatment with 16 of the tested ASOs showed more than 70% knockdown of ANGPTL4 mRNA in primary human hepatocytes cells. Thereby, $IC_{50}$ values of most potent candidates were in low nanomolar range.

In order to conduct in vivo experiments in mouse models ASOs were designed with specificity for mouse Angptl4 and successful candidate ASOs were selected for in vivo studies that potently knock down mouse Angptl4 expression in vitro.

Taken together, a comprehensive set of in vitro experiments was conducted that led to the identification of highly potent human ANGPTL4 specific ASOs that are eligible for the development of an ASO-based ANGPTL4-targeting therapeutic.

What is claimed is:

1. A method of reducing ANGPTL4 expression in a subject, the method comprising administering a pharmaceutically active amount of an ANGPTL4 inhibitor consisting of an antisense oligonucleotide of 12 to 22 nucleotides, wherein at least one nucleotide in the antisense oligonucleotide is modified, and wherein the antisense oligonucleotide is complementary to a corresponding portion of 12 to 22 consecutive nucleotides of positions 3415-3442 of SEQ ID NO: 2 to the subject in need of the reducing, and wherein the antisense oligonucleotide inhibits the expression of ANGPTL4.

2. The method according to claim 1, wherein the antisense oligonucleotide of 12 to 22 nucleotides is a gapmer and comprises a central core of at least 5 consecutive deoxyribonucleotides and/or ribonucleotides.

3. The method according to claim 1, wherein at least one of the modified nucleotides of the antisense oligonucleotide is a 2' modified nucleotide or a bridged nucleotide.

4. The method according to claim 1, wherein at least one of the modified nucleotides of the antisense oligonucleotide is selected from a locked nucleic acid (LNA), cET, ENA, a 2'Fluoro modified nucleotide, a 2'O-Methyl modified nucleotide, 2'-Methoxyethyl modified nucleotide or a combination thereof.

5. The method according to claim 1, wherein at least one of the modified nucleotides of the antisense oligonucleotide is LNA.

6. The method according to claim 1, wherein the antisense oligonucleotide comprises a modified phosphate backbone.

7. The method according to claim 6, wherein the modified phosphate is a phosphorothioate.

8. The method according to claim 1, wherein the subject has a cardiometabolic disease selected from the group consisting of obesity, diabetes, hypercholesterolemia, hypertriglyceridemia (HTG), dyslipidemia, pancreatitis, metabolic syndrome, and familial chylomicronemia syndrome (FCS).

9. The method according to claim 8, wherein the hypercholesterolemia is selected from the group consisting of homozygous familial hypercholesterolemia (HoFH) and heterozygous familial hypercholesterolemia (HeFH).

10. The method according to claim 8, wherein the diabetes is type 2 diabetes.

11. The method according to claim 1, wherein the subject has a respiratory infection.

12. The method according to claim 11, wherein the respiratory infection is influenza.

13. The method according to claim 1, wherein the subject has cancer.

14. The method according to claim 13, wherein the cancer is selected from the group consisting of breast cancer, lung cancer, malignant melanoma, lymphoma, skin cancer, bone cancer, prostate cancer, liver cancer, brain cancer, cancer of the larynx, gall bladder, pancreas, testicular, rectum, parathyroid, thyroid, adrenal, neural tissue, head and neck, colon, stomach, bronchi, kidneys, basal cell carcinoma, squamous cell carcinoma, metastatic skin carcinoma, osteo sarcoma, Ewing's sarcoma, reticulum cell sarcoma, liposarcoma, myeloma, giant cell tumor, small-cell lung tumor, islet cell tumor, primary brain tumor, meningioma, acute and chronic lymphocytic and granulocytic tumors, acute and chronic myeloid leukemia, hairy-cell tumor, adenoma, hyperplasia, medullary carcinoma, intestinal ganglioneuromas, Wilm's tumor, seminoma, ovarian tumor, leiomyomater tumor, cervical dysplasia, retinoblastoma, soft tissue sarcoma, malignant carcinoid, topical skin lesion, rhabdomyosarcoma, Kaposi's sarcoma, osteogenic sarcoma, malignant hypercalcemia, renal cell tumor, polycythermia vera, adenocarcinoma, anaplastic astrocytoma, glioblastoma multiforma, leukemia, and epidermoid carcinoma.

15. The method according to claim 13, wherein the cancer is lung cancer.

16. The method according to claim 1, wherein the oligonucleotide comprises the sequence (SEQ ID NO:165) (5'-3') TCGAAATGAGTCTGCAC.

17. The method according to claim 16, wherein the oligonucleotide comprises the sequence (5'-3') +T*+C*+G*A*A*A*T*G*A*G*T*C*T*G*+C*+A*+C (SEQ ID NO:165), wherein + indicates a locked nucleic acid (LNA) nucleotide and * indicates a phosphorothioate (PTO) linkage between the nucleotides.

18. The method according to claim 3, wherein the bridged nucleotide is a 2'-4' bridged nucleotide.

* * * * *